US012187755B2

(12) United States Patent
Gin et al.

(10) Patent No.: US 12,187,755 B2
(45) Date of Patent: *Jan. 7, 2025

(54) MINIMAL SAPONIN ANALOGUES, SYNTHESIS AND USE THEREOF

(71) Applicant: MEMORIAL SLOAN-KETTERING CANCER CENTER, New York City, NY (US)

(72) Inventors: David Y. Gin, New York, NY (US); Eric K. Chea, Flushing, NY (US); Alberto Fernandez-Tejada, New York, NY (US); Derek S. Tan, New York, NY (US); Jason S. Lewis, New York, NY (US); Jeffrey R. Gardner, New York, NY (US); NagaVaraKishore Pillarsetty, Jackson Heights, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/694,180

(22) Filed: Mar. 14, 2022

(65) Prior Publication Data

US 2022/0275017 A1 Sep. 1, 2022

Related U.S. Application Data

(63) Continuation of application No. 16/853,393, filed on Apr. 20, 2020, now Pat. No. 11,274,116, which is a continuation of application No. 15/314,792, filed as application No. PCT/US2015/033567 on Jun. 1, 2015, now Pat. No. 10,626,137.

(60) Provisional application No. 62/005,302, filed on May 30, 2014.

(51) Int. Cl.
| | | |
|---|---|---|
| *A61K 31/704* | (2006.01) | |
| *A61K 31/7024* | (2006.01) | |
| *A61K 39/39* | (2006.01) | |
| *A61K 45/06* | (2006.01) | |
| *C07H 15/18* | (2006.01) | |
| *C07H 15/24* | (2006.01) | |
| *C07H 15/256* | (2006.01) | |
| *A61K 39/00* | (2006.01) | |

(52) U.S. Cl.
CPC ....... *C07H 15/256* (2013.01); *A61K 31/7024* (2013.01); *A61K 31/704* (2013.01); *A61K 39/39* (2013.01); *A61K 45/06* (2013.01); *C07H 15/18* (2013.01); *C07H 15/24* (2013.01); *A61K 2039/55577* (2013.01)

(58) Field of Classification Search
None
See application file for complete search history.

(56) References Cited

U.S. PATENT DOCUMENTS

| | | | | |
|---|---|---|---|---|
| 10,626,137 B2* | 4/2020 | Gin | ......................... | A61K 39/39 |
| 10,906,926 B2* | 2/2021 | Gin | ......................... | C07H 13/04 |
| 11,274,116 B2* | 3/2022 | Gin | ......................... | C07H 15/18 |
| 11,324,821 B2* | 5/2022 | Martin | ............... | A61K 39/0011 |
| 2012/0136142 A1 | 5/2012 | Pathak et al. | | |
| 2013/0011421 A1* | 1/2013 | Gin | ......................... | A61P 31/20 |
| | | | | 424/278.1 |

FOREIGN PATENT DOCUMENTS

| | | |
|---|---|---|
| CN | 103265606 | 8/2013 |
| CN | 103265606 A | 8/2013 |
| CN | 103694375 | 4/2014 |
| CN | 103694375 A | 4/2014 |
| CN | 106573951 B | 9/2020 |
| JP | 2011-516566 | 5/2011 |
| JP | 2011-516566 A | 5/2011 |
| WO | 2009/126737 A2 | 10/2009 |
| WO | 2009126737 | 10/2009 |
| WO | 2014/063441 A1 | 5/2014 |
| WO | 2014063441 | 5/2014 |

OTHER PUBLICATIONS

Quang et al., Journal of Natural Products, 2011, vol. 74, pp. 1908-1915 (Year: 2011).*
Chea et al., Journal of the American Chemical Society, 2012, vol. 134, No. 32, pp. 13448-13457 (Year: 2012).*
Berge, et al. "Pharmaceutical Salts", Journal of Pharmaceutical Sciences, Jan. 1977, vol. 66, pp. 1-19 (Abstract Only).
Koziorowski, et al. "A new convenient route to radioiodinated N-succinimidyl 3- and 4-iodobenzoate, two reagents for radioiodination of proteins", Applied Radiation and Isotopes, 1998, vol. 49, pp. 955-959. (Abstract Only).
Dissertation: "Design and Synthesis of Quillaja Saponin Adjuvants and Synthesis of Lablaboside Saponins," pp. 29-30, Dec. 31, 2013.
Office Action issued on Nov. 28, 2017 for Singapore Patent Application No. 11201610004P.
Extended European Search Report issued on Nov. 27, 2017 for European Patent Application No. 15798814.8.
Hani, M. et al., "A Novel Triterpene Saponin from Gypsophila Capillaris," pp. 563-567, Apr. 1, 1995, [Retrieved from the Internet] <https://www.degruyter.com/downloadpdf/j/znb.1995.50.issue-4/znb-1995-0415/znb-1995-0415.pdf>.
Luo, Jian-Guang et al., "New Triterpenoid Saponins with Strong *-glucosidase Inhibitory Activity from the Roost of Gypsophila Oldhamiana," Bioorganic & Medicinal Chemistry, vol. 16, pp. 2912-2920, 2008.

(Continued)

*Primary Examiner* — Traviss C McIntosh, III
(74) *Attorney, Agent, or Firm* — Hunton Andrews Kurth LLP

(57) ABSTRACT

Truncated triterpene saponin analogues containing a trisaccharide or tetrasaccharide ester are disclosed. Also disclosed are pharmaceutical compositions comprising truncated saponin analogues and synthetic methods of producing the truncated saponin analogues. Another aspect of the present application relates to a method for immunizing a subject, comprising administering to the subject the pharmaceutical composition comprising a minimal saponin analogue and an antigen.

13 Claims, 35 Drawing Sheets

(56) References Cited

OTHER PUBLICATIONS

Zou, Cheng et al., "Diacylated Triterpenoid Saponin from Silene Szechunsis," Chinese Chemical Letters, vol. 10, No. 1, pp. 33-36, 1999.
Fernandez-Tejada, Alberto et al., "Development of Minimal Saponin Vaccine Adjuvant Based on Qs-21," Nature Chemistry, vol. 6, No. 7, pp. 635-643, Jun. 1, 2014.
Fernandez-Tejada, Alberto et al., "Design, Synthesis, and Immunologic Evaluation of vaccine Adjuvant Conjugates based on QS-21 and Tucaresol," Bioorganic & Medicinal Chemistry, vol. 22, pp. 5917-5923, 2014.
Ma, Li et al., "Triterpenoid Saponins from Dianthus Versicolor," J. Nat. Prod. vol. 72, No. 4, pp. 640-644, Apr. 24, 2009.
Chea, Eric K. et al., "Synethsis and Preclinical Evaluation of Qs-21 Variants Leading to Simplified Vaccine Adjuvants and Mechanistic Probes," J. Am. Chem Soc, vol. 134, No. 32, pp. 13448-13457, Aug. 15, 2012.
Hani, M. et al., "A Novel Triterpene Sapoonin Gypsophila Capilaris," pp. 563-567, Apr. 1, 1995, [Retrieved from the Internet] <https://www.degruyter.com/downloadpdf/j/znb.1995.50.issue-4/znb-1995-0415/znb-1995-0415.pdf.
Plechanovova, Anna et al., "Novel Substrate-Based Inhibitors of Human Glutamate Carboxypeptidase II with Enhanced Lipophilicity," J Med Chem, vol. 54, No. 21, pp. 7535-7546, Nov. 10, 2011.
McNab, Jennifer A. et al., "Quantitative Short Echo-Time 1H Laser-CSI in Human Brain at 4T," NMR in Biomedicine, vol. 19, pp. 999-1009, 2006.
Elgamal, M. Hani. A et al., Isolation of Triterpene Saponins from Gypsophila Capillaris, Phytochemistry, vol. 38, No. 6, pp. 1481-1485, 1995.
Database Registry, Chemical Abstract Services, STN Accession No. 1596376-86-1, May 2, 2014.
Database Registry, Chemical Abstract Services, STN Accession No. 1424801-42-2, Mar. 18, 2013.
Database Registry, Chemical Abstract Services, STN Accession No. 946617-18-1, Sep. 11, 2007.
Database Registry, Chemical Abstract Services, STN Accession No. 99633-30-4, Jan. 4, 1986.
Database Registry, Chemical Abstract Services, STN Accession No. 57539-70-5 and 30688-36-9, Nov. 16, 1984.
Deng, Kai et al., "Synthesis and structure verification of the vaccine adjuvant QS-7-Api. Synthetic access to Homogeneous Quillaja Saponaria Immunostimulants," J. Am. Chem. Soc. 130, pp. 5860-5861, 2008.
Koziorowski, J., et al., "A New Convenient Route to Radioiodinated N-succinimidyl 3- and 4-iodobenzoate, Two Reagents for Radioiodination of proteins," Appl. Radiat. Isot., vol. 49, pp. 955-959, 1998.
Zhi, Yong-Gang et al., "Systematic studies on Photoluminescence of oligo(arylene-ethynylene)s: tunability of excited states and derivatization as luminescent labeling probes for proteins," Eur. J. Org. Chem., pp. 3125-3139, 2006.
Shell, Thomas A., "Selective Targeting of DNA for cleavage within DNA-Histone Assemblies by a Spermine-[CpW (CO)3Ph]2 Conjugate," Org. Biomol. Chem., vol. 3, pp. 3091-3093, 2005.
Berge, Stephen M. et al., "Describe Pharmaceutically Acceptable salts in Detail," J. Pharmaceutical Sciences, vol. 66, pp. 1-19, 1977.
Chiliean Examiner's Report dated Jun. 18, 2018 for Chilean Patent Application No. 3048-2016.
International Search Report and Written Opinion for International Patent Application No. PCT/US15/33567 mailed Aug. 12, 2015.
Chea, E.K., et al., "Synthesis and Preclinical Evaluation of QS-21 Variants Leading to Simplified Vaccine Adjuvants and Mechanistic Probes," J Am Chem Soc., Aug. 2012, vol. 134, No. 32, pp. 1-26.
Elgamal, M.H.A., et al., "Isolation of Triterpene Saponins from Gypsophila Capillaris," Phytochemistry, 1995, vol. 38, No. 6, pp. 1481-1485.
Plechanovová, A., et al., "Novel Substrate-Based Inhibitors of Human Glutamate Carboxypeptidase II with Enhanced Lipophilicity," J Med Chem., Nov. 2011, vol. 54, No. 21, pp. 1-24.

First Examiner's Report dated Jun. 21, 2018 or Singapore Patent Application No. 201603048.
Singapore Written Opinion issued on Oct. 2, 2018 for Singapore Patent Application 11201610004P.
Examination Report No. 1 for Standard Patent Application dated Dec. 11, 2018 for Australian Patent Application No. 2015266624.
Invitation to Respond to Written Opinion dated Oct. 5, 2018 for Singapore Patent application No. 11201610004P.
Chile Examiner's Report dated Nov. 12, 2018 for Chile Patent Application No. 201603048.
Notification of the Second Office Action dated Apr. 16, 2019 for Chinese Patent Application No. 201580041489.X.
Notification of Reasons for Refusal dated Jun. 25, 2019 for Japanese Patent Application No. 2017-515877.
Elgama et al., "A Novel Triterpene Saonin from Gypsohila capillaris", 1995, Zeitschrift fur Naturforschung, vol. 50b, pp. 563-567.
Luo, Jian-Guang et al., "New triterpenoid saponins with strong . . . ", 2008, Bioorganic & Medicinal Chemistry, vol. 16, pp. 2912-2920.
Zou, Cheng et al., "Diacylated Triterpenoid Saponin from Silene szechuensis" Chinese Chemical Letters, 1999, vol. 10, No. 1, pp. 33-36.
Hani, M. et al., "Isolation of Triterpene Saponins from Gypsophila Capillaris" Phytochemistry, 1995, vol. 38, No. 6, pp. 1481-1485.
Examination Report dated Aug. 26, 2019 for Indian Application No. 201627040808.
Communication pursuant to Article 94(3) EPC dated Nov. 6, 2019 for European Patent application No. 15798814.8.
Notification of the Third Office Action dated Sep. 29, 2019 for Chinese Patent application No. 201580041489.X.
Arrau et al. Journal of Ethnopharmacology, 2011, vol. 133(1), pp. 164-167 (2011).
Communication pursuant to Article 94(3) EPC dated Mar. 4, 2019 for European Patent Application No. 15798814.8.
Quang et al., Journal of Natural Products, 2011, vol. 74, pp. 1098-1915.
Australian Examination Report dated Jun. 30, 2020 for Standard Australian Patent Application No. 2019279971.
Notification of the Third Office Action dated Sep. 29, 2019 for Chinese Patent application No. 201580041489.X [Cited in Parent U.S. Pat. No. 10,626,137 issued on Apr. 21, 2020].
Chea et al., Journal of the American Chemical Society, 2012, 134(32), pp. 13448-13457. (Year: 2012).
Communication pursuant to Article 94(3) EPC dated Nov. 6, 2019 for European Patent application No. 15798814.8 [Cited in Parent U.S. Pat. No. 10,626,137 issued on Apr. 21, 2020].
Examination Report dated Aug. 26, 2019 for Indian Application No. 201627040808 [Cited in Parent U.S. Pat. No. 10,626,137 issued on Apr. 21, 2020].
Notification of the Second Oftlce Action dated Apr. 16, 2019 for Chinese Patent Application No. 201580041489.X [Cited in Parent U.S. Pat. No. 10,626,137 issued on Apr. 21, 2020].
Notification of Reasons for Refusal dated Jun. 25, 2019 for Japanese Patent Application No. 2017-515877 [Cited in Parent U.S. Pat. No. 10,626,137 issued on Apr. 21, 2020].
Elgama et al., "A Novel Triterpene Saonin from Gypsohila capillaris", 1995, Zeltschim fur Naturforschung, vol. 50b, pp. 563-567 [Cited in Parent U.S. Pat. No. 10,626,137 issued on Apr. 21, 2020].
Luo, Jian-Guang et al., New triterpenoid saponins with strong . . . , 2008, Bloorganic & Medicinal Chemistry, vol. 16, pp. 2912-2920 [Cited in Parent U.S. Pat. No. 10,626,137 issued on Apr. 21, 2020].
Zou, Cheng et al., "Diacylated Triterpenoid Saponin from Silene szechuensis" Chinese Chemical Letters, 1999, vol. 10, No. 1, pp. 33-36 [Cited in Parent U.S. Pat. No. 10,626,137 issued on Apr. 21, 2020].
Hani, M. et al., "Isolation of Triterpene Saponins from Gypsophila Capillaris" Phytochemistry, 1995, vol. 38, No. 6, pp. 1481-1485 [Cited in Parent U.S. Pat. No. 10,626, 137 issued on Apr. 21, 2020].
Communication pursuant to Article 94(1) EPC dated Mar. 4, 2019 for European Patent Application No. 15798814.8 [Cited in Parent U.S. Pat. No. 10,626,137 issued on Apr. 21, 2020].

(56) References Cited

OTHER PUBLICATIONS

Chile Examiner's Report dated Nov. 12, 2018 for Chile Patent Application No. 201603048 [Cited in Parent U.S. Pat. No. 10,626,137 issued on Apr. 21, 2020].
Examination Report No. 1 for Standard patent Application dated Dec. 11, 2018 for Australian Patent Application No. 2015266624 [Cited in Parent U.S. Pat. No. 10,626,137 issued on Apr. 21, 2020].
Invitation to Respond to Written Opinion dated Oct. 5, 2018 for Singapore Patent application No. 11201610004P [Cited in Parent U.S. Pat. No. 10,626,137 issued on Apr. 21, 2020].
First Examiner's Report dated Jun. 21, 2018 for Singapore Patent Application No. 201603048 [Cited in Parent U.S. Pat. No. 10,626,137 issued on Apr. 21, 2020].
Deng, Kai et al., "Synthesis and structure verification of the vaccine adjuvant QS-7-Api. Synthetic access to Homogeneous Quillaja Saponaria Immunostimulants," J. Am. Chem. Soc. 130, pp. 5860-5861, 2008 [Cited in Parent U.S. Pat. No. 10,626,137 issued on Apr. 21, 2020].
Koziorowski, J., et al., "A New Convenient Route to Radioiodinated N-succinimidyl 3- and 4-iodobenzoate, Two Reagents for Radioiodination of proteins," Appl. Radiat. Isot., vol. 49, pp. 955-959, 1998 [Cited in Parent U.S. Pat. No. 10,626,137 issued on Apr. 21, 2020].
Zhi, Yong-Gang et al., "Systematic studies on Photoluminescence of oligo(arylene-ethynylene)s: tunability of excited states and derivatization as luminescent labeling probes for proteins," Eur. J. Org. Chem., pp. 3125-3139, 2006 [Cited in Parent U.S. Pat. No. 10,626,137 issued on Apr. 21, 2020].
Shell, Thomas A., "Selective Targeting of DNA for cleavage within DNA-Histone Assemblies by a Spermine—[CpW (CO)3Ph]2 Conjugate," Org. Biomol. Chem., vol. 3, pp. 3091-3093, 2005 [Cited in Parent U.S. Pat. No. 10,626,137 issued on Apr. 21, 2020].
Berge, Stephen M. et al., "Describe Pharmaceutically Acceptable salts in Detail," J. Pharmaceutical Sciences, vol. 66, pp. 1-19, 1977 [Cited in Parent U.S. Pat. No. 10,626,137 issued on Apr. 21, 2020].
Chilean Examiner's Report dated Jun. 18, 2018 for Chilean Patent Application No. 3048-2016 [Cited in Parent U.S. Pat. No. 10,626,137 issued on Apr. 21, 2020].
Dissertation: "Design and Synthesis of Quillaja Saponin Adjuvants and Synthesis of Lablaboside Saponins," pp. 29-30, Dec. 31, 2013 [Cited in Parent U.S. Pat. No. 10,626,137 issued on Apr. 21, 2020].
Office Action issued on Nov. 28, 2017 for Singapore Patent Application No. 11201610004P [Cited in Parent U.S. Pat. No. 10,626,137 issued on Apr. 21, 2020].
Extended European Search Report issued on Nov. 27, 2017 for European Patent Application No. 15798814.8 [Cited in Parent U.S. Pat. No. 10,626,137 issued on Apr. 21, 2020].
Hani, M. et al., "A Novel Triterpene Saponin from Gypsophila Capillaris," pp. 563-567, Apr. 1, 1995, [Retrieved from the Internet] <https://www.degruyter.com/downloadpdf/j/znb.1995.50.issue-4/znb-1995-0415/znb-1995-0415.pdf> [Cited in Parent U.S. Pat. No. 10,626,137 issued on Apr. 21, 2020].
Luo, Jian-Guang et al., "New Triterpenoid Saponins with Strong *-glucosidase Inhibitory Activity from the Roost of Gypsophila Oldhamiana," Bioorganic & Medicinal Chemistry, vol. 16, pp. 2912-2920, 2008 [Cited in Parent U.S. Pat. No. 10,626,137 issued on Apr. 21, 2020].
Fernandez-Tejada, Alberto et al., "Development of Minimal Saponin Vaccine Adjuvant Based on Qs-21," Nature Chemistry, vol. 6, No. 7, pp. 635-643, Jun. 1, 2014 [Cited in Parent U.S. Pat. No. 10,626,137 issued on Apr. 21, 2020].
Fernandez-Tejada, Alberto et al., "Design, Synthesis, and Immunologic Evaluation of vaccine Adjuvant Conjugates based on QS-21 and Tucaresol," Bioorganic & Medicinal Chemistry, vol. 22, pp. 5917-5923, 2014 [Cited in Parent U.S. Pat. No. 10,626,137 issued on Apr. 21, 2020].
Ma, Li et al., "Triterpenoid Saponins from Dianthus Versicolor," J. Nat. Prod. vol. 72, No. 4, pp. 640-644, Apr. 24, 2009 [Cited in Parent U.S. Pat. No. 10,626,137 issued on Apr. 21, 2020].
Chea, Eric K. et al., "Synethsis and Preclinical Evaluation of Qs-21 Variants Leading to Simplified Vaccine Adjuvants and Mechanistic Probes," J. Am. Chem Soc, vol. 134, No. 32, pp. 13448-13457, Aug. 15, 2012 [Cited in Parent U.S. Pat. No. 10,626,137 issued on Apr. 21, 2020].
Plechanovova, Anna et al., "Novel Substrate-Based Inhibitors of Human Glutamate Carboxypeptidase II with Enhanced Lipophilicity," J Med Chem, vol. 54, No. 21, pp. 7535-7546, Nov. 10, 2011 [Cited in Parent U.S. Pat. No. 10,626,137 issued on Apr. 21, 2020].
McNab, Jennifer A. et al., "Quantitative Short Echo-Time 1H Laser-CSI in Human Brain at 4T," NMR in Biomedicine, vol. 19, pp. 999-1009, 2006 [Cited in Parent U.S. Pat. No. 10,626,137 issued on Apr. 21, 2020].
Elgamal, M. Hani. A et al., Isolation of Triterpene Saponins from Gypsophila Capillaris, Phytochemistry, vol. 38, No. 6, pp. 1481-1485, 1995 [Cited in Parent U.S. Pat. No. 10,626,137 issued on Apr. 21, 2020].
Database Registry, Chemical Abstract Services, STN Accession No. 1596376-86-1, May 2, 2014 [Cited in Parent U.S. Pat. No. 10,626,137 issued on Apr. 21, 2020].
Database Registry, Chemical Abstract Services, STN Accession No. 1424801-42-2, Mar. 18, 2013 [Cited in Parent U.S. Pat. No. 10,626,137 issued on Apr. 21, 2020].
Database Registry, Chemical Abstract Services, STN Accession No. 946617-18-1, Sep. 11, 2007 [Cited in Parent U.S. Pat. No. 10,626,137 issued on Apr. 21, 2020].
Database Registry, Chemical Abstract Services, STN Accession No. 99633-30-4, Jan. 4, 1986 [Cited in Parent U.S. Pat. No. 10,626,137 issued on Apr. 21, 2020].
Database Registry, Chemical Abstract Services, STN Accession No. 57539-70-5 and 30688-36-9, Nov. 16, 1984 [Cited in Parent U.S. Pat. No. 10,626,137 issued on Apr. 21, 2020].
International Search Report and Written Opinion, issued in International Patent Application No. PCT/US15/33567, mailed Aug. 12, 2015. [Cited in Parent U.S. Pat. No. 10,626,137 issued on Apr. 21, 2020].
First Official notification dated Jan. 14, 2021 issued in Israeli Patent Application No. 276674.
Office Action dated Jul. 13, 2021 for Canadian Patent Application No. 2,950,750.
Notification of Reasons for Refusal for Korean Patent Application No. 10-2016-7036860 mailed on Nov. 24, 2021 with English Translation.
European Search Report for European Divisional Patent Application No. 21186590.2 mailed on Oct. 12, 2021.
Notification of Reasons for Refusal for Japanese Patent Application No. 2020-168158 mailed on Dec. 28, 2021.
E. Chea et al., "Synthesis and Preclinical Evaluation of QS-21 Variants Leading to Simplified Vaccine Adjuvants and Mechanistic Probes" J. Am. Chem. Soc., 2012, 134, 13448-13457.
Second Chinese Office Action mailed on Nov. 1, 2023 for Chinese Divisional Patent Application No. 202010932366.0 w/ English translation.
Communication Pursuant to Article 94(3) EPC for European Patent Application No. 21186590.2 mailed on Mar. 27, 2024.

* cited by examiner

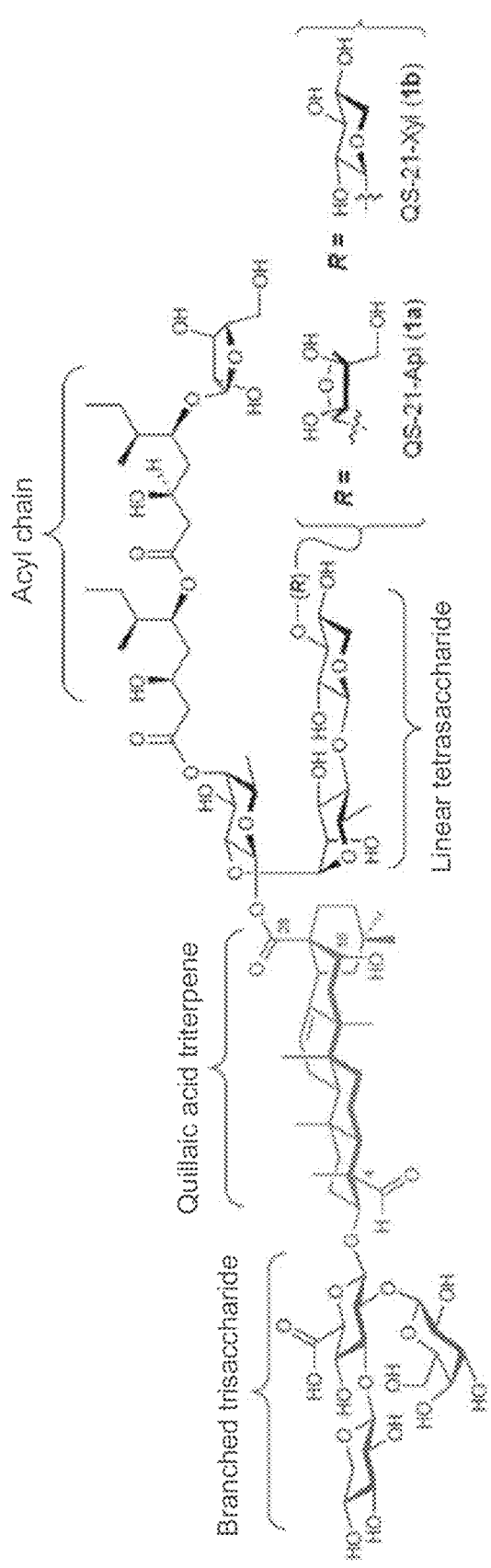
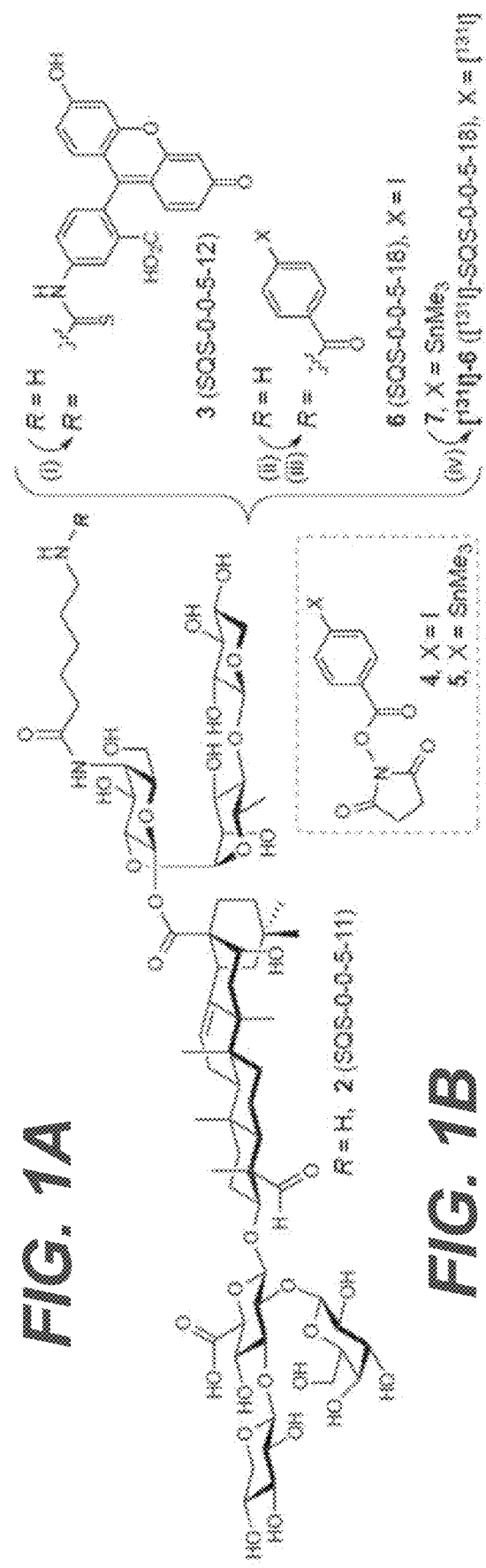
FIG. 1A
FIG. 1B

MINIMAL SAPONIN ANALOGUES, SYNTHESIS AND USE THEREOF

CROSS-REFERENCE TO PRIOR APPLICATIONS

The present application is a continuation of U.S. Non Provisional patent application Ser. No. 16/853,393 filed on Apr. 20, 2020, which will issue as U.S. Pat. No. 11,274,116 on Mar. 15, 2022, which is a continuation of U.S. National Stage patent application Ser. No. 15/314,792 filed on Nov. 29, 2016, which issued as U.S. Pat. No. 10,626,137 on Apr. 21, 2020, which claims priority to International Patent Application No. PCT/US2015/033567 filed on Jun. 1, 2015, which published as WO 2015/184451 on Dec. 3, 2015, which claims priority to U.S. Provisional Patent Application Ser. No. 62/005,302 filed on May 30, 2014. The entire disclosures of these applications are incorporated herein by reference.

STATEMENT REGARDING FEDERALLY FUNDED RESEARCH

This invention was made with government support under grant numbers GM058833, AI085622, and CA008748 awarded by the National Institutes of Health. The government has certain rights in the invention.

FIELD

The present disclosure relates generally to triterpene glycoside saponin derived adjuvants, syntheses thereof, and intermediates thereto. The invention also provides pharmaceutical compositions comprising compounds of the present invention and methods of using said compounds or compositions in the treatment of infectious diseases and cancer.

BACKGROUND

The clinical success of anticancer and antimicrobial vaccines critically depends on the identification of, and access to, novel potent adjuvants with attenuated toxicity. Molecular vaccines comprised of subunit antigens are often less immunogenic than whole pathogens and do not elicit adequate immune responses alone, requiring the inclusion of an immunoadjuvant to increase immunogenicity. Unfortunately, few adjuvants are sufficiently potent and non-toxic for clinical use. In this context, specific fractions from extracts of the bark of *Quillaja saponaria* (QS) have proven to be exceedingly powerful adjuvants in immunotherapy. QS-21, a saponin natural product from the *Quillaja saponaria* tree, is one of the most promising adjuvants currently under investigation (FIG. 1A). It is composed of two isomeric constituents, QS-21-apiose (1a) and QS-21-xylose (FIG. 1B), which differ at the terminal sugar in the linear tetrasaccharide domain. QS-21 has emerged as the immunopotentiator of choice in many recent clinical trials and vaccines containing QS-21 are under development for several cancers and infectious and neurodegenerative diseases (malaria, HIV, hepatitis, tuberculosis, Alzheimer's disease). Despite its promise, QS-21 suffers from several liabilities including limited access from its natural source, toxic side effects, and chemical instability due to spontaneous hydrolysis of the acyl chain. Furthermore, poor understanding of its molecular mechanism of action impedes rational development of analogues with improved efficacy and decreased toxicity.

SUMMARY

One aspect of the present application relates to a minimal saponin analogue having the structure of formula (I),

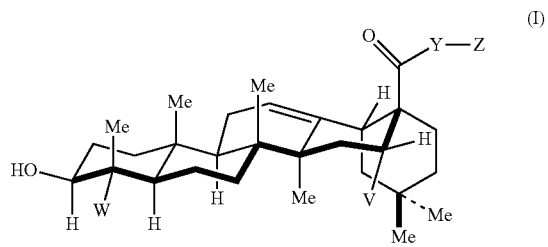

or a pharmaceutically acceptable salt thereof, wherein ⇌ is a single or double bond; W is C(O)R, $CH_2OR$ or $CH_2R$, wherein R is H, or an optionally substituted group selected from acyl, arylalkyl, aryl, heteroaryl, aliphatic, heteroaliphatic, cycloaliphatic and heterocyclyl groups; V is H or OH; Y is O; Z is a linear oligosaccharide or an optionally substituted group selected from the group consisting of amine, amide, acyl, arylalkyl, aryl, heteroaryl, aliphatic, heteroaliphatic, cycloaliphatic and heterocyclyl groups.

Another aspect of the present application relates to a minimal saponin analogue having the structure of formula (II),

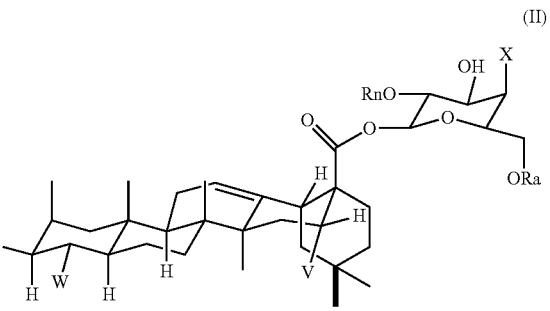

or a pharmaceutically acceptable salt thereof, wherein W is C(O)R, $CH_2OR$ or $CH_2R$, wherein R is H, or an optionally substituted group selected from acyl, arylalkyl, aryl, heteroaryl, aliphatic, heteroaliphatic, cycloaliphatic and heterocyclyl groups; V is H or OH; X is $CH_2R_m$, $C(O)R_m$, $CH_2OR_m$, $CH_2R_m$, $OR_m$, or $NHR_m$, wherein $R_m$ is 11, or an optionally substituted group selected from acyl, arylalkyl, aryl, heteroaryl, aliphatic, heteroaliphatic, cycloaliphatic and heterocyclyl groups, and each occurrence of $R_n$ is independently a hydrogen, a monosaccharide, a disaccharide or a trisaccharide.

Another aspect of the present application relates to a pharmaceutical composition comprising a minimal saponin analogue of the present application, or a pharmaceutically acceptable salt thereof; and an immunologically effective amount of an antigen.

Another aspect of the present application relates to a method for immunizing a subject, comprising administering to the subject the pharmaceutical composition comprising a minimal saponin analogue and an antigen.

Another aspect of the present application relates to a method for immunizing a subject with an antigen, comprising: administering to the subject a vaccine comprising: an effective amount of the antigen; and an effective amount of the compound of formula (I) or a pharmaceutically acceptable salt thereof. In some embodiments, the vaccine is administered orally. In other embodiments, the vaccine is administered intramuscularly. In other embodiments, the vaccine is administered subcutaneously. In certain embodiments, the amount of the compound of formula (I) administered is 10-1000 μg, 500-1000 μg, 100-500 μg, 50-250 μg, 50-500 μg or 250-500 μg.

Another aspect of the present application relates to a pharmaceutical composition, comprising a minimal saponin analogue of the present application, or a pharmaceutically acceptable salt thereof, and an effective amount of a cytotoxic drug.

Another aspect of the present application relates to a method for enhancing the effect of a cytotoxic drug in a subject, comprising administering to the subject the pharmaceutical composition comprising a minimal saponin analogue of the present application and a cytotoxic drug.

Another aspect of the present application relates to a method for enhancing the effect of a cytotoxic drug in a subject, comprising: administering to the subject a pharmaceutical composition comprising: the cytotoxic drug; and an effective amount of the compound of formula (I) or a pharmaceutically acceptable salt thereof.

Another aspect of the present application relates to a kit comprising the minimal saponin analogues of the present application. In some embodiments, the kits comprise prescribing information. In some embodiments, such kits include the combination of an inventive adjuvant compound and another immunotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. In certain embodiments, the kit includes one cycle of immunotherapy. In certain embodiments, the kit includes sufficient quantity of a pharmaceutical composition to immunize a subject against an antigen long term.

Another aspect of the present application relates to a compound of formula (III),

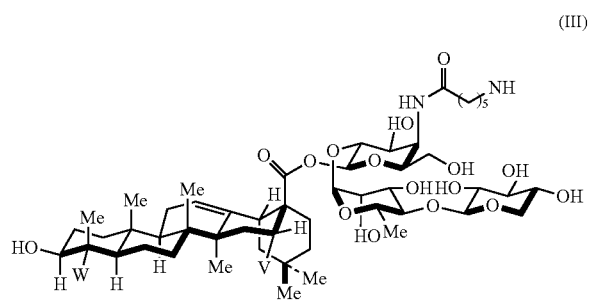

(III)

wherein W is Me, —CHO, or —CH$_2$OH, and V is H or OH

Another aspect of the present application relates to a process for preparing the compound of formula (III).

The accompanying drawings illustrate one or more embodiments of the present disclosure and, together with the written description, serve to explain the principles of the exemplary embodiments of the present disclosure.

BRIEF DESCRIPTION OF THE DRAWINGS

The accompanying drawings illustrate one or more embodiments of the present disclosure and, together with the written description, serve to explain the principles of the exemplary embodiments of the present disclosure.

FIGS. 1A to 1G illustrate aryl iodide saponin 6 exhibits potent adjuvant activity and low toxicity in a preclinical mouse vaccination model. FIG. 1A: Structure of QS-21 and its four key structural domains. FIG. 1B: Synthesis of aryl iodide saponins 6 (SQS-0-0-5-18) and [131I]-6: (i) FITC, Et$_3$N, DMF, 21° C., 2 h, 75%; (ii) 4, Et$_3$N, DMF, 21° C., 1 h, 52%; (iii) 5, Et$_3$N, DMF, 21° C., 1 h, 75%; (iv) [131I]—NaI, Chloramine-T, MeOH, 21° C., 1 min, >50%. FIG. 1C: Structure of adjuvant-attenuated negative control saponin 8 (SQS-0-3-7-18) and synthesis of [131I] 8: (v) [131I]—NaI, Chloramine-T, MeOH, 21° C., 1 min, >50%. FIGS. 1D to 1E: Biological evaluation of aryl iodide saponin 6 (SQS-0-0-5-18) with three-component vaccine for (FIG. 1D) anti-KLH titers (IgG), (FIG. 1E) anti-MUC1 titers (IgG), and (FIG. 1F) anti-OVA titers (IgG) indicating potent adjuvant activity comparable to natural and synthetic QS-21 (compare 20 g doses); horizontal bars indicate median titers; statistical significance compared to no-adjuvant control: *=p≤0.05, =p<0.01, *=p<0.001. (FIG. 1G) Toxicity assessment based on median percent weight loss, indicating low toxicity of 6 (SQS-0-0-5-18); error bars indicate maximum and minimum values for five mice.

FIG. 2A: Biodistribution of active adjuvant [131I]-6 ([131I]-SQS-0-0-5-18) and attenuated adjuvant [131I]-8 ([131I] SQS-0-3-7-18) with OVA antigen, indicating accumulation of [131I]-6, but not [131I]-8, at injection site and lymph nodes; error bars indicate standard deviation from mean for five mice; statistical significance indicated graphically only for lymph nodes and injection site for clarity: *=p<0.05: liver, muscle, lymph node, skin, thyroid; =p<0.01: blood, lungs, spleen, kidneys, bone, injection site; *=p<0.001: heart. FIG. 2B: Imaging at injection site (yellow arrows indicate ink circles) with fluorescein-labeled active adjuvant 3 (SQS-0-0-5-12) or unlabeled inactive adjuvant 2 (SQS-0-0-5-11) and Alexa-647-labeled OVA (OVA-A647), indicating retention of 3 and OVA-A647 at injection site; green crescent in fluorescein image for Mouse 2 is due to software ghosting effect. FIG. 2C: Imaging of dissected lymph nodes with active adjuvant 3 (SQS-0-0-5-12) or inactive adjuvant 2 (SQS-0-0-5-11) and OVA-A647, indicating increased accumulation of OVA-A647 with 3 but not 2. Mice were injected in left flank and right lymph node serves as negative control within each animal.

FIG. 3A Synthesis of aryl iodide saponins 16 (SQS-1-0-5-18) and [$^{131}$I]$^{-16}$, (i) TESOTf, 2,6-lutidine, CH$_2$Cl$_2$, 0° C., 1 h, 80%; (ii) 1. 12, BF3·OEt2, 4 Å M.S., CH$_2$Cl$_2$, −35° C., 30 min; 2. PhSeH, Et$_3$N, 38° C., 8 h, 58% (2 steps); (iii) 1. HO$_2$C(CH$_2$)$_5$NHBoc (14), EtO-COCl, Et$_3$N, THF, 0° C., 2.5 h, (acid preactivation), then add to 13, 0° C., 1.5 h; 2. H2 (50 psi), Pd/C (Degussa), THF/EtOH (1:1), 21° C., 24 h; 3. TFA/H2O (4:1), 0° C., 2 h, 65% (3 steps); (iv) 4, Et$_3$N, DMF, 21° C., 2 h, 67%; (v) 5, Et$_3$N, DMF, 21° C., 1.5 h, 75%; (vi) [131I]—NaI, Chloramine-T, MeOH, 21° C., 1 min, 55%. Biological evaluation of truncated saponin 16 with three-component vaccine for (FIG. 3B) anti-KLH (IgG), (FIG. 3C) anti MUC1 (IgG) and (FIG. 3D) anti-OVA (IgG) titers, indicating potent adjuvant activity; horizontal bars indicate median titers; statistical significance compared to no-adjuvant control: *=p≤0.05, =p<0.01, *=p<0.001. FIG. 3E Toxicity assessment based on median percent weight loss, indicating low toxicity of 16 (SQS-1-0-5-18); error bars indicate maximum and minimum values for five mice.

(FIG. 4D) Toxicity assessment based on median percent weight, indicating low toxicity of 18 (SQS-1-7-5-18); error bars indicate maximum and minimum values for five mice.

FIG. 5A: Structures of saponin adjuvants 19-22 with modifications at the C4-aldehyde substituent and C16-alcohol of the triterpene domain of QS-21. The structure in FIG. 5A is shown with 6-(4-iodobenzoylamino)-hexaynoyl as the acyl chain. Biological evaluation of triterpene variants 19-22 with a four-component vaccine (MUC1-KLH, OVA, GD3 KLH) for (FIG. 5B) anti-KLH (IgG), (FIG. 5C) anti MUC1 (IgG), (FIG. 5D) anti-OVA (IgG), (FIG. 5E) anti-GD3 (IgM), and (FIG. 5F) anti-GD3 (IgG) titers, indicating that the C4-aldehyde substituent is not required adjuvant activity (19, 20) while removal of the C16-alcohol attenuates activity (21, 22); horizontal bars indicate median titers; statistical significance compared to no-adjuvant control: *=p≤0.05, =p<0.01, *=p<0.001. (FIG. 5G) Toxicity assessment based on median percent weight loss, indicating lack of toxicity of 19-22; error bars indicate maximum and minimum values for five mice.

FIG. 7A: Synthesis of negative control saponin 8 (SQS-0-3-7-18): (i) SOCl$_2$, pyridine, CH2Cl2/DMF, 21° C., 2 h, 91%; (ii) 1. H2 (50 psi), Pd/C (Degussa), THF/EtOH (1:1), 21° C., 24 h; 2. TFA/H2O (4:1), 0° C., 3.3 h, RP-HPLC, 50% (2 steps); (iii) 4, Et$_3$N, DMF, 21° C., 3 h, RP-HPLC, 68%; (iv) 5, Et$_3$N, DMF, 21° C., 2.5 h, RP-HPLC, 53%. FIG. 7B: Biological evaluation of aryl iodide saponin 8 with OVA antigen. Mice were vaccinated with OVA (20 μg) according to the general procedure discussed herein. Median titers represented as red horizontal bars. Statistical significance compared to SQS-21 was assessed using two-tailed unpaired Student's t-test with CI=95%: *=0.01≤p≤0.05 (significant).

FIG. 16F: Toxicity assessment of 19-22 based on median percent weight loss over one week after first vaccine injection.

DETAILED DESCRIPTION

Figure 1C:
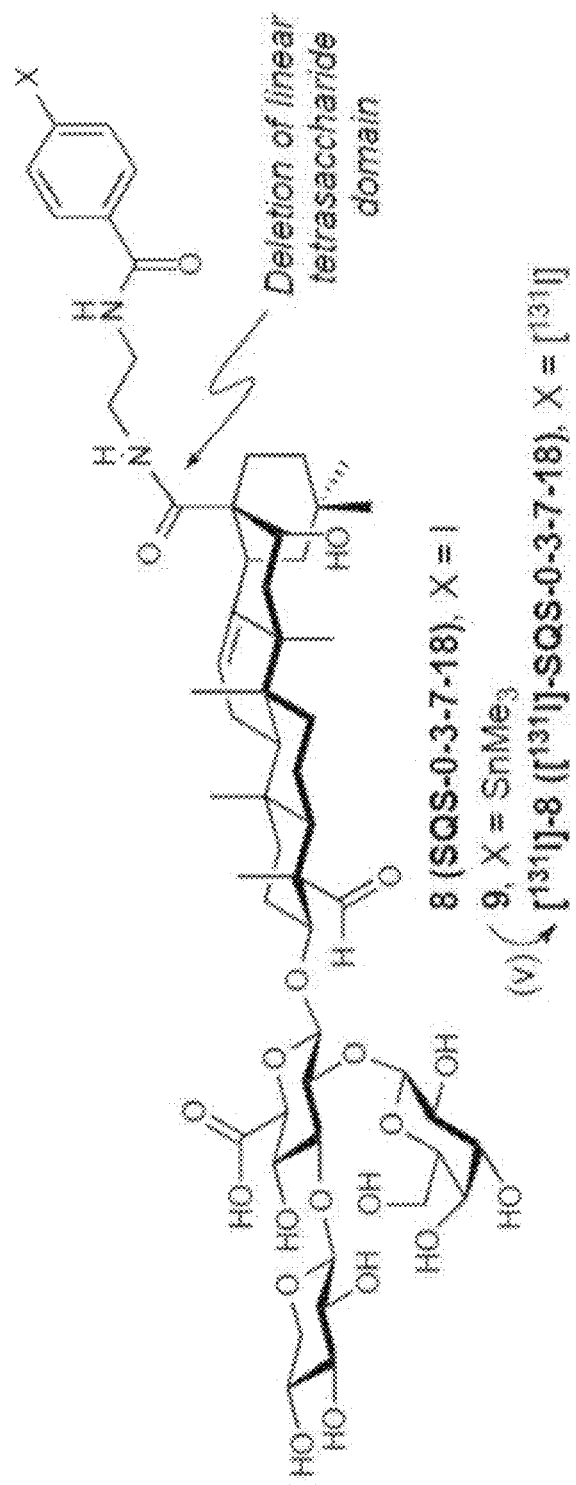

The following detailed description is presented to enable any person skilled in the art to use the present methods and kits. For purposes of explanation, specific nomenclature is set forth to provide a thorough understanding of the present methods and kits. However, it will be apparent to one skilled in the art that these specific details are not required to practice the use of the methods and kits. Descriptions of specific applications are provided only as representative examples. The present methods and kits are not intended to be limited to the embodiments shown, but are to be accorded the widest possible scope consistent with the principles and features disclosed herein.

Headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

Definitions

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a Cia straight or branched alkyl group. Exemplary lower alkyl groups are methyl, ethyl, propyl, isopropyl, butyl, isobutyl, and tertbutyl.

The term "lower haloalkyl" refers to a Cia straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-12}$ (or $C_{1-26}$, $C_{1-16}$, $C_{1-8}$) or saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group. A substituted alkynylene chain is a polymethylene group containing at least one double bond in which one or more hydrogen atoms are replaced with a substituent. Suitable substituents include those described below for a substituted aliphatic group.

The term "acyl," used alone or a part of a larger moiety, refers to groups formed by removing a hydroxy group from a carboxylic acid.

The term "halogen" means F, Cl, Br, or I.

The terms "aralkyl" and "arylalkyl" are used interchangeably and refer to alkyl groups in which a hydrogen atom has been replaced with an aryl group. Such groups include, without limitation, benzyl, cinnamyl, and dihyrocinnamyl.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 n electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted.

The term "heteroaliphatic," as used herein, means aliphatic groups wherein one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In other cases, the compounds of the present invention may contain one or more acidic functional groups and, thus, are capable of forming pharmaceutically-acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary, tertiary, or quaternary amine. Salts derived from appropriate bases include alkali metal, alkaline earth metal, ammonium and $N^+C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Representative organic amines useful for the formation of base addition salts include ethylamine, diethylamine, ethylenediamine, ethanolamine, diethanolamine, piperazine and the like. (See, for example, Berge et al., supra).

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Provided compounds may comprise one or more saccharide moieties. Unless otherwise specified, both D- and L-configurations, and mixtures thereof, are within the scope of the invention. Unless otherwise specified, both α- and β-linked embodiments, and mixtures thereof, are contemplated by the present invention.

If, for instance, a particular enantiomer of a compound of the present invention is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

As used herein, the term "reducing agent" refers to a reagent suitable for carrying out the contextually relevant reduction reaction. Exemplary, but non-limiting, reducing agents are: lithium aluminum hydride (LiAlH4), sodium borohydride (NaBH4), hydroboration reagents (BH3, B2H6), alkali metals (e.g. Li or Na), transition metals (e.g. Sn, Zn, or Fe), Grignard reagents (RMgX), and organometallics (Rli, RNa, R2CuLi). The term may also encompass reductive techniques such as catalytic hydrogenation. One of ordinary skill in the art will appreciate that the synthetic methods, as described herein, utilize a variety of reducing agents.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably nontoxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), f-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, I-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazole-1-yl) bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (JPDMS), diethylisopropylsilyl (DEIPS), dimethyltheylsilyl, t-butyldimethylsilyl (TBDMS), 1-butyldiphenylsilyl (TBDPS), tribenzylsilyl, tri-p-xylylsilyl, triphenylsilyl, diphenylmethylsilyl (DPMS), 1-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, 1-butyl carbamate (BOC), I-adamantyl carbamate (Adoc), vinyl carbamate (Voe), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl) methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N—S-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-itrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}$ R°; —$(CH_2)_{0-4}$ OR°; —O$(CH_2)_{0-4}$ R°, —O—$(CH_2)_{0-4}$ C(O)OR°; —$(CH_2)_{0-4}$ CH(OR°)$_2$; —$(CH_2)_{0-4}$ SR°; —$(CH_2)_{0-4}$ Ph, which may be substituted with R°; —$(CH_2)_{0-4}$ O$(CH_2)_{0-1}$ Ph which may be substituted with R°; —CH=CHPh, which may be substituted with R°; —$(CH_2)_{0-4}$ O$(CH_2)_{0-1}$-pyridyl which may be substituted with R°; —$NO_2$; —CN; —$N_3$; —$(CH_2)_{0-4}$ N(R°)$_2$; —$(CH_2)_{0-4}$N(R°)C(O)R°; —N(R°)C(S)R°; —$(CH_2)_{0-4}$ N(R°)C(O)NR°$_2$; —N(R°)C(S)NR°$_2$; —$(CH_2)_{0-4}$ N(R°)C(O)OR°; —N(R°)N(R°)C(O)R°; —N(R°)N(R°)C(O)NR°$_2$; —N(R°)N(R°)C(O)OR°; —$(CH_2)_{0-4}$ C(O)R°; —C(S)R°; —$(CH_2)_{0-4}$ C(O)OR°; —$(CH_2)_{0-4}$ C(O)SR°; —$(CH_2)_{0-4}$ C(O)OSiR°$_3$; —$(CH_2)_{0-4}$ OC(O)R°; —OC(O)$(CH_2)_{0-4}$ SR°—, SC(S)SR°; —$(CH_2)_{0-4}$ SC(O)R°; —$(CH_2)_{0-4}$ C(O)NR°$_2$; —C(S)NR°$_2$; —C(S)SR°; —SC(S)SR°, —$(CH_2)_{0-4}$ OC(O)NR°$_2$; —C(O)N(OR°)R°; —C(O)C(O)R°; —C(O)CH$_2$C(Q)R°; —C(NOR°)R°; —$(CH_2)_{0-4}$ SSR°; —$(CH_2)_{0-4}$ S(O)$_2$R°; —$(CH_2)_{0-4}$ S(O)$_2$OR°; —$(CH_2)_{0-4}$ OS(O)$_2$R°; —S(O)$_2$NR°$_2$; —$(CH_2)_{0-4}$ S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —($C_{1-4}$ straight or branched alkylene)O—N(R°)$_2$; or —($C_{1-4}$ straight or branched alkylene)C(O)ON(R°)$_2$, wherein each R° may be substituted as defined below and is independently hydrogen, C$_{1-6}$ aliphatic, —CH$_2$Ph, —O(CH$_2$)$_{0-1}$ Ph, —CH$_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$ R$^\bullet$, -(haloR$^\bullet$), —(CH$_2$)$_{0-2}$ OH, —(CH$_2$)$_{0-2}$ OR$^\bullet$, —(CH$_2$)$_{0-2}$ CH(OR$^\bullet$)$_2$; —O(haloR$^\bullet$), —CN, —N$_3$, —(CH$_2$)$_{0-2}$ C(O)R$^\bullet$, —(CH$_2$)$_{0-2}$ C(O)OH, —(CH$_2$)$_{0-2}$ C(O)OR, —(CH$_2$)$_{0-2}$ SR$^\bullet$, —(CH$_2$)$_{0-2}$ SH, —(CH$_2$)$_{0-2}$ NH$_2$, —(CH$_2$)$_{0-2}$NHR$^\bullet$, —(CH$_2$)$_{0-2}$ NR°$_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$ Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*)$_2$)$_{2-3}$ O—, or —S(C(R*))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*)$_{2-3}$ O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$ Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$—NR$^\dagger_2$, —C(O)R$^\dagger$, —C(O)OR$^\dagger$, —C(O)C(O)R$^\dagger$. —C(O)CH$_2$C(O)R$^\dagger$, —S(O)$_2$R$^\dagger$—S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$ Ph, or a 5-6-membered saturated, partially unsaturated, or aryl ring having 0-4 heteroatoms independently selected from nitrogen, oxygen, or sulfur.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "enriched" as used herein refers to a mixture having an increased proportion of one or more species. In some embodiments, the mixture is "enriched" following a process that increases the proportion of one or more desired species in the mixture. In some embodiments, the desired species comprise(s) greater than 10% of the mixture. In some embodiments, the desired species comprise(s) greater than 25% of the mixture. In some embodiments, the desired species comprise(s) greater than 40% of the mixture. In some embodiments, the desired species comprise(s) greater than 60% of the mixture. In some embodiments, the desired species comprise(s) greater than 75% of the mixture. In some embodiments, the desired species comprise(s) greater than 85% of the mixture. In some embodiments, the desired species comprise(s) greater than 90% of the mixture. In some embodiments, the desired species comprise(s) greater than 95% of the mixture. Such proportions can be measured any number of ways, for example, as a molar ratio, volume to volume, or weight to weight.

The term "pure" refers to compounds that are substantially free of compounds of related non-target structure or chemical precursors (when chemically synthetized). This quality may be measured or expressed as "purity." In some embodiments, a target compound has less than about 30%, 20%, 10%, 5%, 2%, 1%, 0.5%, and 0.1% of non-target structures or chemical precursors. In certain embodiments, a pure compound of present invention is only one prosapogenin compound (i.e., separation of target prosapogenin from other prosapogenins).

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula C$_n$H$_{2n}$O$_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

Minimal Saponin Analogues

One aspect of the present application relates to minimal saponin analogues (also referred to as "truncated saponins") that do not contain the branched trisaccharide domain of the standard saponin molecule. In one embodiment, the minimal saponin analogue is a compound having the chemical structure of formula (I),

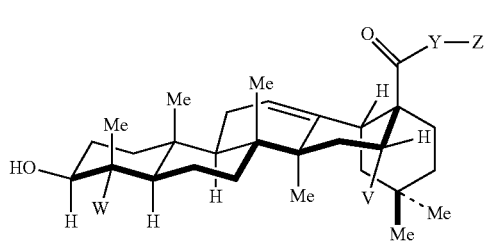

or a pharmaceutically acceptable salt thereof, wherein
 is a single or double bond;
W is methyl, —CHO, —CH2OR$^x$, or —C(O)R$^y$;
V is hydrogen or —OR$^x$;
Y is CH$_2$, —O—, —NR—, or —NH—;
wherein R is hydrogen, an optionally substituted group selected from acyl, arylalkyl, 6-10 membered aryl, C1-12 aliphatic or C1-C12 heteroaliphatic;
Z is hydrogen, a cyclic or acyclic, optionally substituted moiety selected from the group consisting of acyl, aliphatic, heteroaliphatic, aryl, arylalkyl, heterocyclyl, and heteroaryl; or Z comprises a carbohydrate;
each occurrence of R$^x$ is independently hydrogen or an oxygen protecting group selected from the group consisting of alkyl ethers, benzyl ethers, silyl ethers, acetals, ketals, esters, carbamates, and carbonates;
R$^y$ is —OH, —OR, or a carboxyl protecting group, wherein the carboxyl protecting group when taken with its attached carbonyl group, is an ester, amide, or hydrazide.

In some embodiments, W is methyl, —CHO or —CH$_2$OH. In other embodiments, V is H or OH. In other embodiments, W is methyl, —CHO or —CH$_2$OH and V is H or OH. In other embodiments, W is methyl and V is OH. In other embodiments, W is CH$_2$OH and V is OH. W is CHO and V is OH.

In some embodiments, the minimal saponin analogue having the structure of formula (I), wherein  is a single or double bond; W is C(O)R, CH$_2$OR or CH$_2$R, wherein R is H, or an optionally substituted group selected from acyl, arylalkyl, aryl, heteroaryl, aliphatic, heteroaliphatic, cycloaliphatic and heterocyclyl groups; V is H or OH; Y is O; Z is a linear oligosaccharide or an optionally substituted group selected from the group consisting of amine, amide, acyl, arylalkyl, aryl, heteroaryl, aliphatic, heteroaliphatic, cycloaliphatic and heterocyclyl groups.

Another aspect of the present application relates to a minimal saponin analogue having the structure of formula (II),

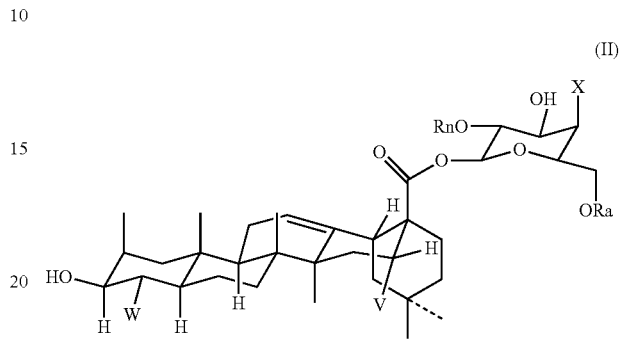

or a pharmaceutically acceptable salt thereof, wherein W is C(O)R, CH$_2$OR or CH$_2$R, wherein R is H, or an optionally substituted group selected from acyl, arylalkyl, aryl, heteroaryl, aliphatic, heteroaliphatic, cycloaliphatic and heterocyclyl groups; V is H or OH; X is CH$_2$R$_m$, C(O)R$_m$, CH$_2$OR$_m$, CH$_2$R$_m$, OR$_m$, or NHR$_m$, wherein R$_m$ is H, or an optionally substituted group selected from acyl, arylalkyl, aryl, heteroaryl, aliphatic, heteroaliphatic, cycloaliphatic and heterocyclyl groups, and each occurrence of R$_n$ is independently a hydrogen, a monosaccharide, a disaccharide or a trisaccharide.

In some embodiments, the minimal saponin analogue of the present application is produced from a precursor having the structure of formula (III)

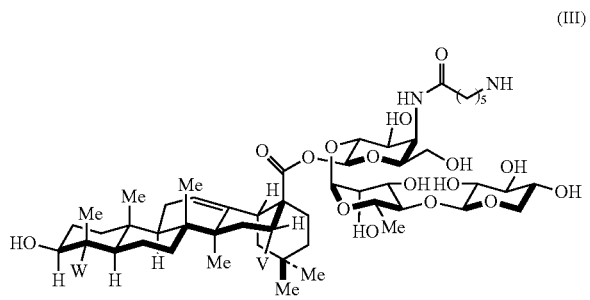

wherein: W is Me, —CHO, or —CH$_2$OH, and V is H or OH.

Method of Synthesis

Another aspect of the present application relates to a process for preparing the minimal saponin analogues of the present application. In some embodiments, the process includes the production of the precursor having the structure of formula (III). In some embodiments, the precursor of formula (III) is produced with the following steps:
a) reacting a compound of formula (100) with a protecting group to form a compound of formula (101), wherein W is Me, CHO, CH$_2$OH, or CH$_2$OR$_p$; wherein R$_p$ is H or a suitable protecting group as necessary to achieve regioselectivity; V is H or OR$_p$, and TES is a triethylsilyl protecting group;

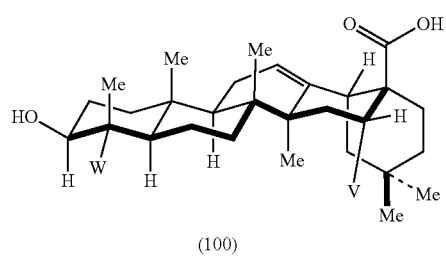
(100)
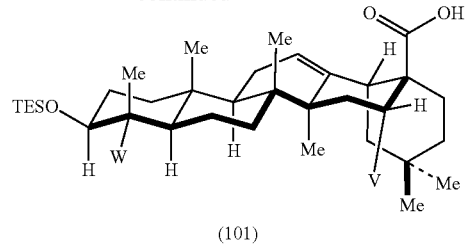
(101)
b) reacting the compound of formula (101) with the compound of formula (102) to form the compound of formula (103), wherein Bn is a benzyl protecting group;
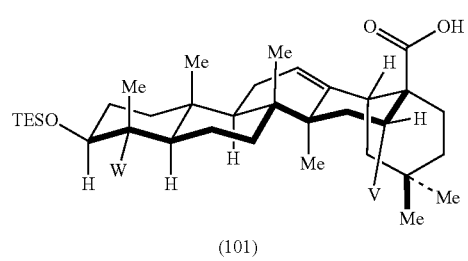
(101)
+
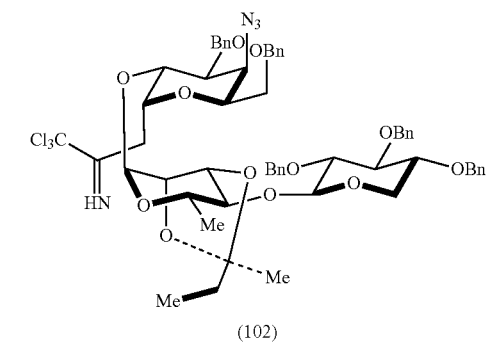
(102)
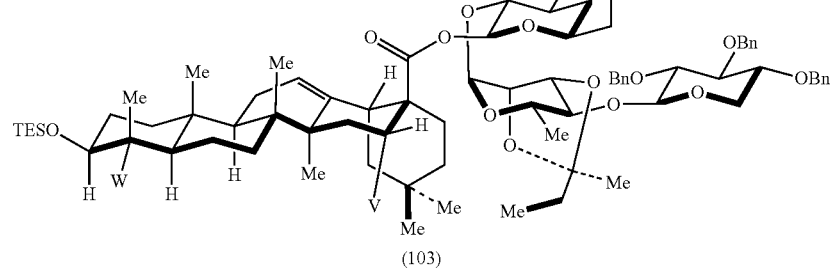
(103)
c) reacting the compound of formula (103) with a reducing agent to form the compound of formula (104);
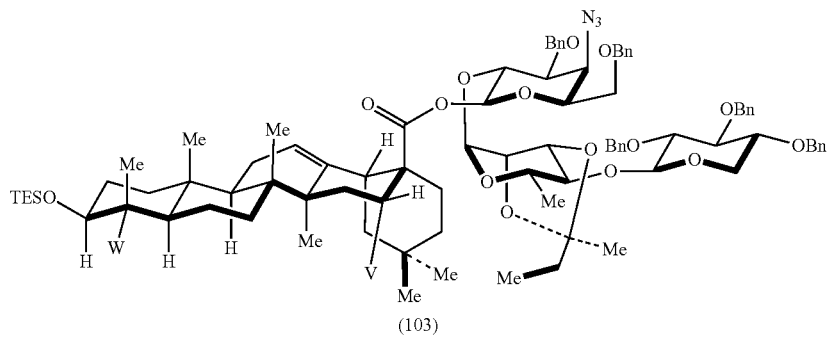
(103)

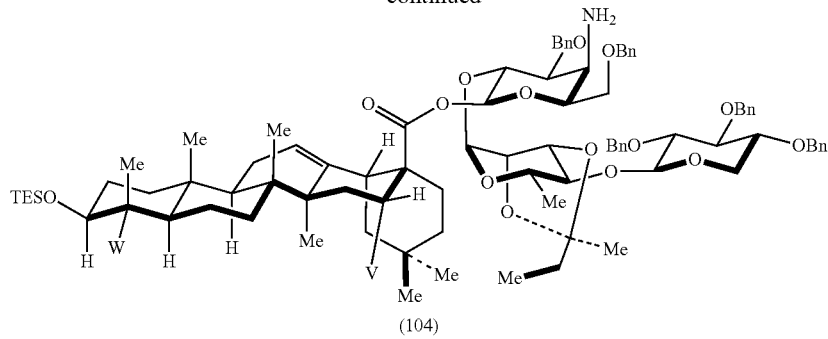

(104)

d) coupling the compound of formula (104) with compound of formula (105) in the presence of an activating agent to form the compound of formula (106), wherein Boc is a tertbutyloxycarbonyl protecting group;

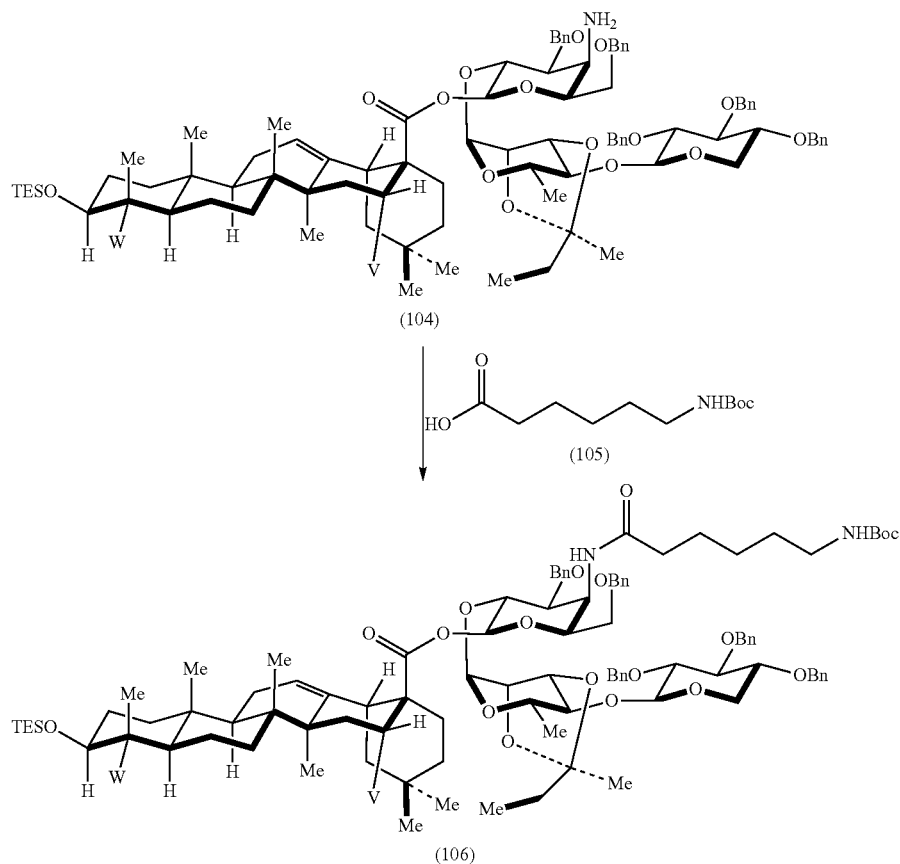

e) deprotecting the compound of formula (106) to form the compound of formula (III).

In some embodiments, the protecting group is selected from the group consisting of methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), i-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, I-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl. α-naphthyldiphenylmethyl, p-methoxyphenyldiphenylmethyl, di(p-methoxyphenyl) phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazole-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In another embodiment, the process wherein the oxygen protecting group is triethylsilyl (TES). In another embodiment, the process wherein the reducing reagent is phenyl selenol.

In certain embodiments, the minimal saponin analogues have a purity of 80% or greater, 85% or greater, 90% or greater, 95% or greater, 96% or greater, 97% or greater, 98% or greater, 99% or greater.

Vaccine Composition

Another aspect of the present application relates to a vaccine composition comprising an antigen and the minimal saponin analogue of the present application as an adjuvant. In some embodiments, the vaccine composition further comprises additional adjuvants.

The vaccine compositions of the present application are useful as vaccines to induce active immunity towards antigens in subjects. Any animal that may experience the beneficial effects of the compositions of the present invention within the scope of subjects that may be treated. In some embodiments, the subjects are mammals. In some embodiments, the subjects are humans.

Most protein and glycoprotein antigens are poorly immunogenic or non-immunogenic when administered alone. Strong adaptive immune responses to such antigens often requires the use of adjuvants. Immune adjuvants are substances that, when administered to a subject, increase the immune response to an antigen or enhance certain activities of cells from the immune system. An adjuvant may also allow the use of a lower dose of antigen to achieve a useful immune response in a subject.

Common adjuvants include alum, Freund's adjuvant (an oil-in-water emulsion with dead mycobacteria), Freund's adjuvant with MDP (an oil-in-water emulsion with muramyldipeptide, MDP, a constituent of mycobacteria), alum plus *Bordetella pertussis* (aluminum hydroxide gel with killed *B. pertussis*). Such adjuvants are thought to act by delaying the release of antigens and enhancing uptake by macrophages. Immune stimulatory complexes (ISCOMs) such as Quil-A (a *Quillaja* saponin extract) are open cage-like complexes typically with a diameter of about 40 nm that are built up by cholesterol, lipid, immunogen, and saponin. ISCOMs deliver antigen to the cytosol, and have been demonstrated to promote antibody response and induction of T helper cell as well as cytotoxic T lymphocyte responses in a variety of experimental animal models.

The vaccines of the present invention may be used to confer resistance to infection or cancer by either passive or active immunization. When the vaccines of the present invention are used to confer resistance through active immunization, a vaccine of the present invention is administered to an animal to elicit a protective immune response which either prevents or attenuates a proliferative or infectious disease. When the vaccines of the present invention are used to confer resistance to infection through passive immunization, the vaccine is provided to a host animal (e.g., human, dog, or mouse), and the antisera elicited by this vaccine is recovered and directly provided to a recipient suspected of having an infection or disease or exposed to a causative organism.

The present invention thus concerns and provides a means for preventing or attenuating a proliferative disease resulting from organisms or tumor cells which have antigens that are recognized and bound by antisera produced in response to the immunogenic polypeptides included in vaccines of the present invention. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the vaccine(s) are provided in advance of any symptoms of proliferative disease. The prophylactic administration of the vaccine(s) serves to prevent or attenuate any subsequent presentation of the disease. When provided therapeutically, the vaccine(s) is provided upon or after the detection of symptoms which indicate that an animal may be infected with a pathogen or have a certain cancer. The therapeutic administration of the vaccine(s) serves to attenuate any actual disease presentation. Thus, the vaccines may be provided either prior to the onset of disease proliferation (so as to prevent or attenuate an anticipated infection or cancer) or after the initiation of an actual proliferation.

Thus, in one aspect the present invention provides vaccines comprising one or more bacterial, viral, protozoal, or tumor-related antigens in combination with one or more inventive compounds. In some embodiments, the vaccine comprises a single bacterial, viral, protozoal, or tumor-related antigen in combination with one inventive compound. In some embodiments, the vaccine comprises two or more bacterial, viral, protozoal, or tumor-related antigens in combination with a single inventive compound. In some embodiments, the vaccine comprises a two or more bacterial, viral, protozoal, or tumor-related antigens in combination with two or more inventive compounds. In some embodiments, the vaccine comprises a single bacterial, viral, protozoal, or tumor-related antigens in combination with two or more inventive compounds.

In some embodiments, one or more antigens of provided vaccines are bacterial antigens. In certain embodiments, the bacterial antigens are antigens associated with a bacterium selected from the group consisting of Helicobacter pylori, Chlamydia pneumoniae, Chlamydia trachomatis, Ureaplasma urealyticum, Mycoplasma pneumoniae, Staphylococcus spp., Staphylococcus aureus, Streptococcus spp., Streptococcus pyogenes, Streptococcus pneumoniae, Streptococcus viridans, Enterococcus faecalis, Neisseria meningitidis, Neisseria gonorrhoeae, Bacillus anthracis, Salmonella spp., Salmonella typhi, Vibrio cholera, Pasteurella pestis, Pseudomonas aeruginosa, Campylobacter spp., Campylobacter jejuni, Clostridium spp., Clostridium difficile, Mycobacterium spp., Mycobacterium tuberculosis, Treponema spp., Borrelia spp., Borrelia burgdorferi, Leptospria spp., Hemophilus ducreyi, Corynebacterium diphtheria, Bordetella pertussis, Bordetella parapertussis, Bordetella bronchiseptica, Hemophilus influenza, Escherichia coli, Shigella spp., Erlichia spp., Rickettsia spp. and combinations thereof.

In certain embodiments, one or more antigens of provided vaccines are viral-associated antigens. In certain embodiments, the viral-associated antigens are antigens associated with a virus selected from the group consisting of influenza viruses, parainfluenza viruses, mumps virus, adenoviruses, respiratory syncytial virus, Epstein-Barr virus, rhinoviruses, polioviruses, coxsackieviruses, echo viruses, rubeola virus, rubella virus, varicella-zoster virus, herpes viruses, herpes simplex virus, parvoviruses, cytomegalovirus, hepatitis viruses, human papillomavirus, alphaviruses, flaviviruses, bunyaviruses, rabies virus, arenaviruses, filoviruses, HIV 1, HIV 2, HTLV-1, HTLV-II, FeLV, bovine LV, FeIV, canine distemper virus, canine contagious hepatitis virus, feline calicivirus, feline rhinotracheitis virus, TGE virus, foot and mouth disease virus, and combinations thereof.

In certain embodiments, one or more antigens of provided vaccines are tumor-associated antigens. In some embodiments, the tumor-associated antigens are antigens selected from the group consisting of killed tumor cells and lysates thereof, MAGE-1, MAGE-3 and peptide fragments thereof; human chorionic gonadotropin and peptide fragments thereof; carcinoembryonic antigen and peptide fragments thereof, alpha fetoprotein and peptide fragments thereof; pancreatic oncofetal antigen and peptide fragments thereof; MUC-1 and peptide fragments thereof, CA 125, CA 15-3, CA 19-9, CA 549, CA 195 and peptide fragments thereof; prostate-specific antigens and peptide fragments thereof; prostate-specific membrane antigen and peptide fragments thereof; squamous cell carcinoma antigen and peptide fragments thereof; ovarian cancer antigen and peptide fragments thereof; pancreas cancer associated antigen and peptide fragments thereof; Her1/neu and peptide fragments thereof; gp-100 and peptide fragments thereof; mutant K-ras proteins and peptide fragments thereof, mutant p53 and peptide fragments thereof; truncated epidermal growth factor receptor, chimeric protein p210$^{BCR\text{-}ABL}$, KH-1, N3, GM1, GM2, GD2, GD3, Gb3, Globo-H, STn, Tn, Lewis$^x$, Lewis$^y$, TF; and mixtures thereof.

In certain embodiments, an antigen is covalently bound to a compound of formula (I). In some embodiments, an antigen is not covalently bound to a compound of formula (I).

One of ordinary skill in the art will appreciate that vaccines may optionally include a pharmaceutically acceptable excipient or carrier. Thus, according to another aspect, provided vaccines comprise one or more antigens that are optionally conjugated to a pharmaceutically acceptable excipient or carrier. In some embodiments, said one or more antigens are conjugated covalently to a pharmaceutically acceptable excipient. In other embodiments, said one or more antigens are non-covalently associated with a pharmaceutically acceptable excipient.

As described above, adjuvants may be used to increase the immune response to an antigen. According to the invention, provided vaccines may be used invoke an immune response when administered to a subject. In certain embodiments, an immune response to an antigen may be potentiated by administering to a subject a provided vaccine in an effect amount to potentiate the immune response of said subject to said antigen.

As described above, provided compounds may be used in cancer vaccines as adjuvants in combination with tumor-associated antigens. In certain embodiments, said vaccines may be used in the treatment or prevention of neoplasms. In certain embodiments, the neoplasm is a benign neoplasm. In other embodiments, the neoplasm is a malignant neoplasm. Any cancer may be treated using compounds of the invention with an antigen.

In certain embodiments, the malignancy is a hematological malignancy. Hematological malignancies are types of cancers that affect the blood, bone marrow, and/or lymph nodes. Examples of hematological malignancies that may be treated using compounds of formula (I) include, but are not limited to, acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), Mantle cell lymphoma, B-cell lymphoma, acute lymphoblastic T-cell leukemia (T-ALL), acute promyelocytic leukemia, and multiple myeloma.

Other cancers besides hematological malignancies may also be treated using compounds of formula (I). In certain embodiments, the cancer is a solid tumor. Exemplary cancers that may be treated using compounds of formula (I) include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, gallbladder cancer, laryngeal cancer, oral cancer, penile cancer, glandular tumors, rectal cancer, small intestine cancer, sarcoma, carcinoma, melanoma, urethral cancer, vaginal cancer, to name but a few.

In certain embodiments, compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another antiproliferative agent), or they may achieve different effects (e.g., control of any adverse effects).

For example, other therapies or anticancer agents that may be used in combination with the inventive anticancer agents of the present invention include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see, www.nci.nih.gov, a list of the FDA approved oncology drugs at www.fda.gov/cder/cancer/druglistframe.htm, and The Merck Manual, Seventeenth Ed. 1999, the entire contents of which are hereby incorporated by reference.

Another aspect of the present application relates to a methods for immunizing a subject with the vaccine composition of the present application.

Method for Enhancing the Effect of Other Drugs

Another aspect of the present application relates to methods for enhancing the effect of a cytotoxic drug, such as an anti-cancer drug, with a minimal saponin analogue of formula (I) or a salt thereof. Examples of the cytotoxic drugs include, but are not limited to, anti-cancer agents may include alkylating agents, such as bendamustine, busulfan, carmustine, chlorambucil, cyclophosphamide, dacarbazine, ifosfamide, melphalan, procarbazine, streptozocin, temozolomide; anti-tumor antibiotics, such as actinomycin D/dactinomycin, bleomycin, daunorubicin, doxorubicin, doxorubicin (pegylated liposomal), epirubicin, idarubicin, mitomycin, mitoxantrone; plant alkaloids/microtubule inhibitors, such as etoposide, docetaxel, irinotecan, paclitaxel, topotecan, vinblastine, vincristine, vinorelbine; antimetabolites, such as asparaginase, capecitabine, cytarabine, 5-fluoro uracil, fludarabine, gemcitabine, methotrexate, pemetrexed, raltitrexed; DNA linking agents, such as carboplatin, cisplatin, oxaliplatin; bisphosphonates, such as clodronate, ibandronic acid, pamidronate, zolendronic acid; biological agents, such as alemtuzamab, BCG, bevacizumab, cetuximab, denosumab, erlotinib, gefitinib, imatinib, interferon, ipilimumab, lapatinib, panitumumab, rituximab, sunitinib, sorafenib, temsirolimus, trastuzumab; hormones/other, such as anastrozole, abiraterone, amifostine, bexarotene, bicalutamide, buserelin, cyproterone, degarelix, exemestane, flutamide, folinic acid, fulvestrant, goserelin, lanreotide, lenalidomide, letrozole, leuprorelin, medroxyprogesterone, megestrol, mesna, octreotide, stilboestrol, tamoxifen, thalidomide, triptorelin.

Another aspect of the present application relates to a pharmaceutical composition comprising an effective amount of a minimal saponin analogue of formula (I) or a salt thereof, and a cytotoxic drug.

Method of Treatment

Another aspect of the present application relates a method of treating infectious disease in a subject comprising administering to the subject a therapeutically effective amount of a compound of formula (I). In some embodiments, the infection is bacterial. In some embodiments, the infection is viral. In some embodiments, the infection is protozoal. In some embodiments, the subject is human.

Another aspect of the present application relates to a pharmaceutical composition comprising an effective amount of a minimal saponin analogue of formula (I) or a salt thereof, and a pharmaceutically acceptable carrier.

Formulations

The minimal saponin analogues of the present application may be combined with a pharmaceutically acceptable excipient to form a pharmaceutical composition. In certain embodiments, the pharmaceutical composition includes a pharmaceutically acceptable amount of an inventive compound. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Liquid dosage forms for oral administration of the compounds of the invention include pharmaceutically acceptable emulsions, micro emulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

In certain embodiments, a compound or pharmaceutical preparation is administered orally. In other embodiments, the compound or pharmaceutical preparation is administered intravenously. Alternative routes of administration include sublingual, intramuscular, and transdermal administrations.

The preparations of the present application may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The minimal saponin analogues of the present application may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the minimal saponin analogues of the present application, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the application is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

In some embodiments, provided adjuvant compounds are administered as pharmaceutical compositions or vaccines. In certain embodiments, the amount of adjuvant compound administered is 1-2000 µg. In certain embodiments, the amount of adjuvant compound administered is 1-1000 µg. In certain embodiments, the amount of adjuvant compound administered is 1-500 µg. In certain embodiments, the amount of adjuvant compound administered is 1-250 µg. In certain embodiments, the amount of adjuvant compound administered is 100-1000 µg. In certain embodiments, the amount of adjuvant compound administered is 100-500 µg. In certain embodiments, the amount of adjuvant compound administered is 100-200 µg. In certain embodiments, the amount of adjuvant compound administered is 250-500 µg. In certain embodiments, the amount of adjuvant compound administered is 10-1000 µg. In certain embodiments, the amount of adjuvant compound administered is 500-1000 µg. In certain embodiments, the amount of adjuvant compound administered is 50-250 µg. In certain embodiments, the amount of adjuvant compound administered is 50-500 µg.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, in certain embodiments the compound is administered as a pharmaceutical formulation (composition) as described above.

The compounds according to the invention may be formulated for administration in any convenient way for use in human or veterinary medicine, by analogy with other pharmaceuticals.

The invention provides kits comprising pharmaceutical compositions of an inventive compound. In certain embodiments, such kits including the combination of a compound of formula (I) and an antigen. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. The kit may include a full cycle of immunotherapy. In some embodiments, the kit includes a vaccine comprising one or more bacterial, viral, protozoal, or tumor-associated antigens, and one or more provided compounds.

The entire contents of all references cited above and herein are hereby incorporated by reference.

The description herein is for the purpose of teaching the person of ordinary skill in the art how to practice the present disclosure, and it is not intended to detail all those obvious modifications and variations of it which will become apparent to the skilled worker upon reading the description. The specific embodiments of the present application have been presented for purposes of illustration and description. They are not intended to be exhaustive or to limit the application and method of use to the precise forms disclosed. Obviously many modifications and variations are possible in light of the above teaching. It is understood that various omissions or substitutions of equivalents are contemplated as circumstance may suggest or render expedient, but is intended to cover the application or implementation without departing from the spirit or scope of the claims of the present application.

EXAMPLES

Example 1: Initial Evaluation of Iodinated Saponius 6 and 8

A radioiodine ($^{131}$I) was introduced into the QS-21 saponin scaffold to enable in vivo biodistribution studies. The non-radiolabeled aryl iodide 6 (SQS-0-0-5-18) by acylation of amine 2 (SQS-0-0-5-11) was synthesized (FIG. 1B). Because no in vitro model exists to assess adjuvant activity, biological evaluation of aryl iodide 6 was carried out in a preclinical mouse vaccination model involving a multi-antigen formulation comprised of the immunogenic peptide MUC1 (prostate and breast cancer antigen, non-glycosylated tandem repeat) conjugated to the highly immunogenic KLH carrier protein (MUC1-KLH) and OVA, a reliable immunogen that induces both antibody and T-cell responses in mice. Antibody responses against each of the three antigens, co-administered with the adjuvant of interest, were determined by ELISA.

Figure 1D:
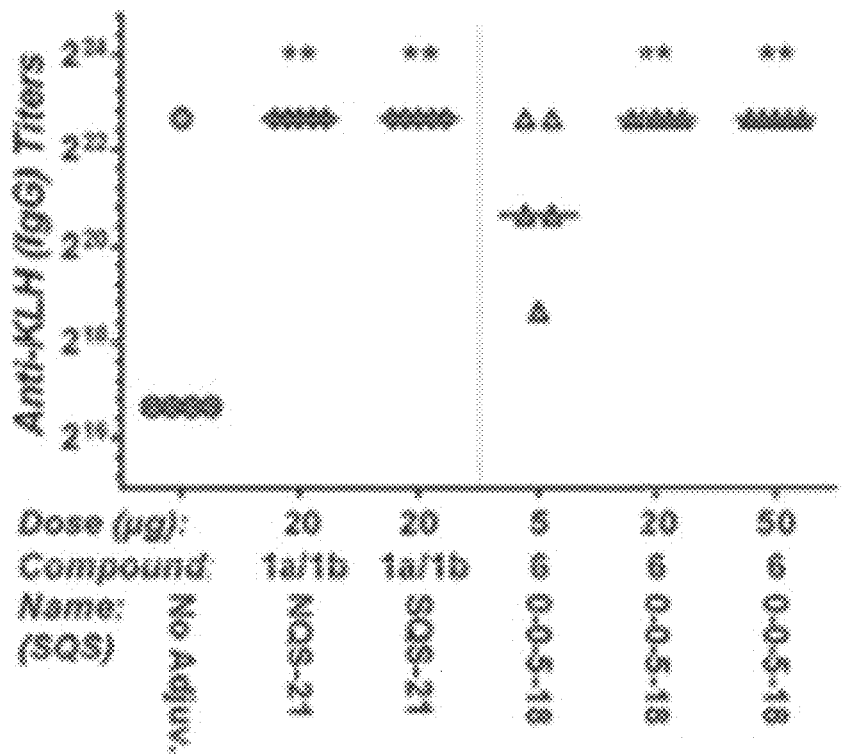
Figure 1E:
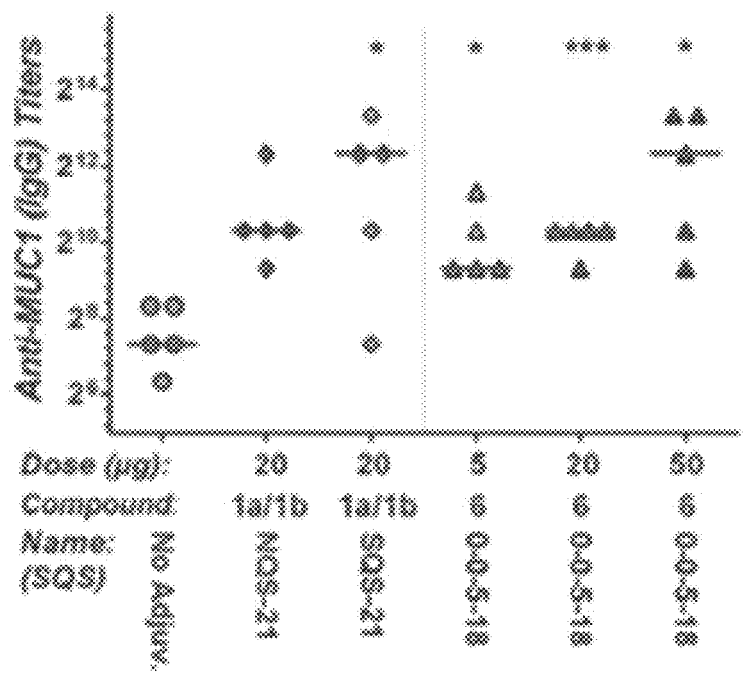
Figure 1F:
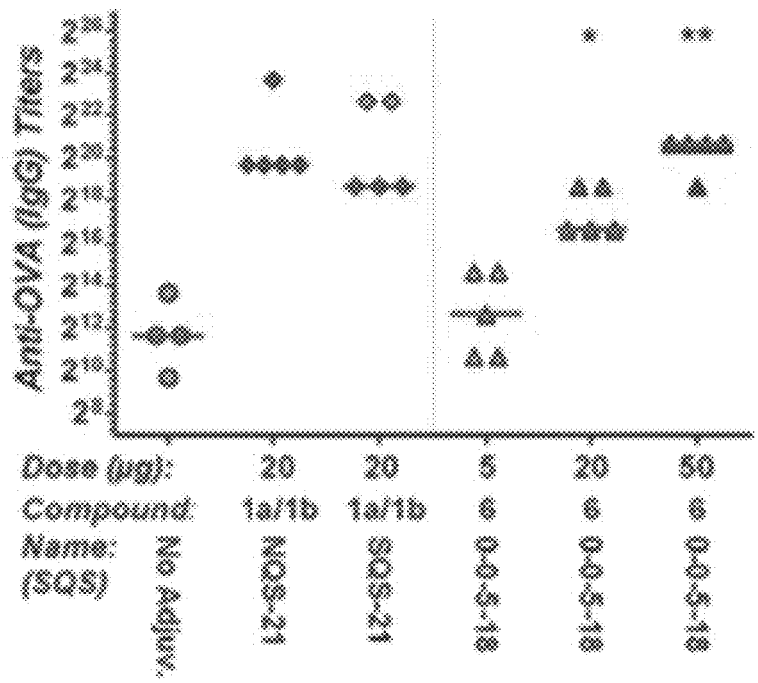
Figure 1G:
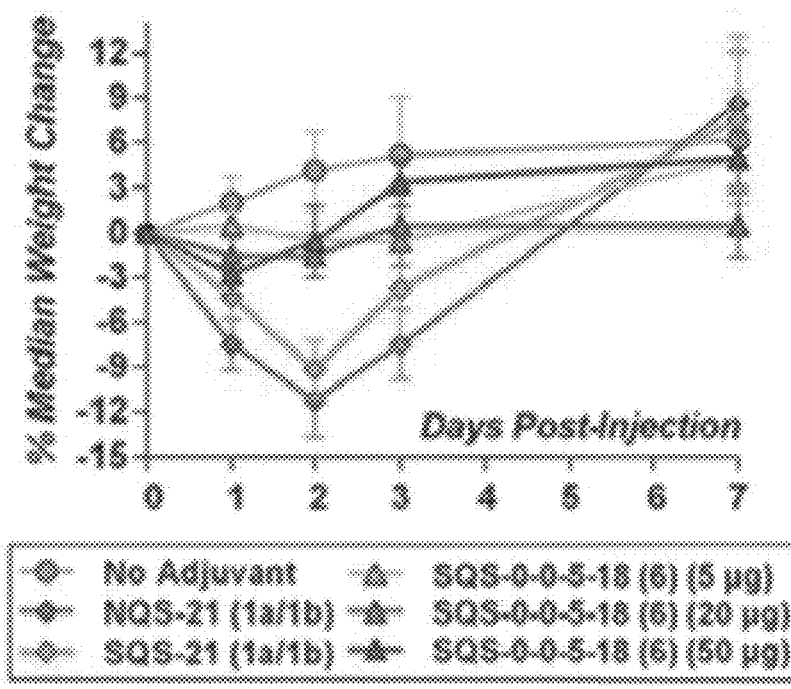
Figure 7A:
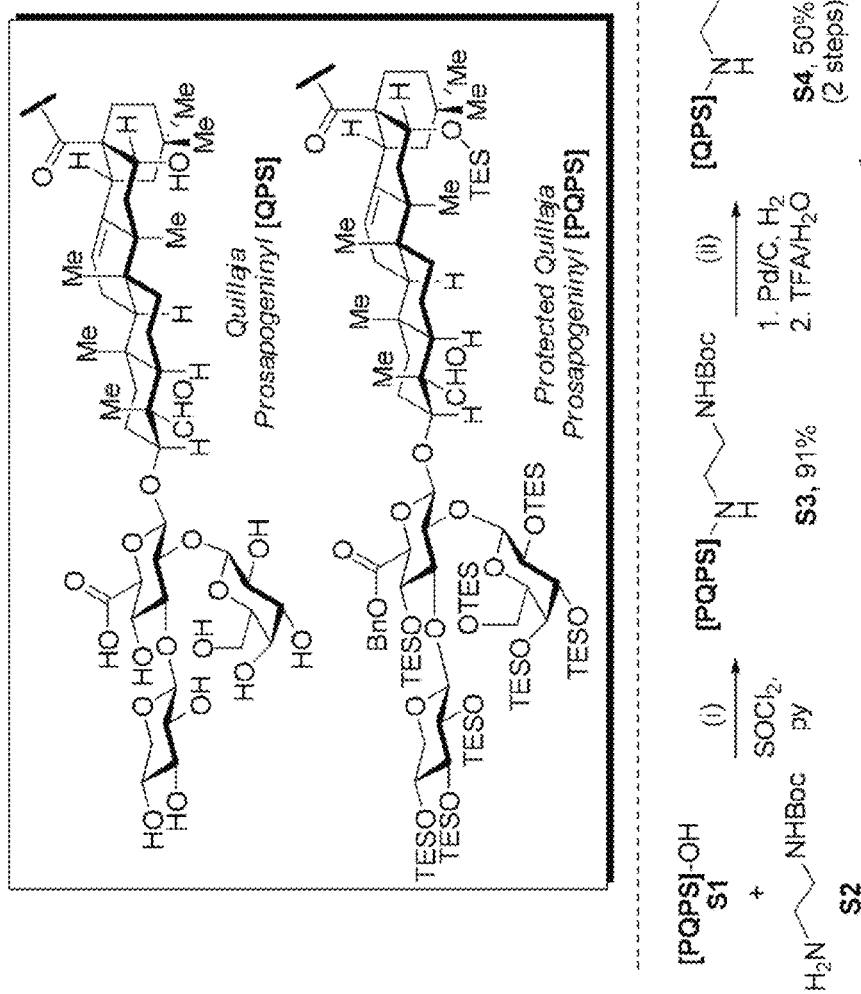
FIGS. 7A and 7B illustrate aryl iodide saponin 8 lacking the linear tetrasaccharide domain exhibits poor adjuvant activity in a preclinical mouse vaccination model.
Figure 7A:
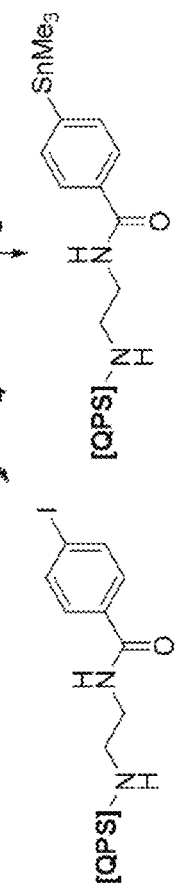
Figure 7B:
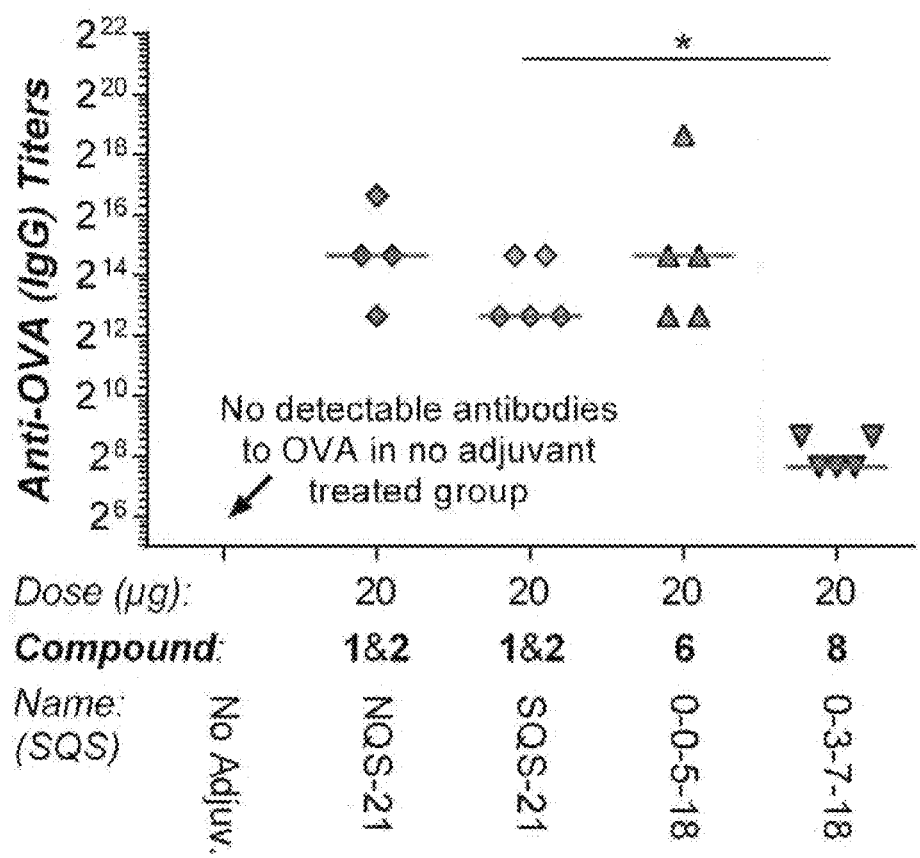

Aryl iodide saponin 6 (SQS-0-0-5-18) induced antibody titers comparable to both NQS-21 (natural QS-21) and SQS-21 (synthetic QS-21, 65% 1a:35% 1b) (FIGS. 1D-F) and also exhibited reduced toxicity compared to QS-21, as assessed by mouse weight loss (FIG. 1G). As a negative control, the iodinated saponin variant 8 (SQS-0-3-7-18) was synthesized, which lacks the linear tetrasaccharide domain (FIG. 1C and FIG. 7) and exhibited poor adjuvant activity (FIG. 7).

Reactions were performed in flame-dried sealed-tubes or modified Schlenk (Kjeldahl shape) flasks fitted with a glass stopper under a positive pressure of argon, unless otherwise noted. Air- and moisture-sensitive liquids and solutions were transferred via syringe. The appropriate carbohydrate reagents were dried via azeotropic removal of water with toluene. Molecular sieves were activated at 350° C. and were crushed immediately prior to use, then flame-dried under vacuum. Organic solutions were concentrated by rotary evaporation below 30° C. Flash column chromatography was performed employing 230-400 mesh silica gel. Thin-layer chromatography was performed using glass plates pre-coated to a depth of 0.25 mm with 230-400 mesh silica gel impregnated with a fluorescent indicator (254 nm).

Example 2: Biodistribution of Radioiodinated Saponins [$^{131}$I]$^{-6}$ and [$^{131}$I]$^{-8}$ For biodistribution studies, radiolabeled aryl iodide saponin [$^{131}$I]$^{-6}$ ([$^{131}$I]-SQS-0-0-5-18) was synthesized via aryl tin-halide exchange of trimethylstannane 7 (FIG. 1B). Radioiodinated [$^{131}$I]$^{-8}$ ([$^{131}$I]-SQS-0-3-7-18) was synthesized analogously from 9 as a negative control (FIG. 1C).

Figure 8A:
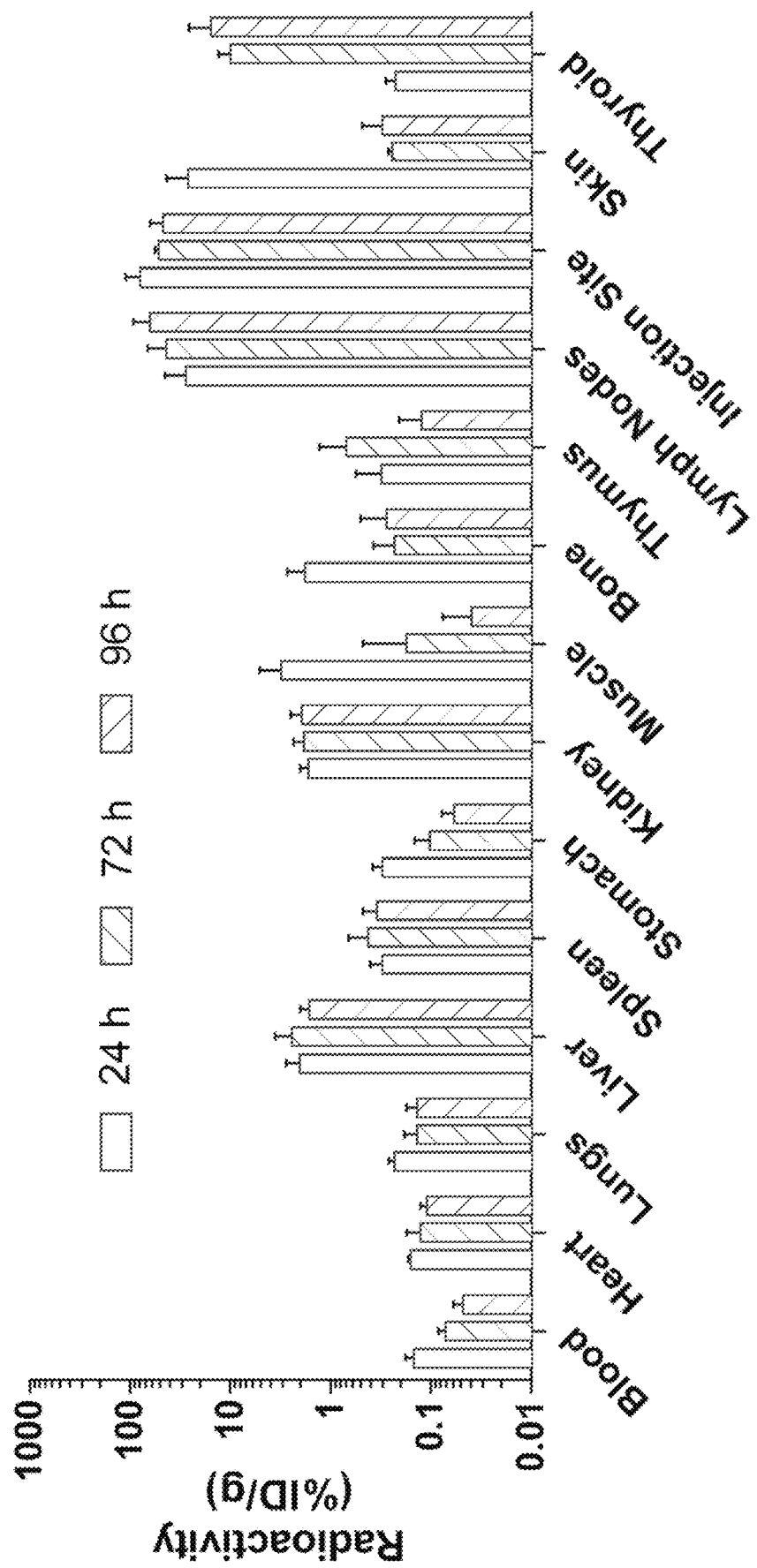
FIGS. 8A and 8B illustrate radioiodinated saponin $[^{131}I]-6$ localizes to and is retained at the lymph nodes and injection site in mice. Extended biodistribution of (a) active radioiodinated saponin $[^{131}I]-6$ (FIG. 8A) and (b) inactive radioactive saponin $[^{131}I]-8$ (FIG. 8B) with OVA antigen at 24, 72, and 96 h post-administration. Significantly higher radioactivity was recovered in the lymph nodes and at the injection site with $[^{131}I]-6$ across all three timepoints while radioactivity in other organs where a large fold-difference was initially observed (muscle, bone, skin) decreased rapidly at the later timepoints; the increase in recovery from the thyroid at later timepoints is commonly observed for all radioiodinated tracers due to deiodination of the tracer. Statistical significance for $[^{131}I]-6$ compared to $[^{131}I]-8$ in each organ at each timepoint assessed using two-tailed unpaired Student's t-test with CI=95%. At 24 h: *=0.01≤p≤0.05 (significant): liver, muscle, lymph node, skin, thyroid; =0.001<p<0.01 (very significant): blood, lungs, spleen, kidneys, bone, injection site; *=p<0.001 (extremely significant): heart. At 72 h: *=0.01≤p≤0.05 (significant): spleen, thymus, lymph nodes, skin, bone; =0.001<p<0.01 (very significant): heart, lungs, liver, kidneys, ovaries, thyroid; *=p<0.001 (extremely significant): blood, injection site. At 96 h: *=0.01≤p≤0.05 (significant): bone, ovaries, thymus, skin, thyroid; =0.001<p<0.01 (very significant): lungs, spleen, stomach, kidney, lymph nodes, injection site; *=p<0.001 (extremely significant): blood, heart, liver.
Figure 8B:
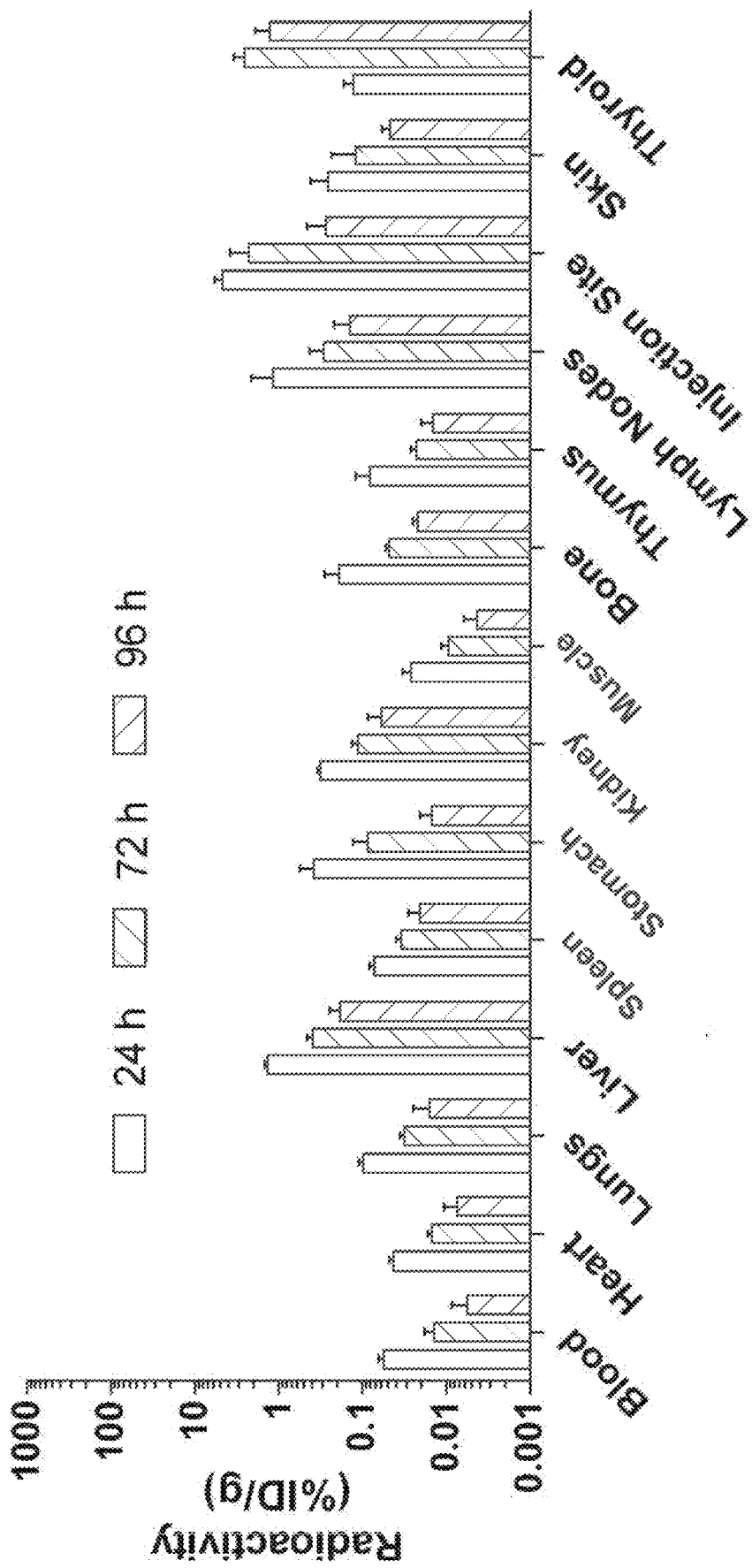

To identify tissues and organs that could play roles in saponin mechanisms of action, the acute in vivo biodistribution of the active adjuvant [$^{131}$I]$^{-6}$ was compared and the attenuated adjuvant [$^{131}$I]$^{-8}$ in mice co-administered with OVA. Treatment with [$^{131}$I]$^{-6}$, compared to [$^{131}$I]$^{-8}$, resulted in significantly higher recovery of radioactivity at the site of injection (17-fold higher, 78% ID/g [injected dose per gram]) and in the nearest draining lymph nodes (24-fold higher, 27% ID/g) at 24 h post-injection (FIG. 2A), which was retained at 72 h and 96 h post-injection (FIG. 8). In contrast, radioactivity in other tissues where large fold-differences were initially observed (muscle, bone, skin) decreased rapidly at the later timepoints. Minimal deiodination of [$^{131}$I]$^{-6}$, evidenced by low thyroid uptake (0.21% ID/g), was observed at 24 h (FIG. 2A), although deiodination increased at later time-points (FIG. 8). In contrast, the attenuated adjuvant [$^{131}$I]$^{-8}$ was recovered at significantly lower levels at the site of injection (4.5% ID/g) and nearest draining lymph nodes (1.1% ID/g) at 24 h post-injection (FIG. 2A) and was further cleared from both sites at later time-points (FIG. 8). Taken together, these data indicate that only the active adjuvant 6 (SQS-0-0-5-18) localizes to and is retained at the injection site and lymph nodes, while the attenuated adjuvant 8 (SQS-0-3-7-18) is not.

The molecular mechanisms of the adjuvant activity of QS-21 and its variants remain poorly understood. It has been reported that QS-21 stimulates mixed Th1/Th2 helper T-cell responses, corresponding to cellular and humoral immunity respectively, including antigen-specific CD8+ cytotoxic T lymphocytes. There is some evidence to suggest that QS-21 does not bind to Toll-like receptors 2 and 4 and that it does not operate by a depot effect, in which the adjuvant increases the lifetime of the antigen, extending its presentation to the immune system. It has also been suggested that *Quillaja* saponins may, by analogy to tucaresol, bind covalently to amino groups on T-cell surface receptors via imine formation at the C4-aldehyde substituent, providing costimulation for T-cell activation.

Figure 9A:
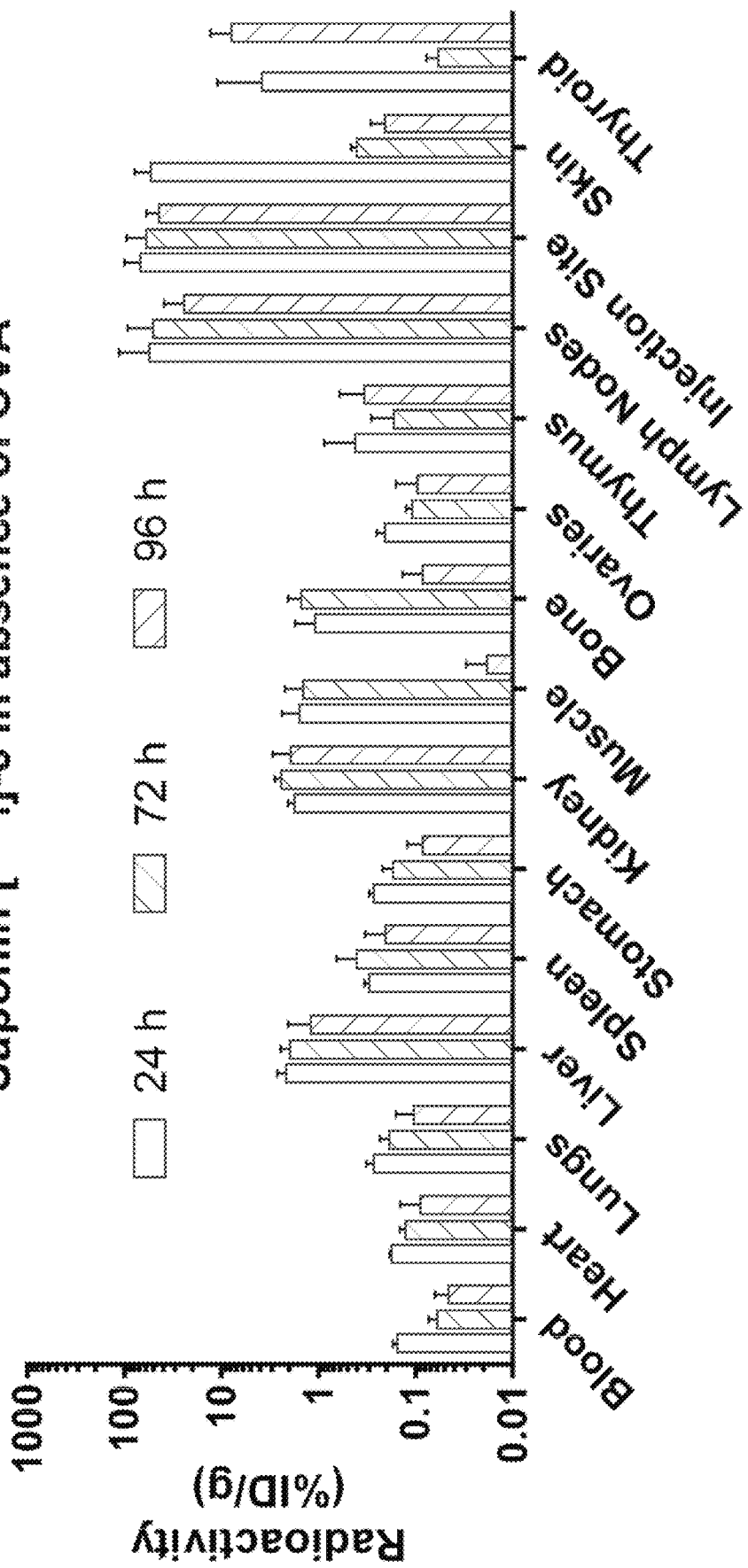
FIGS. 9A to 9D illustrate biodistribution of radioiodinated saponins $[^{131}I]-6$ and $[[^{131}I]-8$ is not perturbed by the absence of OVA antigen. Biodistribution of (a) active adjuvant $[^{131}I]-6$ ($[^{131}I]$-SQS-0-0-5-18) (FIG. 9A) and (b) attenuated adjuvant $[^{131}I]-8$ ($[^{131}I]$-SQS-0-3-7-18) (FIG. 9B). Comparison of radioactivity recovered in (c) the lymph nodes (FIG. 9C) and (d) at the injection site (FIG. 9D), where significantly higher radioactivity was recovered with $[^{131}I]-6$ across all three timepoints while radioactivity in other organs where a large fold-difference was initially observed (muscle, bone, skin) decreased at the later timepoints. Statistical significance for $[^{131}]-6$ compared to $[^{131}I]-8$ in each organ at each timepoint assessed using two-tailed unpaired Student's t-test with CI=95%, not shown graphically in parts (a) and (b) for clarity. At 24 h: *=0.01≤p≤0.05 (significant): muscle, bone, ovaries, injection site, skin; =0.001<p<0.01 (very significant): lungs, liver, spleen, kidneys, thymus; *=p<0.001 (extremely significant): blood, heart. At 72 h: *=0.01≤p≤0.05 (significant): spleen, thymus, lymph node, injection site; =0.001<p<0.01 (very significant): blood, lungs, liver, muscle, bone, thyroid; *=p<0.001 (extremely significant): heart, kidney, ovaries, skin. At 96 h: *=0.01≤p≤0.05 (significant): heart, lungs, liver, spleen, kidney, thymus, lymph node, skin; **=0.001<p<0.01 (very significant): blood, injection site.
Figure 9B:
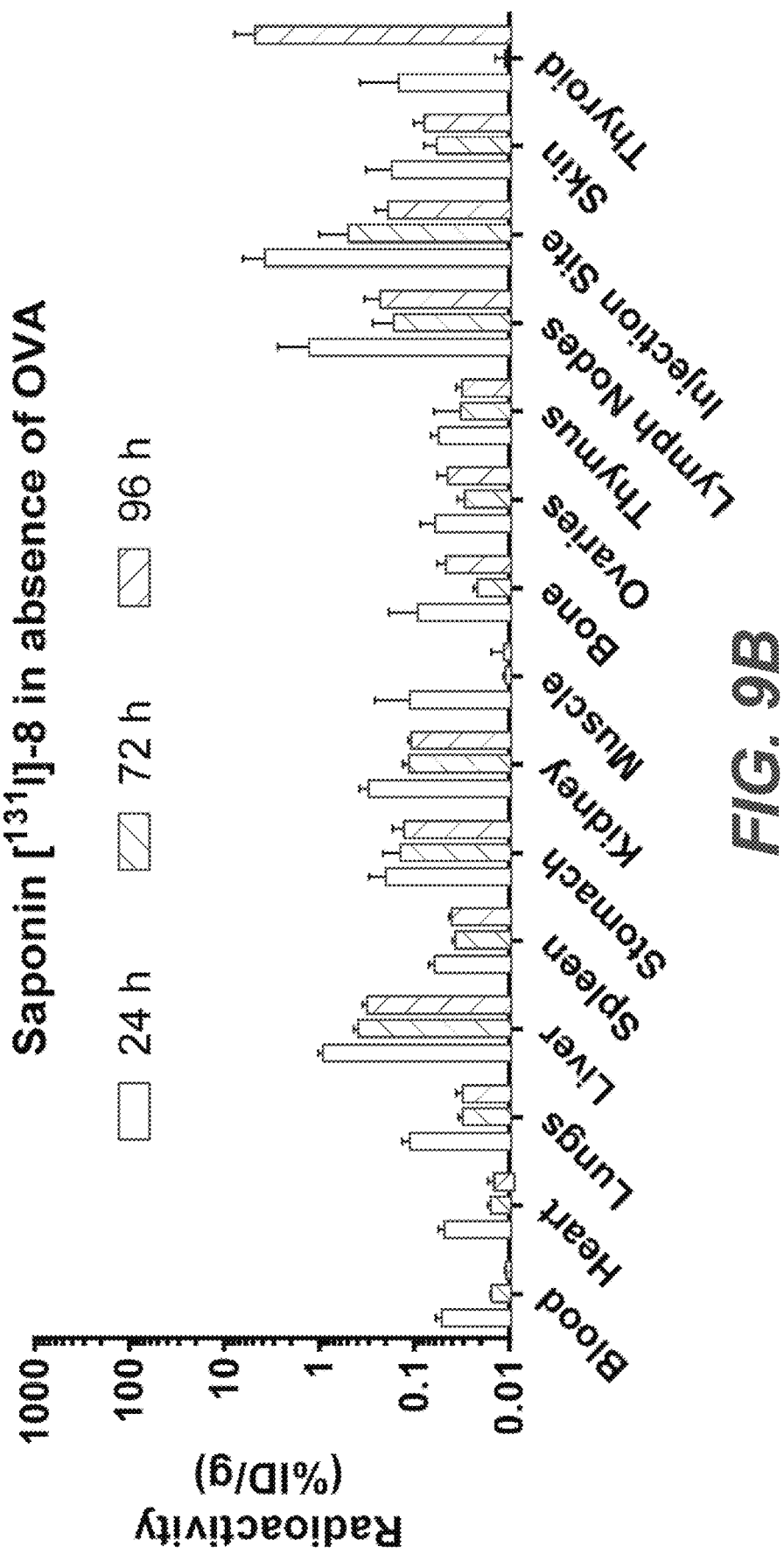
Figures 9C, 9D:
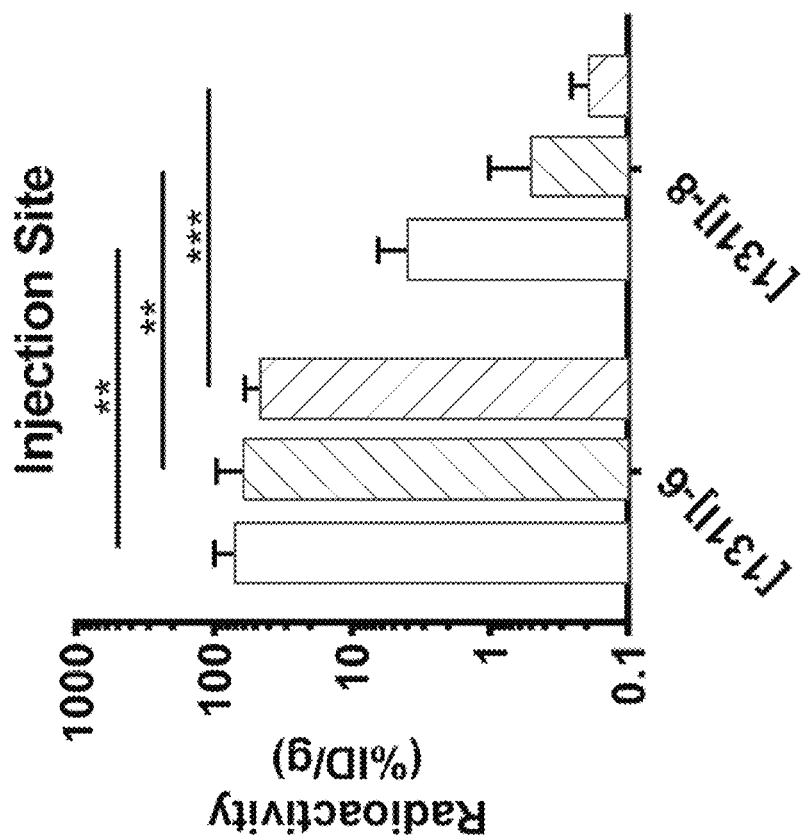

Other adjuvants that contain mixtures of *Quillaja* saponins have previously been reported to affect the biodistribution of antigens, although it is not known whether biodistribution of the adjuvant is influenced by the presence or absence of the antigen. To investigate these effects with these structurally-defined QS-21 variants, the biodistribution of active adjuvant [$^{131}$I]$^{-6}$ and inactive adjuvant [$^{131}$I]$^{-8}$ in absence of OVA was assessed (FIG. 9). In both cases, the biodistribution profiles were comparable to those observed in the presence of OVA above (FIG. 8), indicating that the presence of the antigen OVA does not impact the biodistribution of these saponin adjuvants.

Figure 10A:
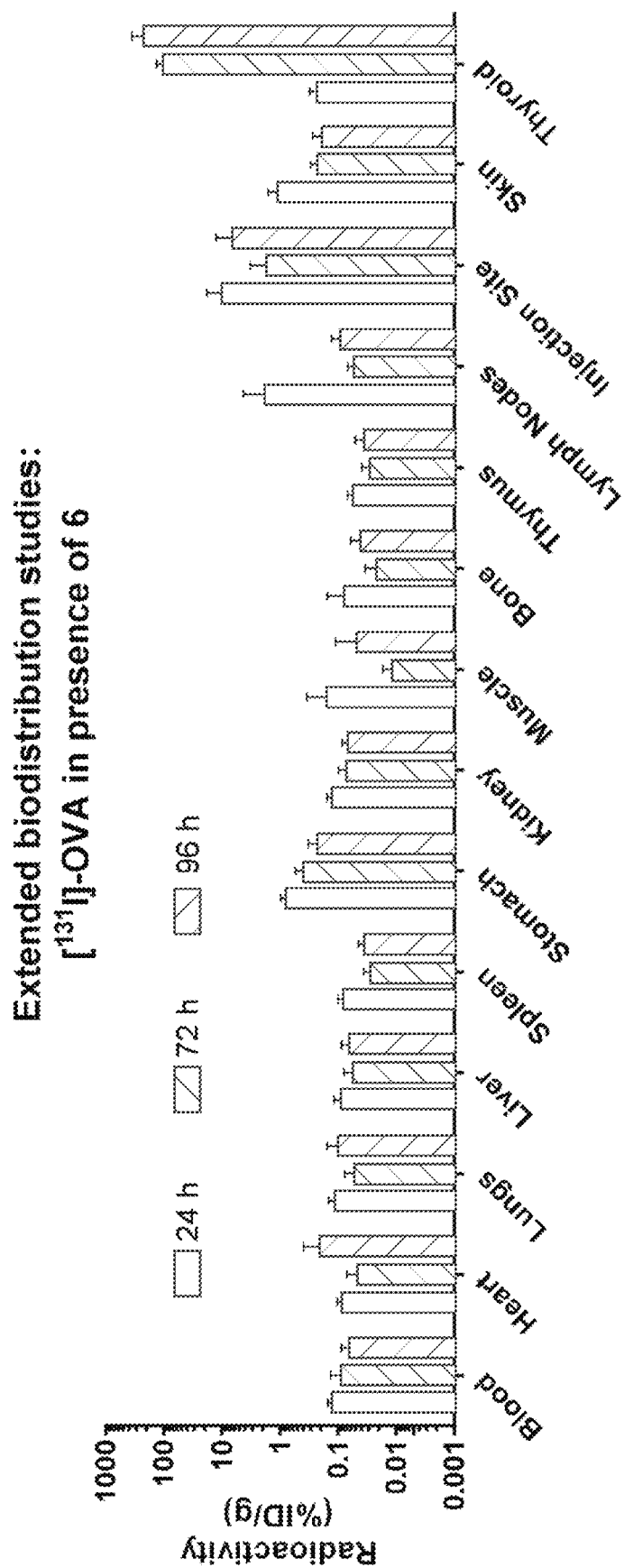
FIGS. 10A and 10B illustrate biodistribution of radioiodinated ovalbumin ($[^{131}I]$-OVA) indicates rapid deiodination. Biodistribution at 24, 72, and 96 h post-administration in the (a) presence (20 μg) (FIG. 10A) and (b) absence (FIG. 10B) of active adjuvant 6 (SQS-0-0-5-18). Statistical significance for vaccination with 6 compared to without 6 in each organ at each timepoint assessed using two-tailed unpaired Student's t-test with CI=95%, not shown graphically for clarity. At 24 h: *=0.01≤p≤0.05 (significant): heart, skin; **=0.001<p<0.01 (very significant): thymus. At 72 h: *=0.01≤p≤0.05 (significant): stomach, lymph node, skin. At 96 h: *=0.01:Sp:S 0.05 (significant): blood, lungs, stomach, kidney, bone; **=0.001<p<0.01 (very significant): spleen, ovaries, thymus.
Figure 10B:
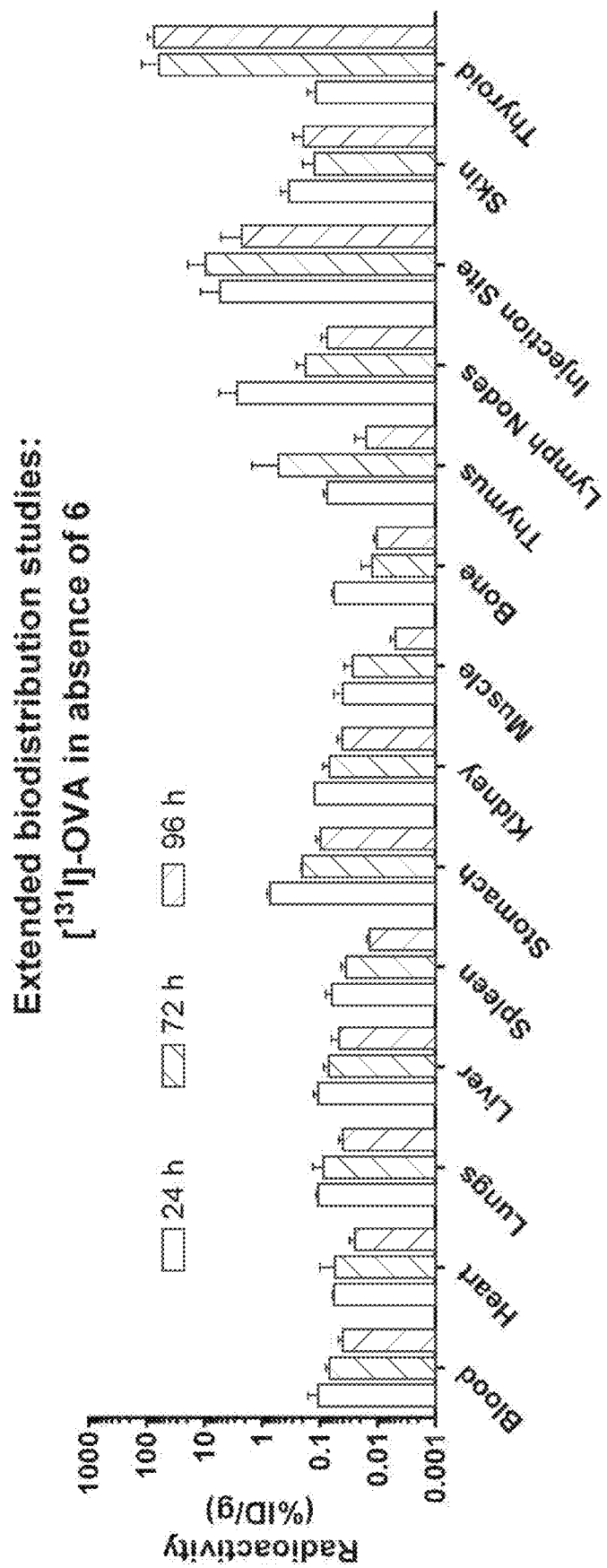

In a complementary experiment, the biodistribution of [$^{131}$I]-OVA in the presence and absence of active adjuvant 6 was examined (FIG. 10). Although comparable biodistribution profiles resulted, thyroid uptake was also high, indicative of rapid deiodination of [$^{311}$I]-OVA, which is commonly observed for radioiodinated proteins. Thus, the influence of 6 upon OVA antigen biodistribution could not be assessed effectively and an alternative experimental approach was required.

Figure 11:
FIG. 11 illustrates fluorescein-labeled active adjuvant 3 is retained at the injection site. Whole mouse images with fluorescent saponin 3 (SQS-0-0-5-12) and amine containing inactive adjuvant 2 (SQS-0-0-5-11) for comparison to FIG. 2B herein.

To address this problem, in vivo fluorescence imaging experiments with fluorescein-labeled active adjuvant 3 (SQS-0-0-5-12) and Alexa-647-conjugated OVA (OVA-A647) were conducted. At 24-h post-injection, we observed retention of the fluorescent saponin at the injection site (FIG. 2b) and accumulation within the draining lymph nodes (left node in FIG. 2c), consistent with the biodistribution results above. Immunohistochemical analysis of dissected nodes indicated subnodal localization of adjuvant 3 to the cortex of the draining inguinal node. Flow cytometric analysis demonstrated dendritic-cell-specific internalization of 3 within the lymph nodes. Moreover, while OVAA647 was observed at the site of injection in mice treated with both the active adjuvant 3 and an unlabeled, inactive adjuvant 2 (SQS-0-0-5-11) (FIG. 2b and FIG. 11), it only localized to the nearest draining lymph nodes when co-injected with the active adjuvant 3 (FIG. 2c). Overall, these data suggest a role for the active saponin 3 in the trafficking of the OVA antigen by antigen-presenting cells to the draining lymph nodes, where the antigen is presented to the adaptive immune system.

Example 3: Truncated Saponin Lacking Branched Trisaccharide Domain (16)

Figure 3A:
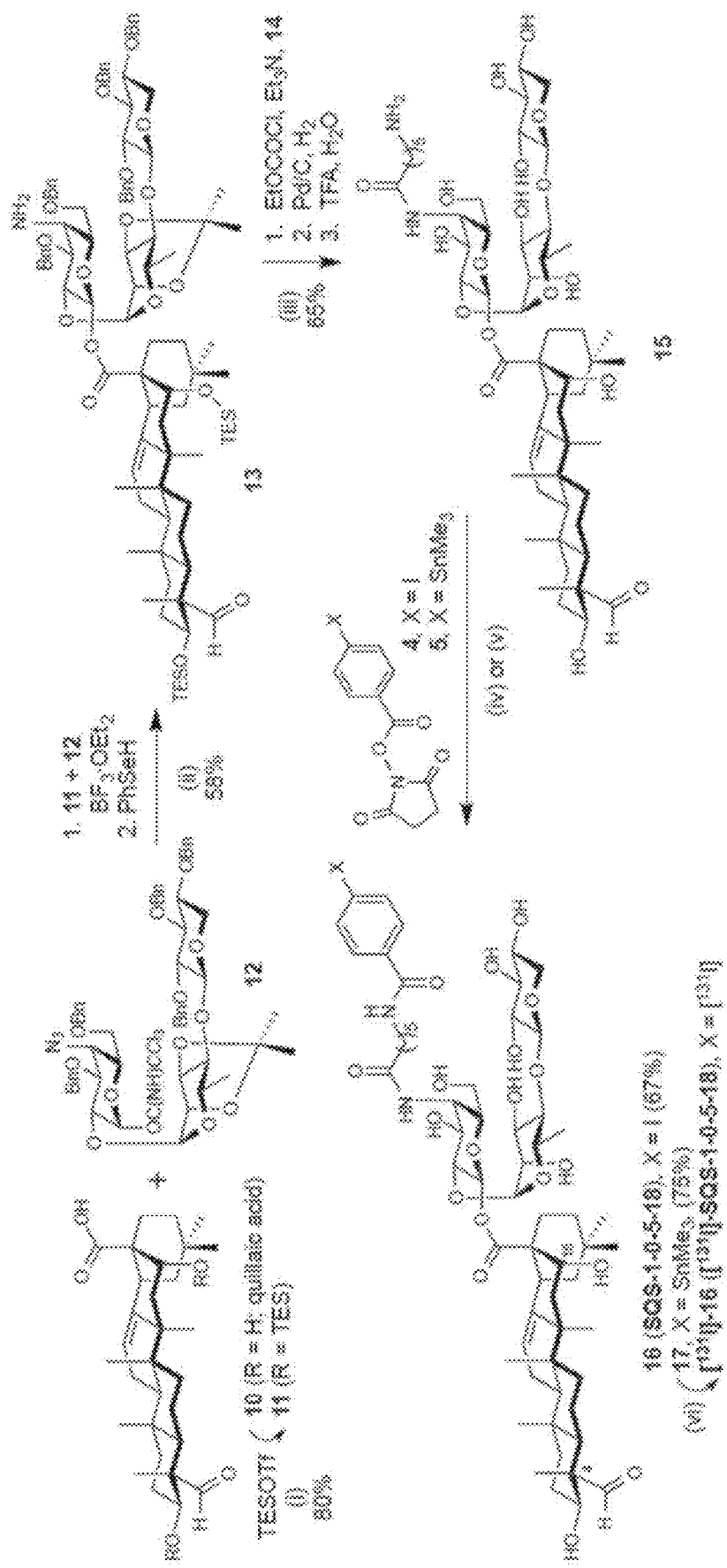
FIGS. 3A to 3E illustrate truncated saponin 16 lacks the entire branched trisaccharide domain of QS-21 but retains potent adjuvant activity and low toxicity in a preclinical mouse vaccination model.

The requisite triterpene cores were selectively silylated (TESOTf, 2,6-lutidine) at hydroxyl groups to provide protected triterpenes having a free C28-carboxylic acid. B-Selective Schmidt glycosylation (BF3·OEt2) with trisaccharide trichloroacetimidate donor 12 (Chea, E. K. et al. Synthesis and preclinical evaluation of QS-21 variants leading to simplified vaccine adjuvants and mechanistic probes. J. Am. Chem. Soc. 134, 13448-13457 (2012)) followed by reduction of the azide (PhSeH) gave the corresponding glycosyl esters. Acylation of the amine with 6-((t-butoxycarbonyl)-amino)hexanoic acid (14) (EtOCOCl, Et$_3$N) and subsequent global deprotection by hydrogenolysis (H2, Pd/C) and acid hydrolysis (TFA/H2O) afforded the fully deprotected saponins bearing the free amine at the terminus of the acyl chain domain. Late-stage acylation of the amine with succinimidyl esters 4 or 5 gave the corresponding aryl iodides 16, 18-22 or the relevant aryl tin congeners, respectively (FIG. 3a).

Figure 3B:
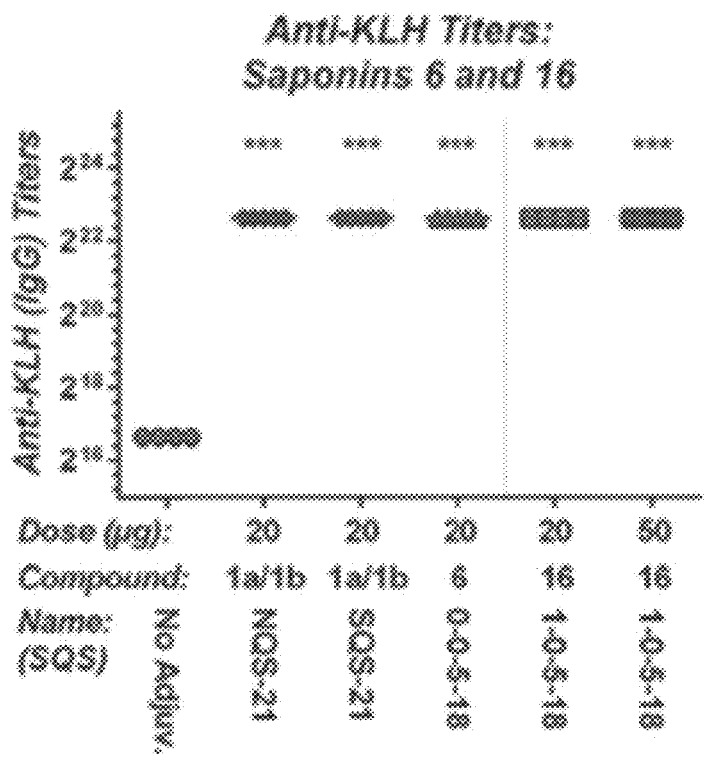
Figure 3C:
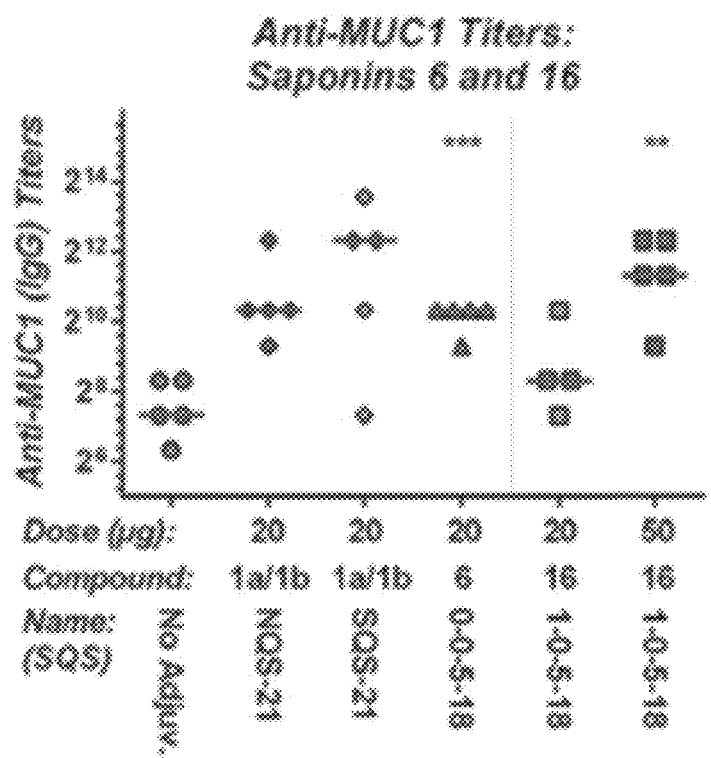
Figure 3D:
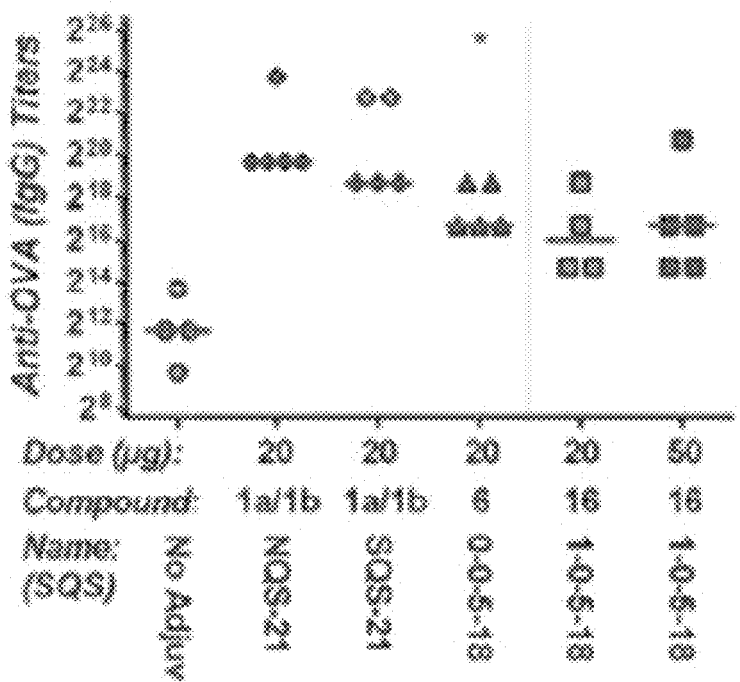
Figure 3E:
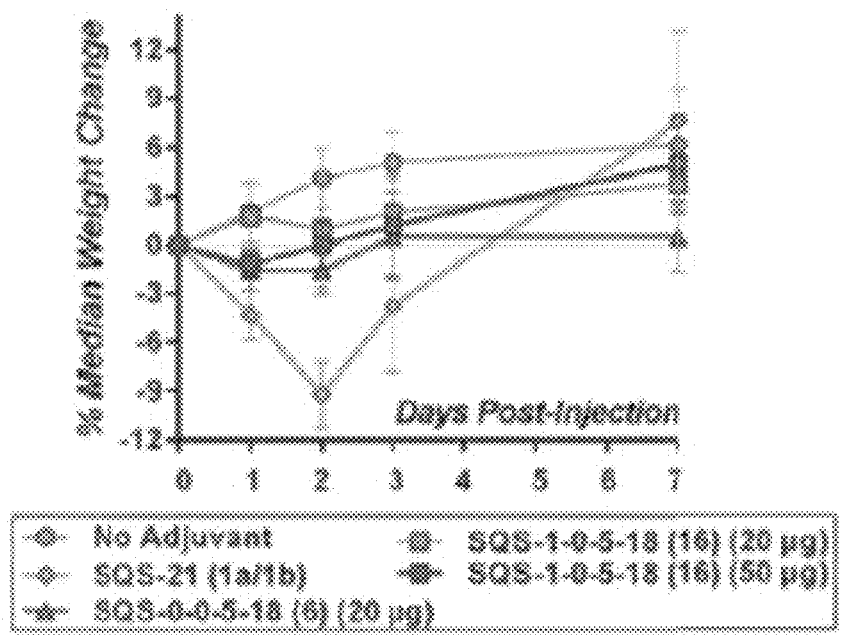
Figure 4A:
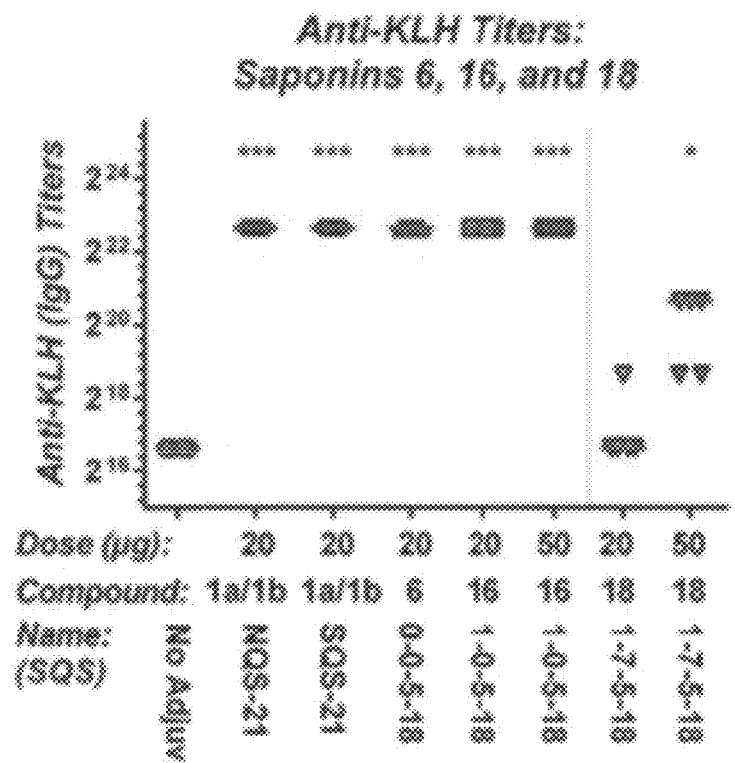
FIGS. 4A to 4D illustrate oleanolic acid derivative 18, which lacks both the C4-aldehyde substituent and C16-alcohol in the triterpene domain of QS-21, exhibits poor adjuvant activity in a preclinical mouse vaccination model. Biological evaluation of oleanolic acid derivative 18 (SQS-1-7-5-18) with a three-component vaccine for (FIG. 4A) anti-KLH titers (IgG), (FIG. 4B) anti MUC1 titers (IgG) and (FIG. 4C) anti-OVA titers (IgG), indicating attenuated adjuvant activity; horizontal bars indicate median titers; statistical significance compared to no-adjuvant control: *=p≤0.05, =p<0.01, *=p<0.001.
Figure 4B:
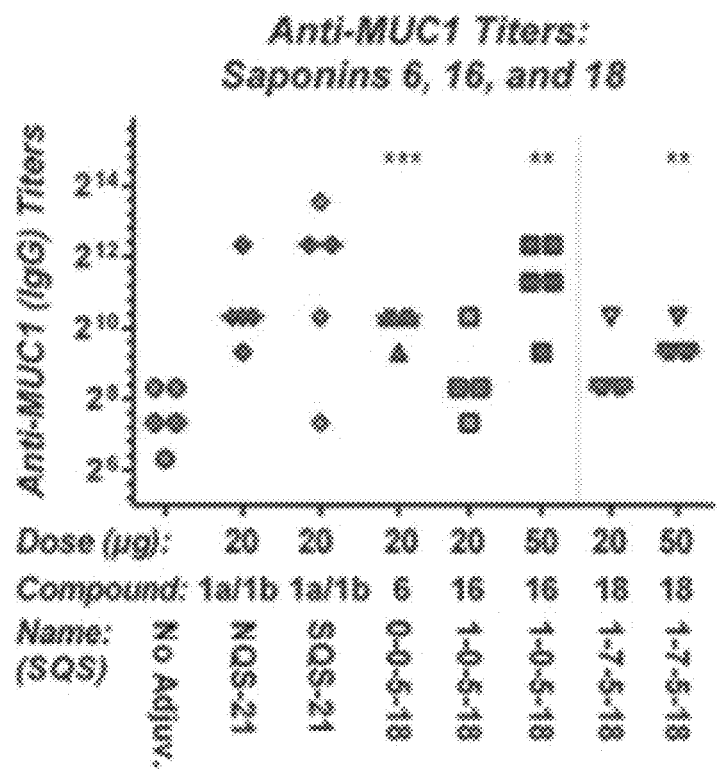
Figure 4C:
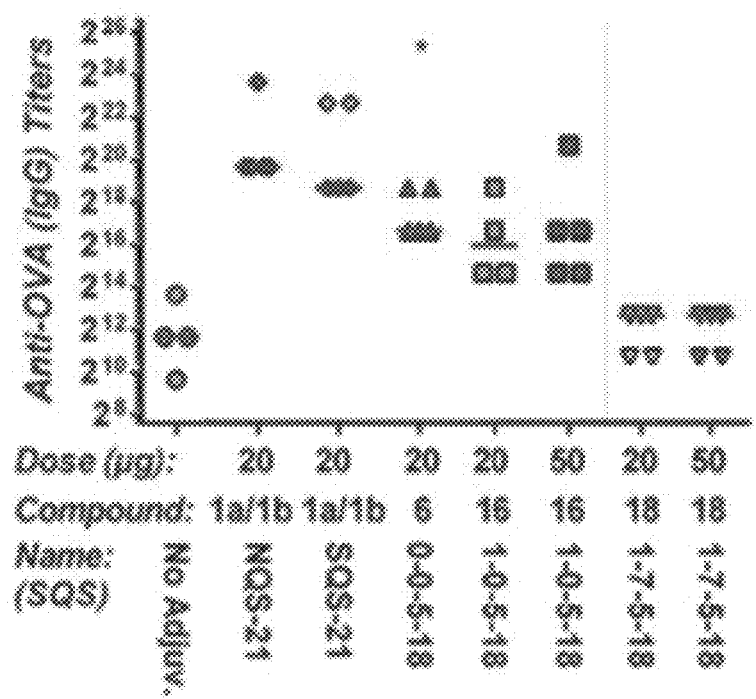
Figure 4D:
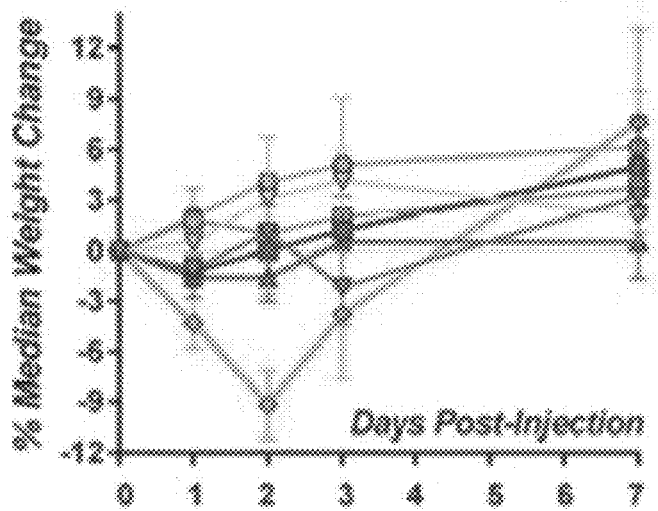
Figure 4D:
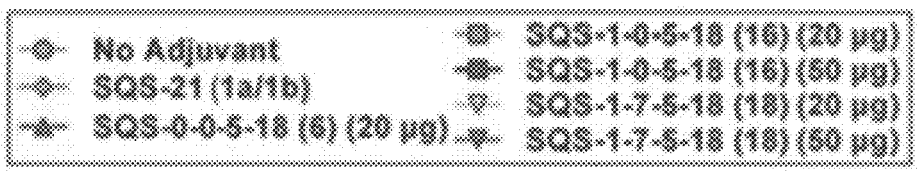

Having established saponin variant 6 (SQS-0-0-5-18) as a potent adjuvant with low toxicity, the role of the branched trisaccharide domain in adjuvant activity was investigated. Truncated saponin 16 (SQS-1-0-5-18), which lacks this entire domain, was synthesized from quillaic acid 1) and protected trisaccharide 12 (FIG. 3a). Remarkably, truncated saponin 16 elicited KLH and MUC1 antibody responses comparable to those of parent aryl iodide 6, NQS-21, and SQS-21, and significantly higher than those of the no-adjuvant control, with the exception of anti-MUC1 titers at the lower dose (20 μg) (FIGS. 3b, 3c). Antibody titers against OVA were also similar to those elicited by parent aryl iodide saponin 6 and considerably higher than those of the no-adjuvant control (FIG. 3d). Moreover, truncated saponin 16 exhibited much lower toxicity than NQS-21 and SQS-21, slightly lower than that of even the parent aryl iodide 6 (FIG. 3e). Thus, the entire branched trisaccharide domain is not required for adjuvant activity in the truncated saponin variant 16. This represents a major simplification of the saponin structure and provides a more favorable activity/toxicity profile than QS-21 itself.

Example 4: Saponins with Targeted Triterpene Domain Modifications (18-22)

Groups of five mice (C57BL/6J, female, 6-8 weeks of age) were vaccinated with a three-component vaccine consisting of MUC1-KLH (2.5 mg) and OVA (20 mg), or a four-component vaccine that also included GD3-KLH (5 mg). Antigens were co-administered with the adjuvant of interest (5, 20, or 50 mg) or without adjuvant (no-adjuvant control) in phosphate buffered saline (PBS, 100 mL) via subcutaneous injections on days 0, 7, and 14, followed by a booster on day 65. Mouse sera were collected at day 72 and antibody titers against each antigen were determined by ELISA. Statistical significance of each antibody response compared to the no-adjuvant control was assessed using a two-tailed unpaired Student's t-test with CI=95%. As an initial, general assessment of toxicity, mouse weight loss was monitored on days 0, 1, 2, 3, and 7 after the first vaccination. These animal experiments were conducted as described in MSKCC Institutional Animal Care and Use Committee (IACUC) protocol #97-11-051.

The aryl tin saponins (7, 9, 17, S9) were synthesized from the corresponding amine precursors (2, S4, 15, S8) by acylation with N-succinimidyl-4-(trimethylstannyl)benzoate 4 ($Et_3N$, DMF, 21° C., 1-2.5 h). Radiolabeling was achieved by iodination of the aryl tin saponin (20 μg) with $[^{131}I]$—NaI and chloramine-T (methanol, 21° C., 1 min), followed by immediate HPLC purification. Solvents were removed by rotary evaporation at 35° C. and the radioiodinated probes were formulated in 0.9% saline for biodistribution studies. Co-elution of the radioiodinated probes with the corresponding cold saponins was used for quality control analysis.

Radiolabeled ovalbumin was synthesized by treating 20 μg of ovalbumin with $[^{131}I]$—NaI and Chloramine-T in methanol. The reaction mixture was diluted with 2 mL phosphate buffered saline (PBS) followed by centrifugal filtration at 2800 rpm for 12 min using a 30 kDa molecular weight cutoff filter. This process was repeated twice and the concentrated compound was then formulated in 1 mL 0.9% saline for biodistribution studies.

Figure 12:
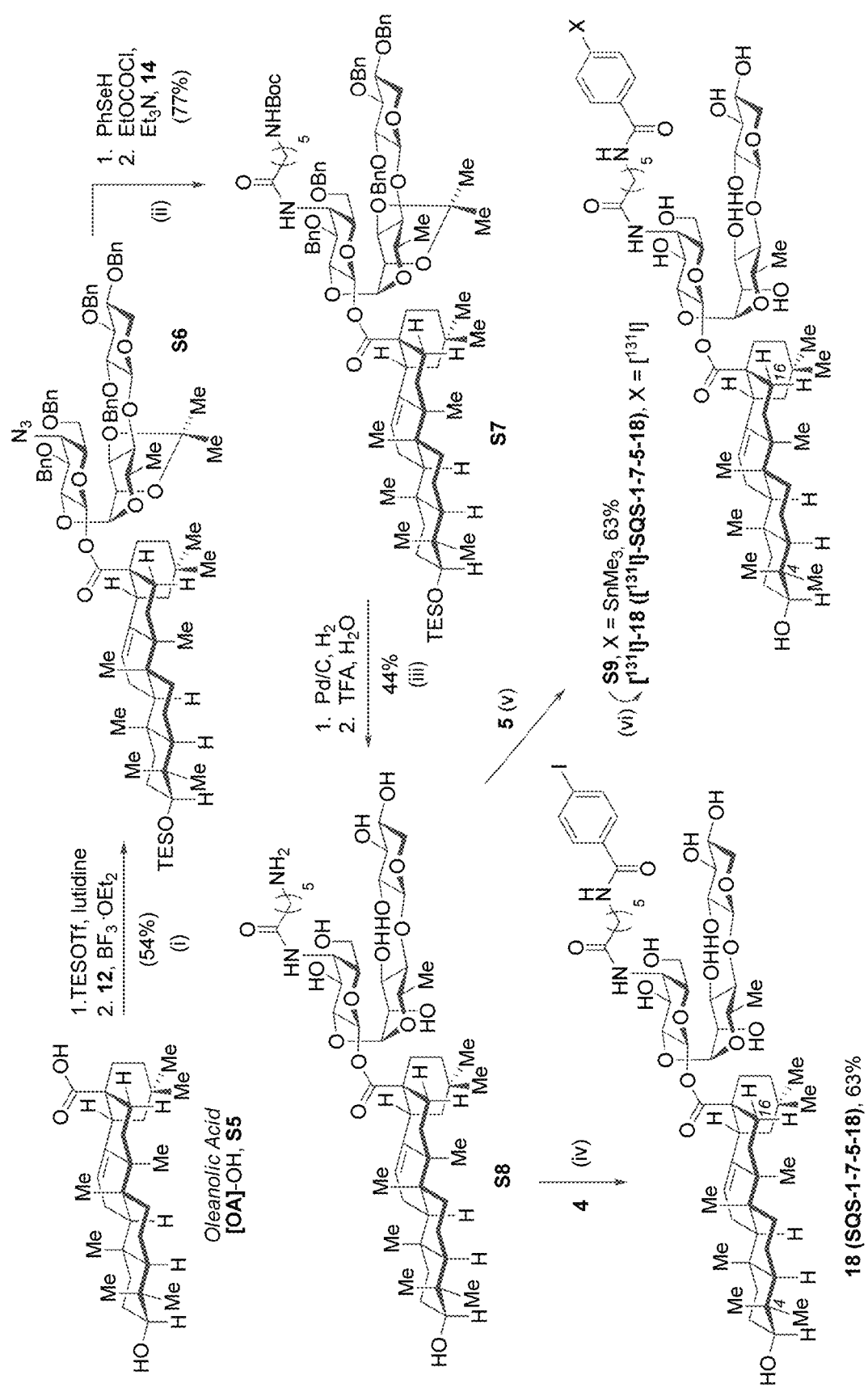
FIG. 12 illustrates synthesis of aryl iodide and aryl tin variants derived from oleanolic acid 18 ([SQS-1-7-5-18]) and S9. (i) 1. TESOTf, 2,6-lutidine, $CH_2Cl_2$, 0° C., 1 h; 2. 12, BF3·$OEt_2$, 4 Å M.S., $CH_2Cl_2$, −50° C., 20 min, 21° C., 2 min [two temperature cycles], 54% (2 steps); (ii) 1. PhSeH, $Et_3N$, 38° C., 8 h; 2. $HO_2C(CH_2)_5NHBoc$ (14), EtOCOCl, $Et_3N$, THF, 0° C., 2.5 h, [acid preactivation], then, 0° C., 1.5 h, 77% (2 steps); (iii) 1. H2 (50 psi), Pd/C (Degussa), THF/EtOH (1:1), 21° C., 24 h; 2. $TFA/H_2O$ (4:1), 0° C., 2 h, RP-HPLC, 44% (2 steps); (iv) 4, $Et_3N$, DMF, 21° C., 2 h, RP-HPLC; 63%; (v) 5, $Et_3N$, DMF, 21° C., 1.5 h, RP-HPLC, 63%; (vi) [131I]—NaI, Chloramine-T, MeOH, 21° C., 1 min, RP-HPLC, 55%.

The discovery that the entire branched trisaccharide domain is not required for adjuvant activity facilitated investigation of the triterpene domain of QS-21 by semi-synthesis of new variants from alternative triterpene precursors, by analogy to the synthesis of 16 (SQS-1-0-5-18) from quillaic acid (FIG. 3A). The roles of the C4-aldehyde substituent and C16-alcohol in the quillaic acid core structure were of particular interest. Previously, the C4-aldehyde substituent has been proposed to be important for the adjuvant activity of QS-21. However, other saponins that lack a triterpene aldehyde substituent but are active adjuvants have been identified recently. Thus, an initial variant 18 (SQS-1-7-5-18) was synthesized from oleanolic acid (FIG. 12), which shares the same carbon skeleton as quillaic acid, differing only in the oxidation states at the $C_4$ substituent (Me vs. CHO) and C16 (H vs. OH).

Oleanolic acid derivative 18 (C16-Me, C16-H) led to lower antibody titers against all three antigens compared to the parent quillaic acid derivative 16 (FIGS. 4A-D). Further, OVA antibody titers with oleanolic acid derivative 18 were similar to those in the no-adjuvant control. Thus, removal of both the C4-aldehyde substituent and C16-alcohol in oleanolic acid derivative 18 results in considerably attenuated antibody responses in this preclinical vaccination model.

Figure 5A:
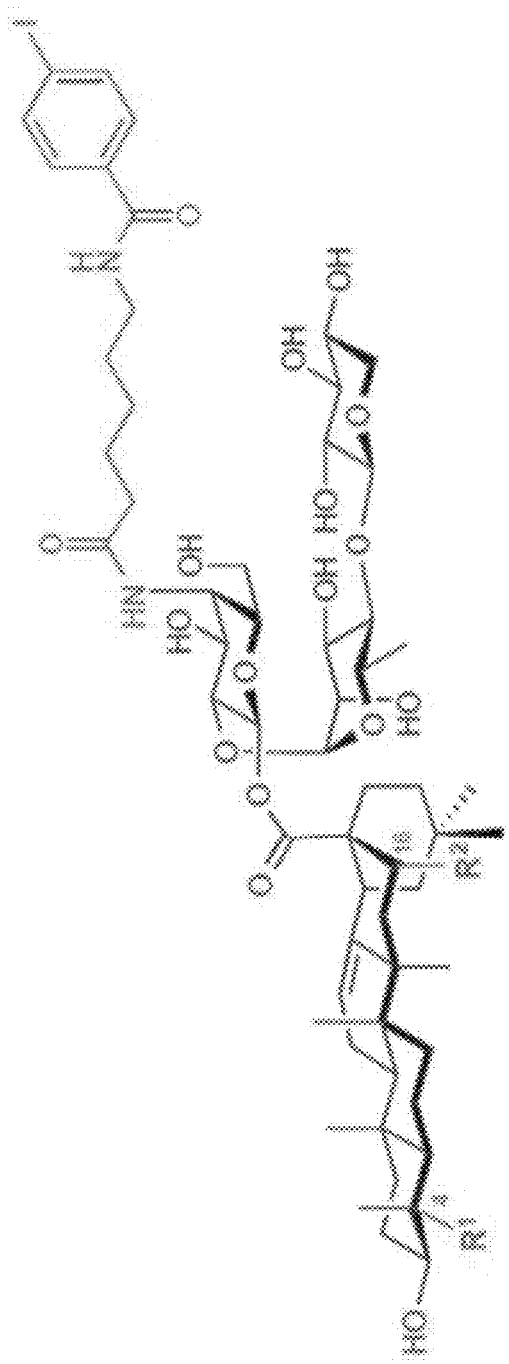
FIGS. 5A to 5G illustrate caulophyllogenin derivative 19 and echinocystic acid derivative 20, which lack the C4-aldehyde substituent but retain the C16-alcohol in the triterpene domain of QS-21, exhibit potent adjuvant activity and no toxicity in a preclinical mouse vaccination model.
Figure 5B:
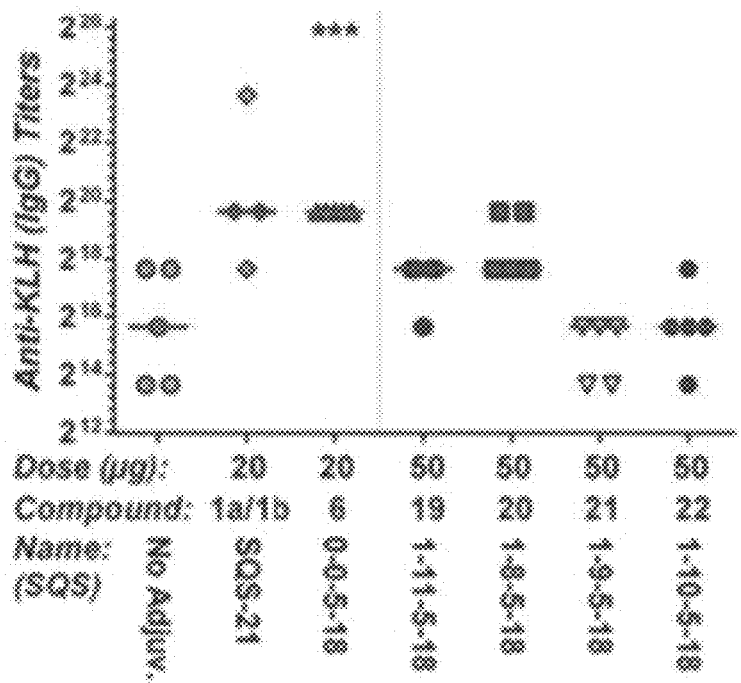
Figure 5C:
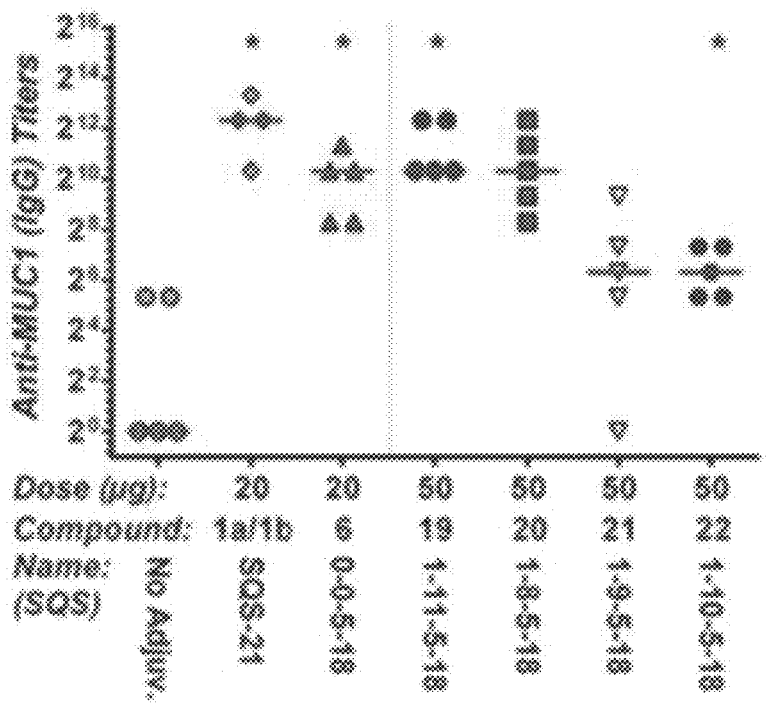
Figure 5D:
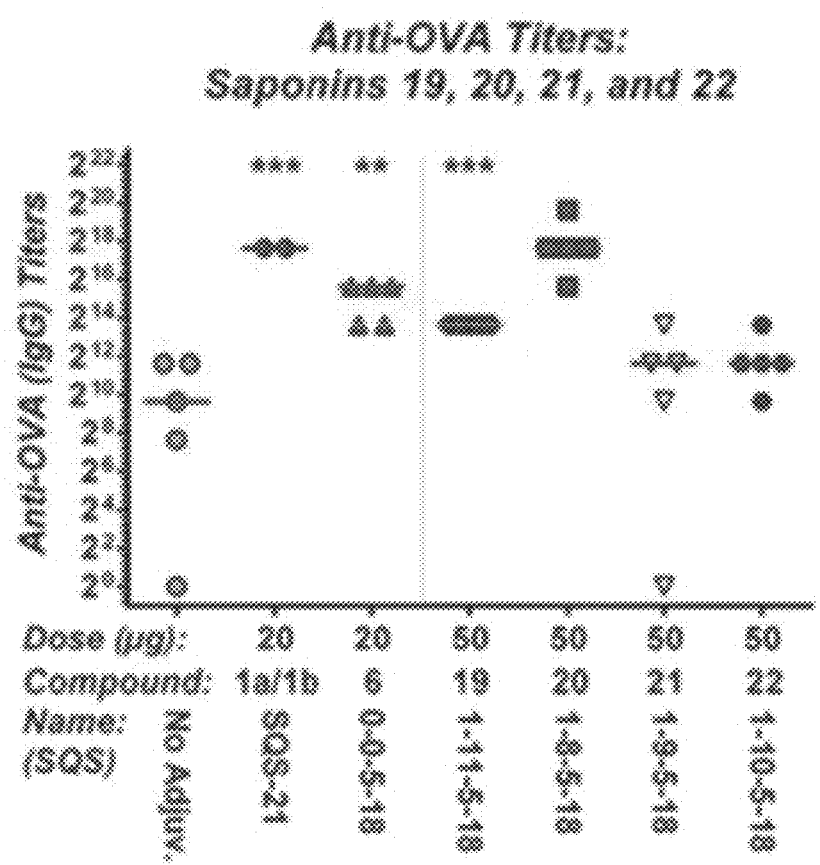
Figure 5E:
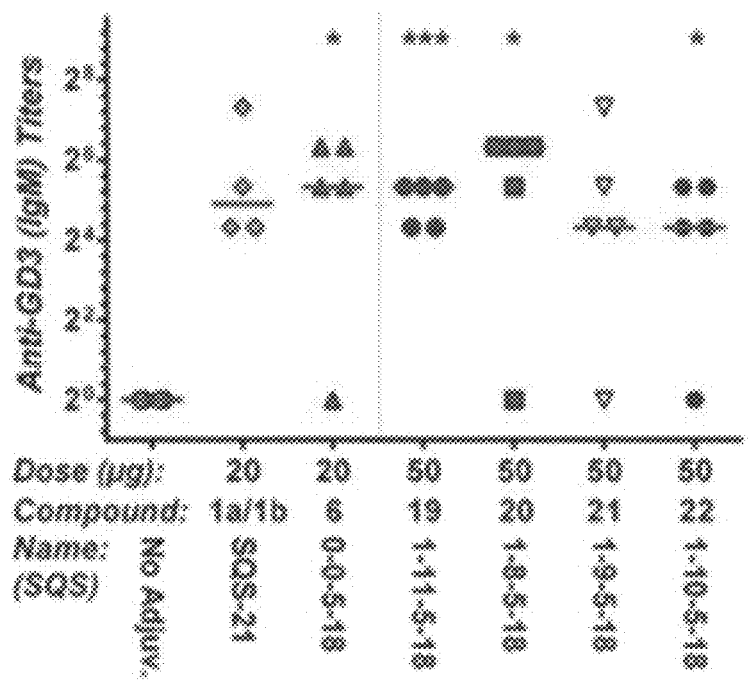
Figure 13:
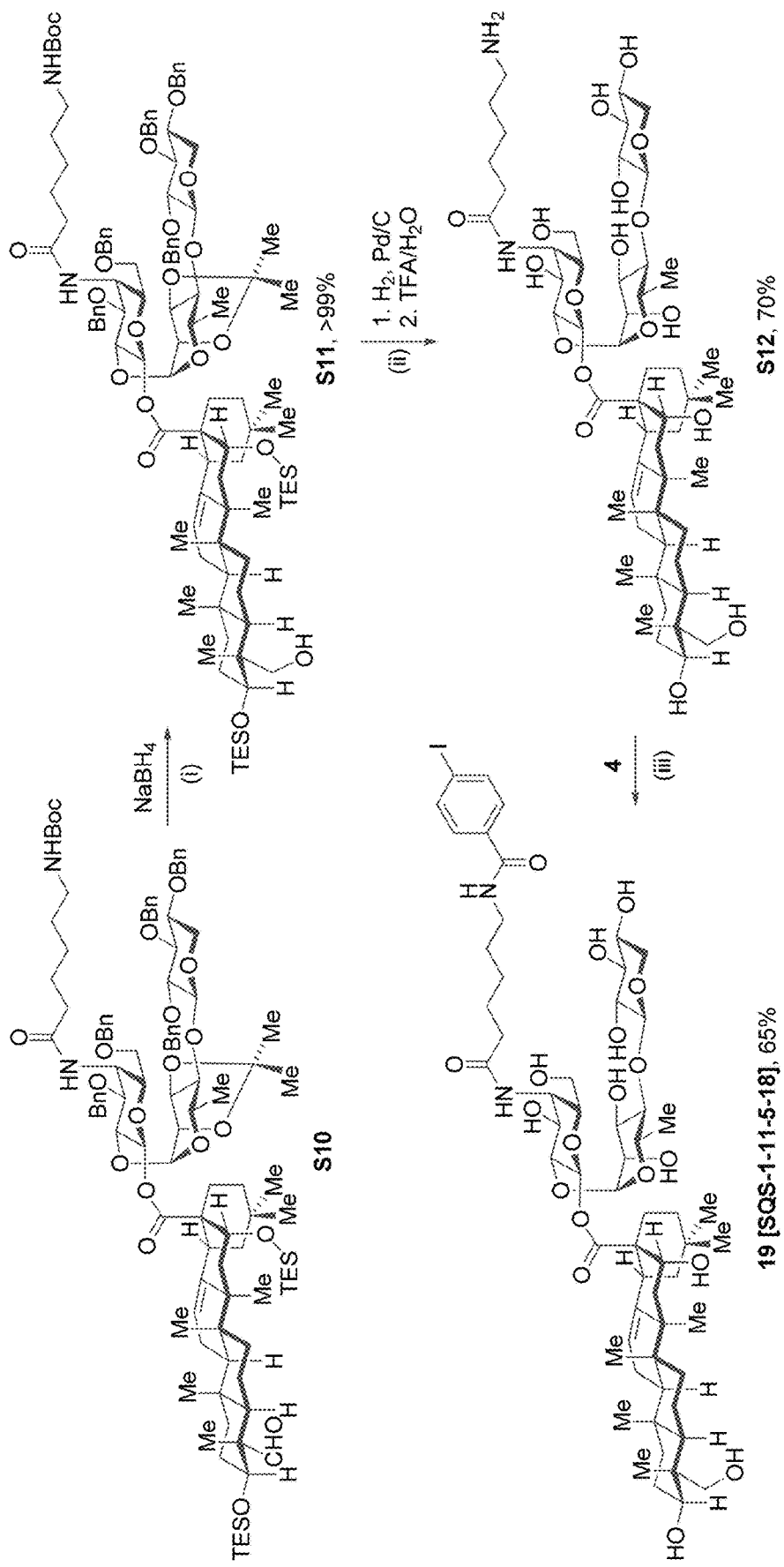
FIG. 13 illustrates synthesis of aryl iodide saponin adjuvant 19 (SQS-1-11-5-18). (i) $NaBH_4$, MeOH, 21° C., 3 h, >99%; (ii) 1. H2 (1 atm), Pd/C (Degussa), EtOH/THF (1:1), 21° C., 12 h; 2. $TFA/H_2O$ (3:1), 0° C., 1.25 h, RP-HPLC, 70% (2 steps); (iii) 4, $Et_3N$, DMF, 21° C., 3 h, RP-HPLC, 65%.
Figure 14:
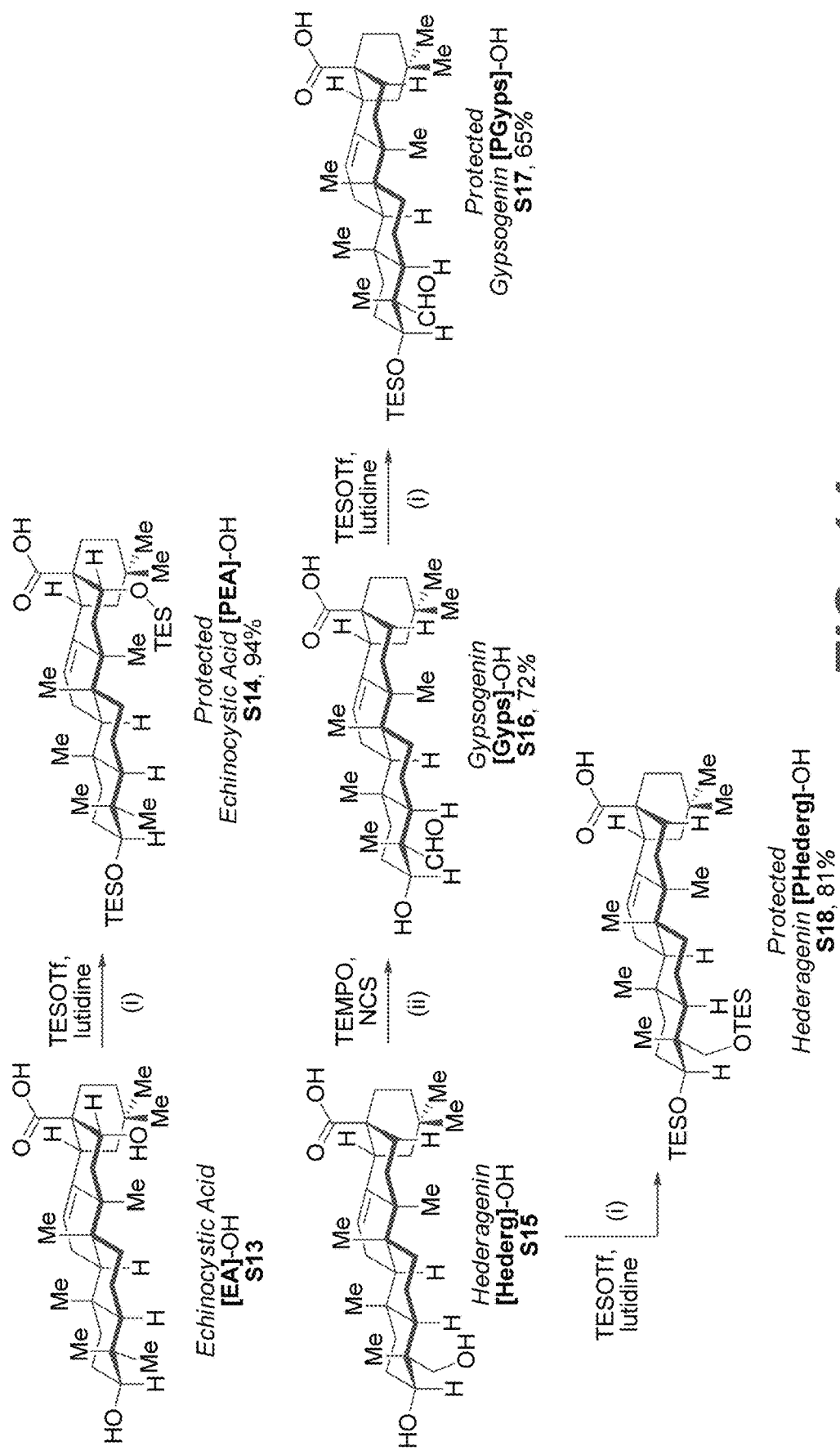
FIG. 14 illustrates synthesis of the protected triterpene building blocks. (i) TESOTf, 2,6-lutidine, $CH_2Cl_2$, 0° C., 1 h; S14: 94%; S17: 65%; S18: 81%; (ii) 2,2,6,6-tetramethylpiperidine 1-oxyl (TEMPO), N-chlorosuccinimide (NCS), tetrabutylammonium chloride hydrate (TBACl·$H_2O$), $CH_2Cl_2/NaHCO_3$ 0.5 M/$K_2CO_3$ 0.05 M, 21° C., 2 h, 72%.
Figure 15:
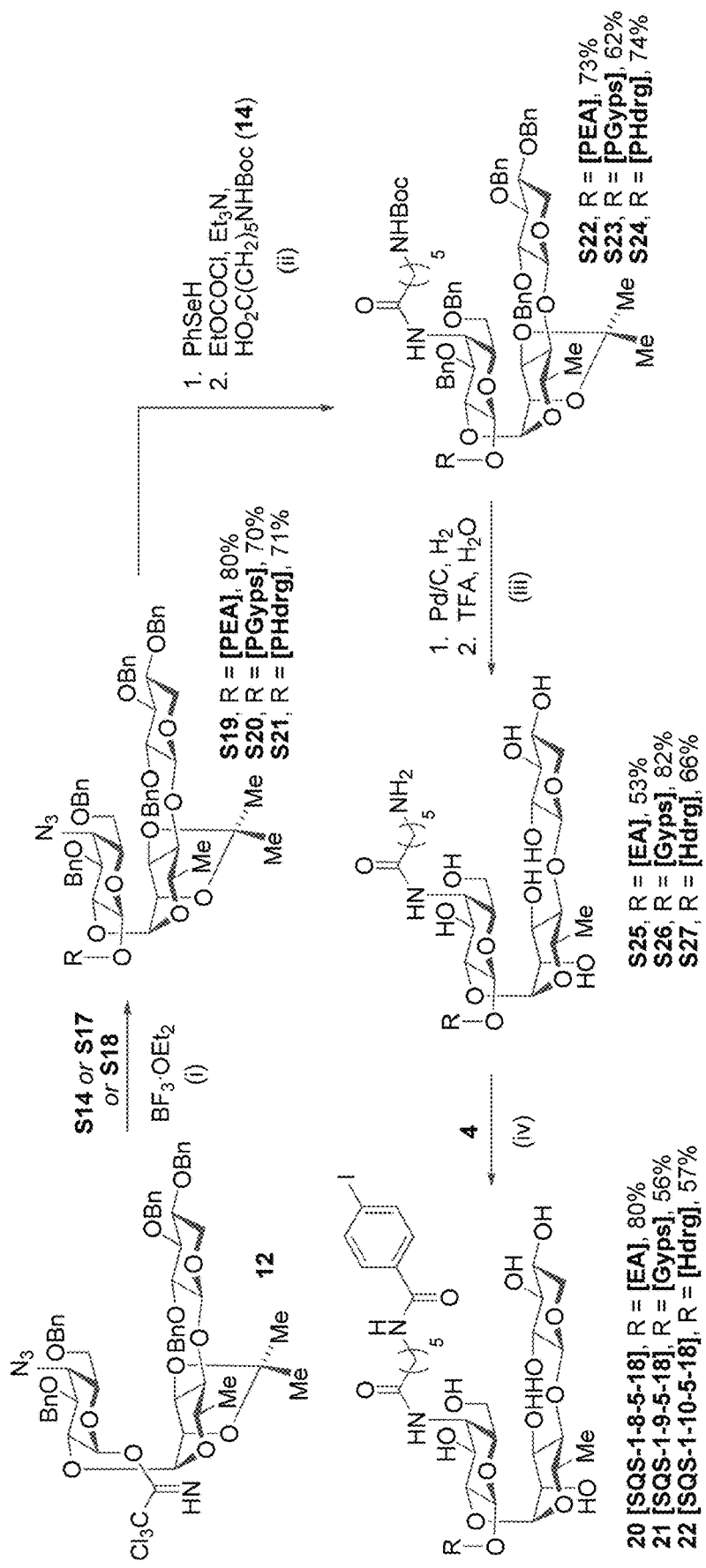
FIG. 15 illustrates synthesis of additional aryl iodide variants lacking the branched trisaccharide domain, 20 (SQS-1-8-5-18), 21 (SQS-1-9-5-18), and 22 (SQS-1-10-5-18). (i) S14 or S17 or S18, BF3·OEt2, 4 Å M.S., $CH_2Cl_2$, −35° C., 30 min; S19: 80%; S20: 70%; S21: 71%; (ii) 1. PhSeH, $Et_3N$, 38° C., 8 h; 2. $HO_2C(CH_2)_5NHBoc$ (14), EtOCOCl, $Et_3N$, THF, 0° C., 2.5 h, [acid preactivation], then, 0° C., 1.5 h; S22: 73% (2 steps); S23: 62% (2 steps); S24: 74%; (iii) 1. H2 (1 atm), Pd/C (Degussa), THF/EtOH (1:1), 21° C., 12 h; 2. $TFA/H_2O$ (3:1), 0° C., 1.25 h, RP-HPLC, S25: 53% (2 steps); S26: 82% (2 steps); S27: 66%; (iv) 4, $Et_3N$, DMF, 21° C., 3 h, RP-HPLC; 20: 80%; 21: 56%; 22: 57%.
Figure 16A:
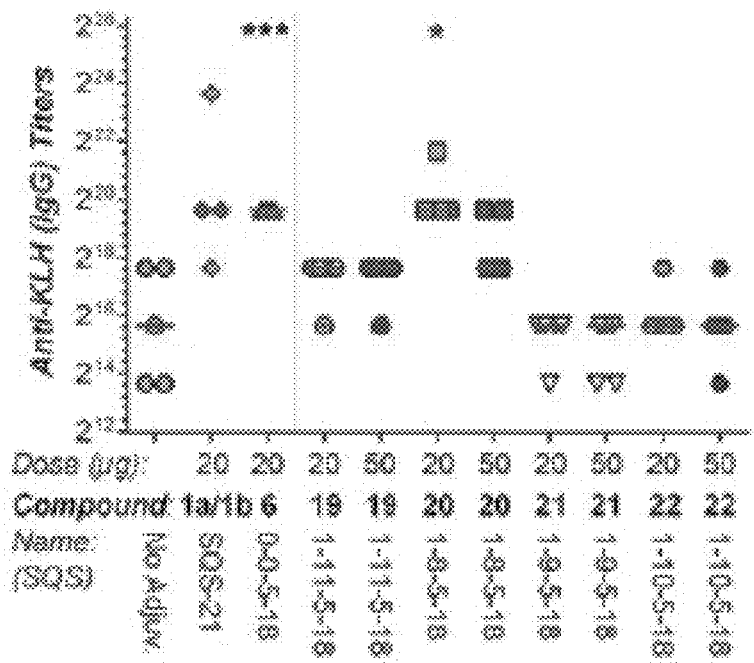
FIGS. 16A to 16F illustrate complete data for evaluation of triterpene variants 19-22 in a preclinical mouse vaccination mode. Biological evaluation of 19 (SQS-1-11-5-18), 20 (SQS-1-8-5-18), 21 (SQS-1-9-5-18), and 22 (SQS-1-10-5-18) at 20 μg and 50 μg doses with a four-component vaccine (MUC1-KLH, OVA, GD3 KLH) for (a) anti-KLH (IgG) (FIG. 16A), (b) anti-MUC1 (IgG) (FIG. 16B), (c) anti-OVA (IgG) (FIG. 16C), (d) anti-GD3 (IgM) (FIG. 16D), and (e) anti-GD3 (IgG) titers (FIG. 16E). Median titers values represented as red horizontal bars. Statistical significance is compared to no adjuvant control and was assessed using two-tailed unpaired Student's t test with CI=99%: *=0.01≤p≤0.05 (significant),=0.001<p<0.01 (very significant),*=p<0.001 (extremely significant).
Figure 16B:
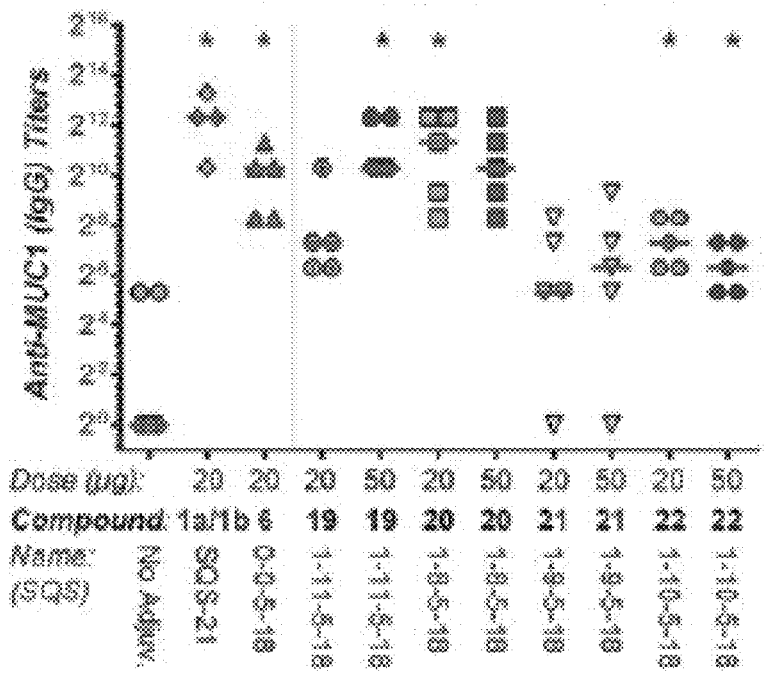
Figure 16C:
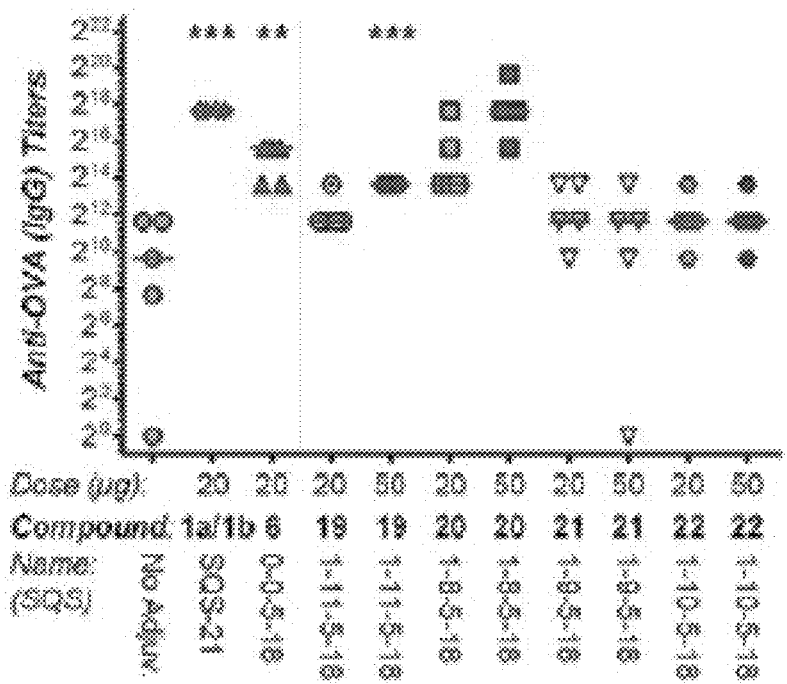
Figure 16D:
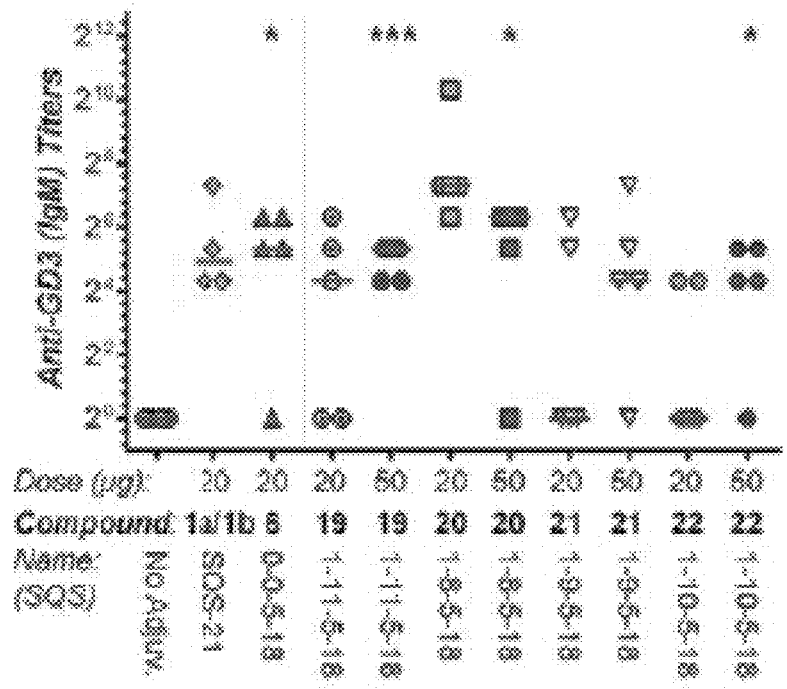
Figure 16E:
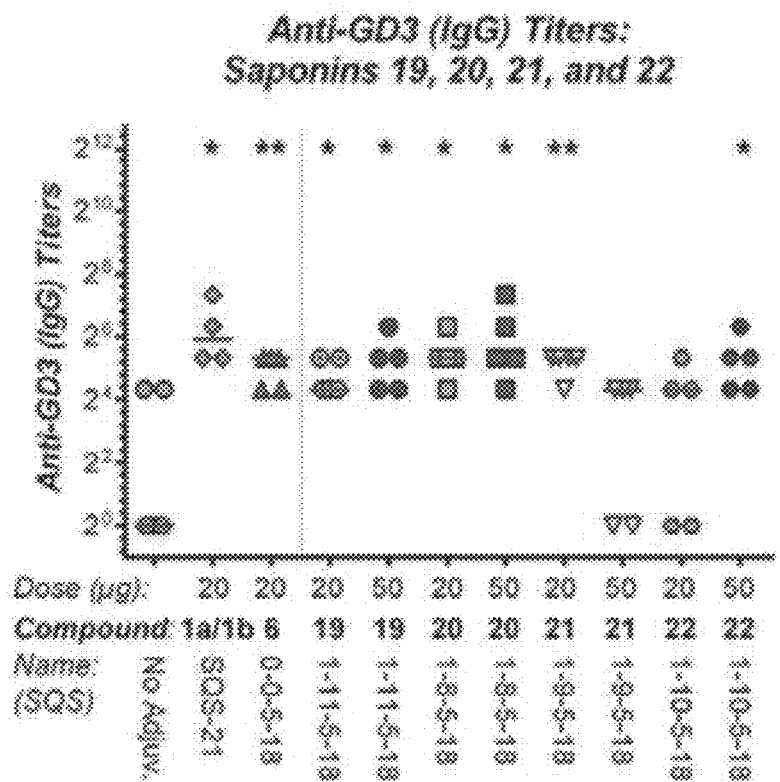
Figure 16F:
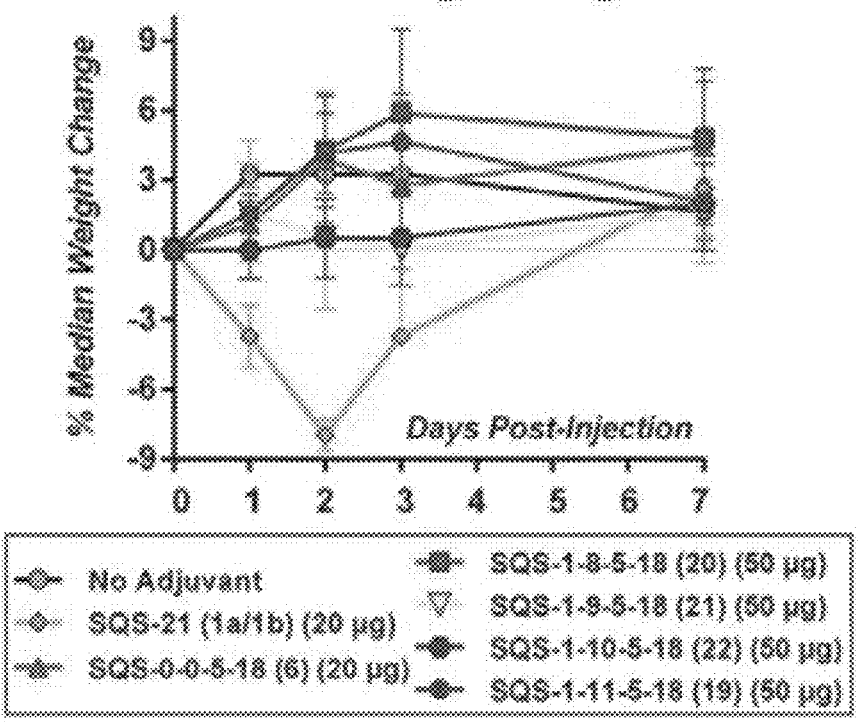

To investigate the importance of each of these functionalities individually, triterpene variants 19-22, in which the oxidation states of the C4-aldehyde substituent and C16-alcohol are varied independently was synthesized (FIG. 5A). Caulophyllogenin variant 19 (SQS-1-11-5-18), in which the C4-aldehyde substituent is reduced to a hydroxymethyl group while the C16-alcohol is retained, was accessed from an advanced intermediate in the synthesis of 16 (SQS-1-0-5-18) (FIG. 13). Echinocystic acid variant 20 (SQS-1-8-5-18), in which the C4-aldehyde substituent is replaced by a methyl group while the C16-alcohol is again retained, and hederagenin variant 22 (SQS-1-10-5-18), in which the C4-aldehyde substituent is replaced by a hydroxymethyl group and the C16-alcohol is replaced by a proton, were prepared from the corresponding, commercially available triterpenes (FIG. 14 and FIG. 15). Gypsogenin variant 21 (SQS-1-9-5-18), which possesses the C4 aldehyde substituent but lacks the C16-alcohol, was accessed via initial TEMPO oxidation of the C4-hydroxymethyl substituent in hederagenin to afford gypsogenin.

These saponin variants were evaluated with a four-component vaccine comprised of MUC1-KLH, OVA, and the poorly immunogenic glycolipid GD3 (melanoma, neuroblastoma, sarcoma antigen) conjugated to KLH (GD3-KLH) (FIGS. 5B-E; see FIG. 16 for full data with both 20 and 50 μg doses). Echinocystic acid derivative 20 (C4-Me, C16-OH), induced the highest antibody responses to all four antigens, comparable to or higher than those of the complete, branched trisaccharide-containing saponin 6 and SQS-21. Caulophyllogenin derivative 19 (C4-$CH_2OH$, C16-OH) afforded antibody titers slightly below those of echinocystic acid derivative 20, branched trisaccharide-containing saponin 6, and SQS-21, albeit only at elevated doses (50 μg). In contrast, gypsogenin derivative 21 (C4-CHO, C16-H) and hederagenin derivative 22 (C4-$CH_2OH$, C16-H), both generated lower antibody responses in all cases except the anti-GD3 IgG response, and similar to the no adjuvant treated controls for KLH and OVA.

Figure 5F:
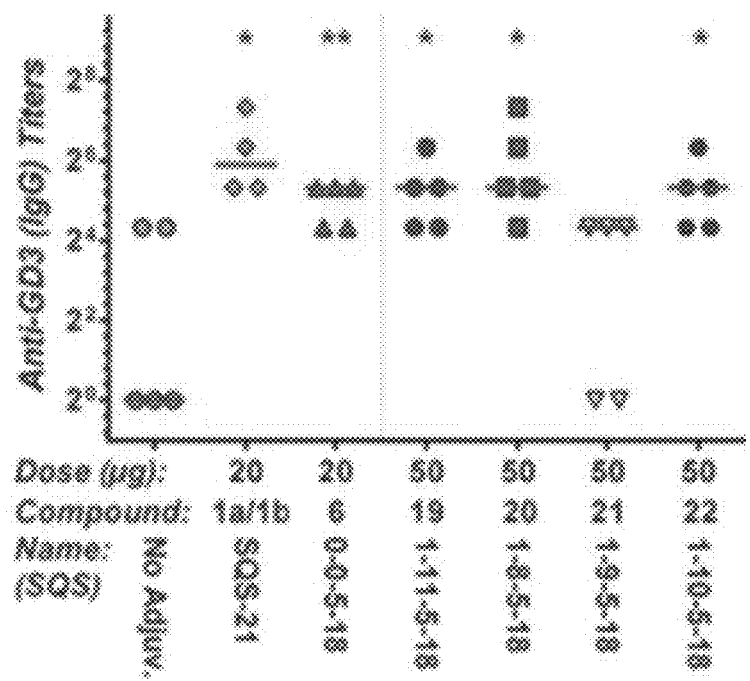
Figure 5G:
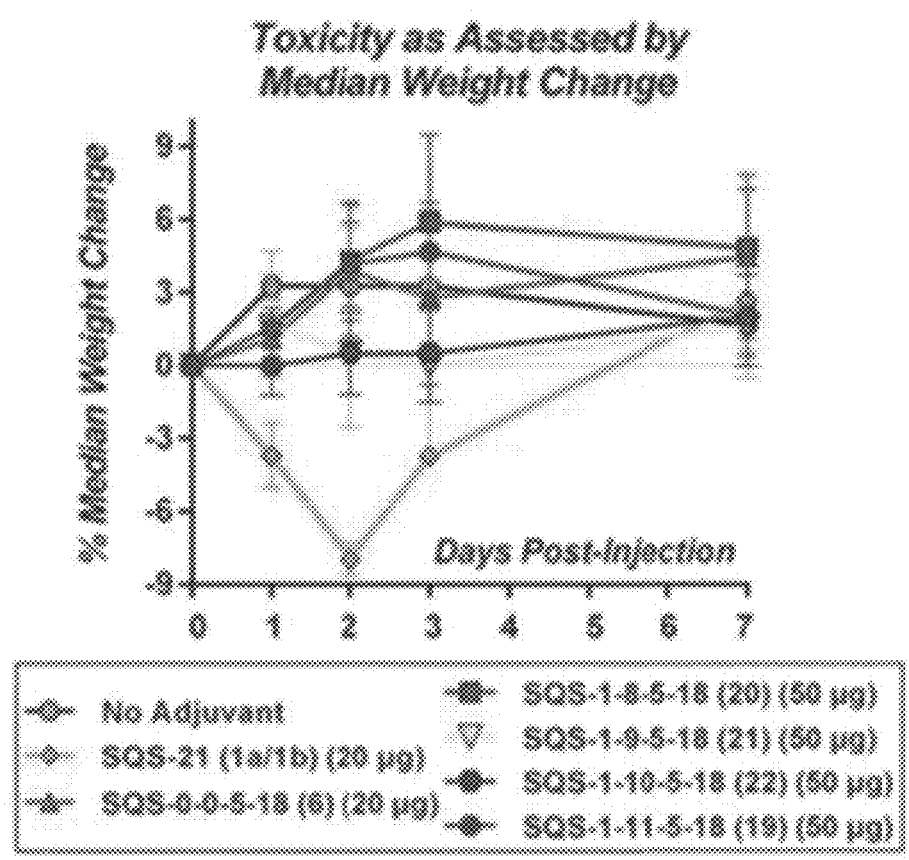

Antibody subtyping of the anti-MUC1 and anti-OVA IgG isotypes revealed a significant bias toward the mouse IgG1 and IgG2b subtype with both of the adjuvant active saponins in this group (19, 20). Similar results were obtained with SQS-21 and with the parent quillaic acid derivative 16. Production of other mouse IgG subtypes, including IgG2a and IgG3, was low or negligible, as indicated by class-specific ELISA. Toxicity remained drastically lower for all four variants compared to NQS-21 and SQS-21 (FIG. 5f).

Thus, echinocystic acid derivative 20 provides immunostimulatory activity generally rivaling that of SQS-21 but without the associated toxicity. Caulophyllogenin derivative 19 also provides antibody responses similar to the complete, branched trisaccharide-containing saponin 6, although higher doses are required. Importantly, both echinocystic acid derivative 20 and caulophyllogenin derivative 19 lack the C4-aldehyde substituent but retain the C16-alcohol. In contrast, gypsogenin derivative 21 and hederagenin derivative 22 both lack the C16-alcohol and induced lower antibody responses to all antigens tested. Taken together, these data indicate that the C4-aldehyde substituent is not required for potent immunoadjuvant activity in these novel saponins and reveal a previously unappreciated role for the C16-alcohol in enhancing activity.

Example 5: Biodistribution of Truncated Saponins $[^{131}I]^{-16}$ and $[^{131}I]^{-18}$ Groups of five mice (naive, C57BL/6J female, 8-10 weeks of age) were injected subcutaneously with the radioiodinated saponin adjuvants of interest (~25 mCi), the corresponding non-radiolabeled saponin (20 mg), and OVA (20 mg) in PBS (150 mL). Mice were sacrificed at 24 h, 72 h, and 96 h post-injection. Tissues and organs were harvested and analyzed for distribution of radioactivity normalized to the weight of the organ (% ID/g, percent injected dose per gram). Statistical significance of the difference in recoveries (% ID/g) for the active and attenuated adjuvant was assessed for each tissue or organ using two-tailed unpaired Student's t-test with CI=95%. In initial experiments, biodistribution profiles did not change substantially between 24 and 96 h post-injection, and the 24 h time-point was used for the subsequent experiments.

Three mice were shaved and immunized in the left flank with 10 μg of active adjuvant 3 (SQS-0-0-5-12) or inactive adjuvant 2 (SQS-0-0-5-11) and 20 μg of Alexa-647-conjugated OVA (OVA-A647) in PBS (100 μL). Whole-body imaging was performed at 24 h post-injection with a Maestro Imaging System. At 24 h post-injection, mice were sacrificed and the left and right lymph nodes were dissected and imaged separately.

Figure 2A:
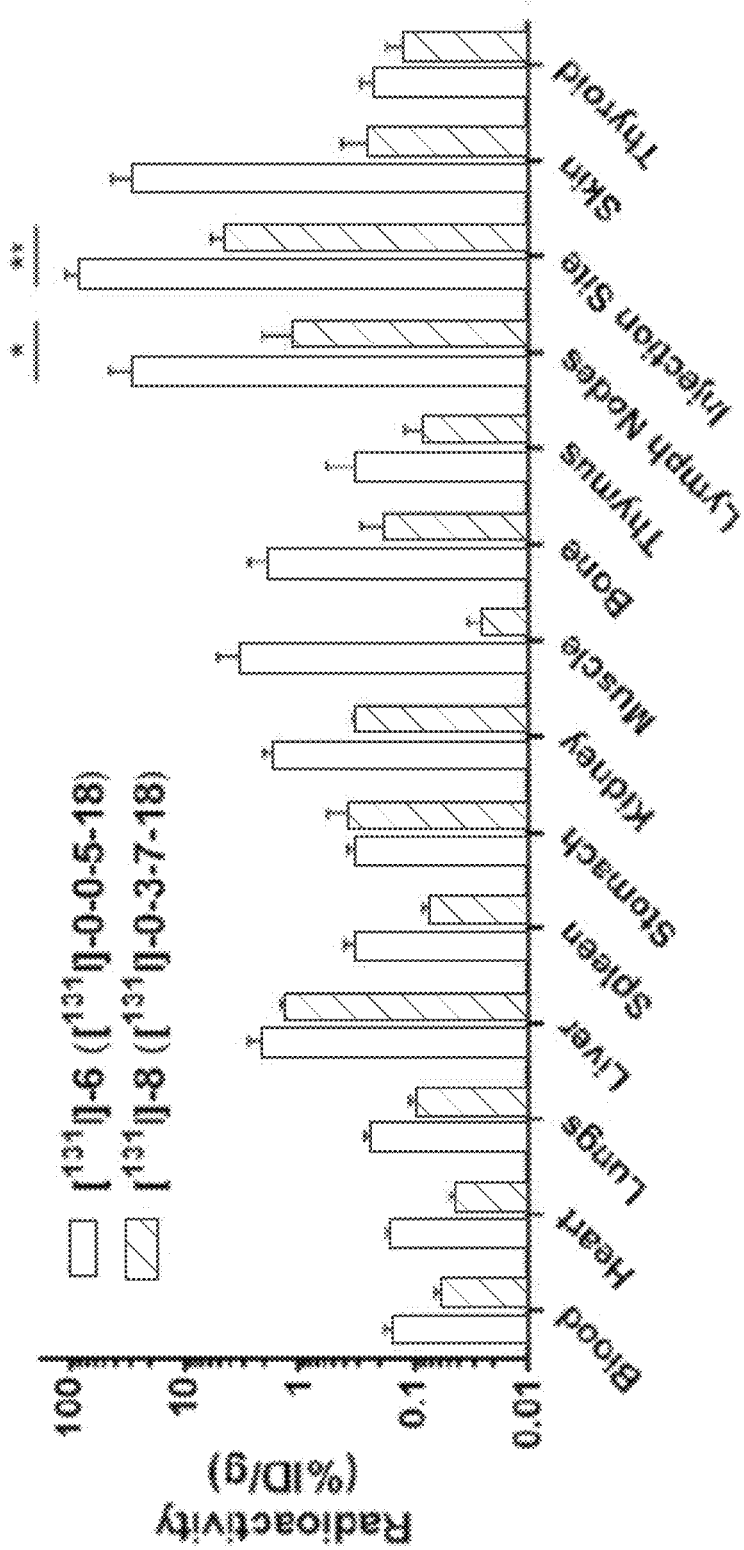
FIGS. 2A to 2C illustrate various radioiodinated saponin [131I]-6 and fluorescent saponin 3 localize to lymph nodes and injection site in mice.
Figure 2B:
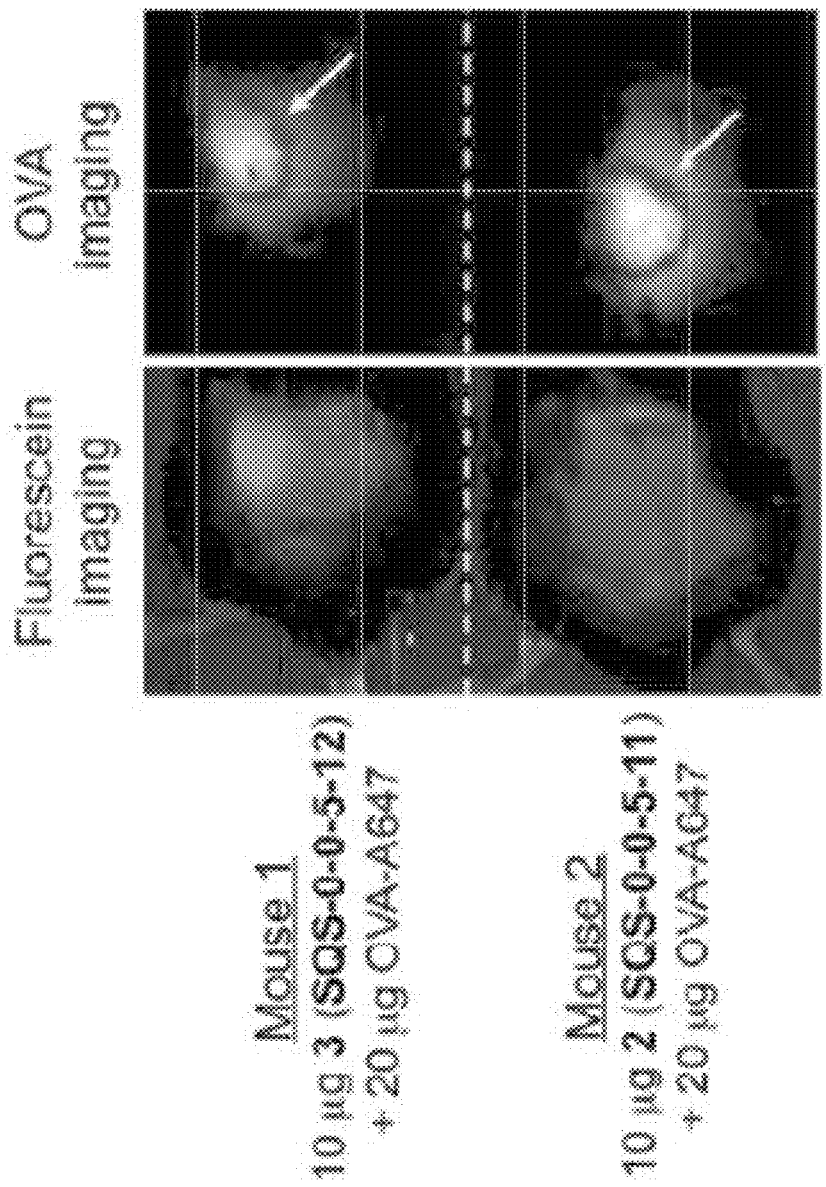
Figure 2C:
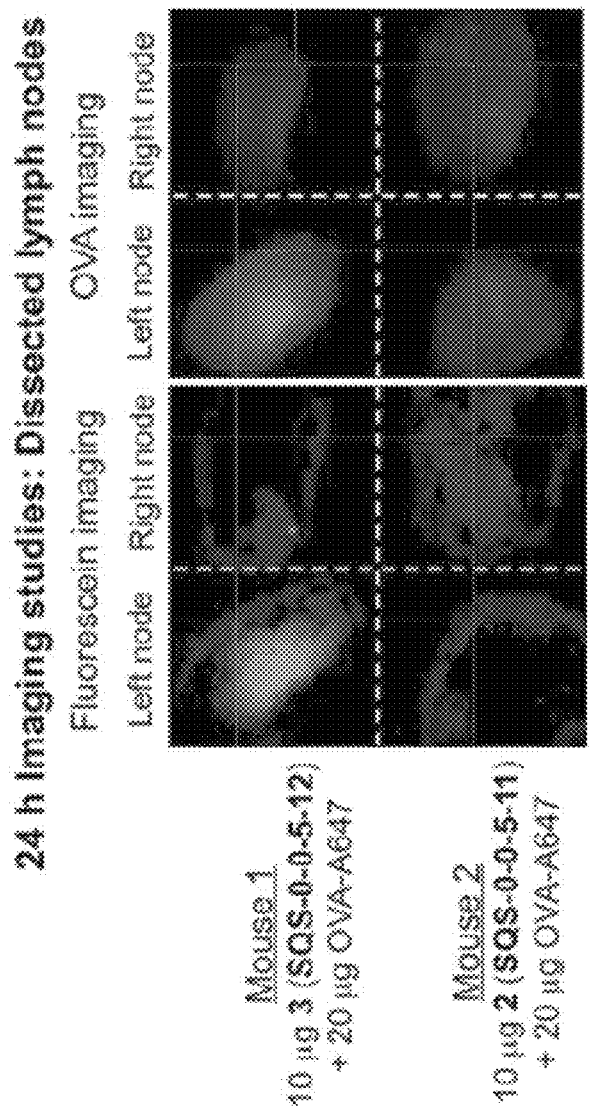
Figure 6:
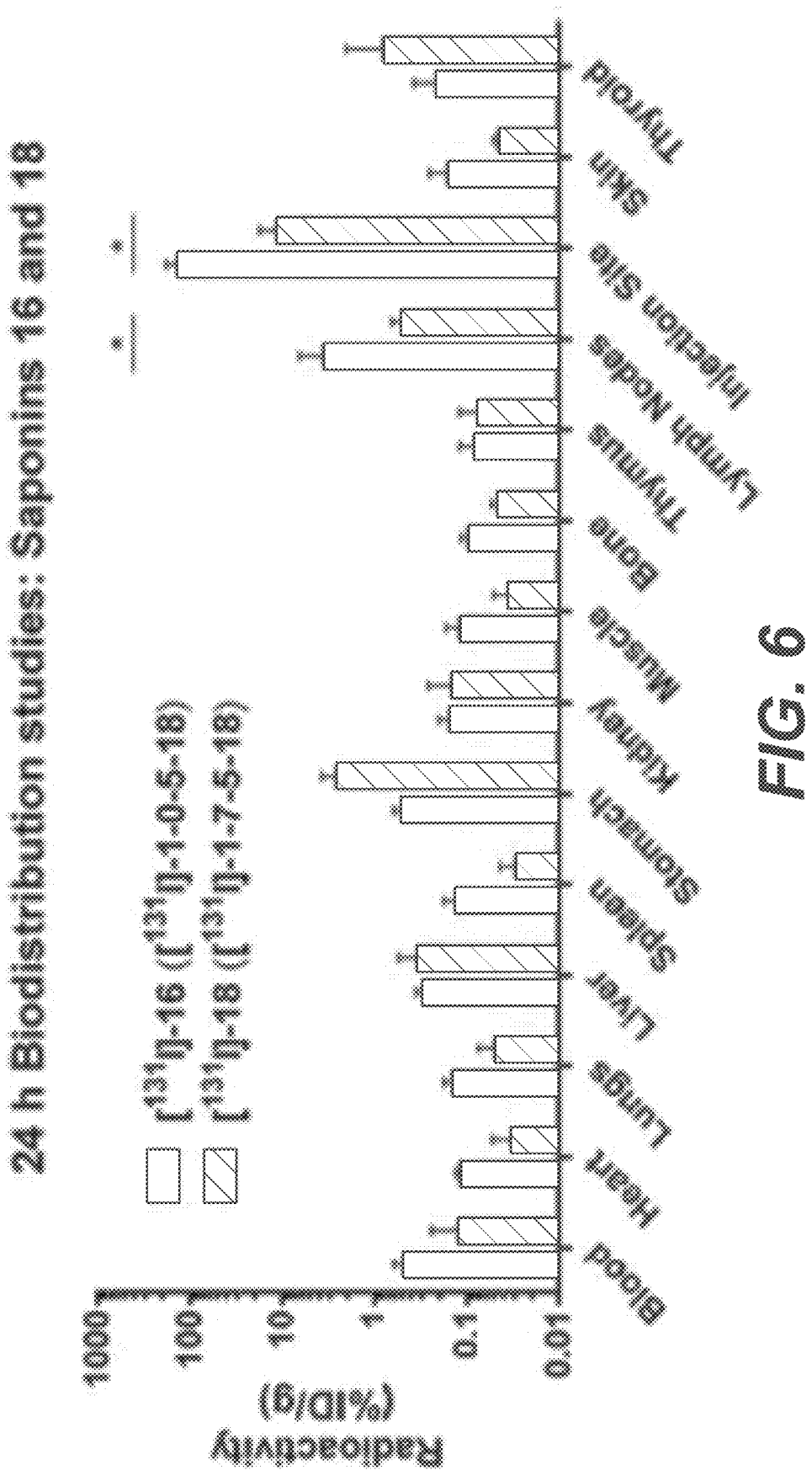
FIG. 6 illustrates adjuvant-active quillaic acid derivative 16 localizes to the injection site and lymph nodes in mice while adjuvant-attenuated oleanolic acid derivative 18 does not. In vivo biodistribution in mice of active adjuvant $[^{131}I]-16$ ($[^{131}I]$-SQS-1-0-5-18) and attenuated adjuvant $[^{131}I]-18$ ($[^{131}I]$-SQS-1-7-5-18) at 24 h post-injection in the presence of 20 μg of OVA; error bars indicate standard deviation from mean for five mice; statistical significance indicated graphically only for lymph nodes and injection site for clarity: *=p≤0.05: lymph nodes, injection site, skin; =p<0.01: lungs, spleen, stomach, muscle, bone; *=p<0.001: blood, heart.

The in vivo biodistribution patterns of the adjuvant-active truncated quillaic acid variant 16 (SQS-1-0-5-18) were compared and the adjuvant-attenuated oleanolic acid derivative 18 (SQS-1-7-5-18), using the radioiodinated congeners $[^{131}I]^{-16}$ (FIG. 3A) and $[^{131}I]^{-18}$ (FIG. 12), to enable correlation with the earlier studies of the active/attenuated adjuvant pair 6 (SQS-0-0-5-18) and 8 (SQS-0-3-7-18) (FIG. 2A). The active adjuvant $[^{131}I]^{-16}$ showed significantly higher localization at the injection site (136% ID/g) and within the lymph nodes (3.55% ID/g) compared to $[^{131}I]^{-18}$ (11.5% and 0.50% ID/g, respectively) (FIG. 6). Accordingly, in both biodistribution studies, the more active adjuvant was preferentially retained at the site of injection and accumulated in the lymph nodes, providing a positive correlation between this biodistribution pattern and adjuvant activity.

Example 7: Synthesis of Iodinated and Radiolabeled Saponin Adjuvants

Synthesis of Initial Variants 6 (SOS-0-0-5-18) and 8 (SOS-0-3-7-18)

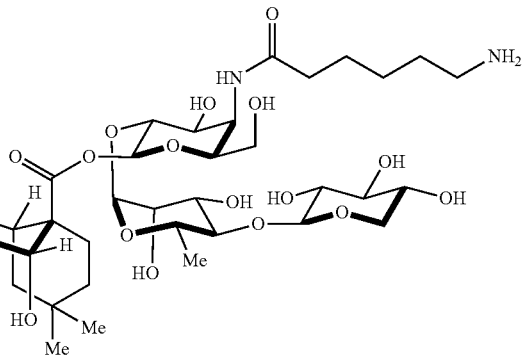

2

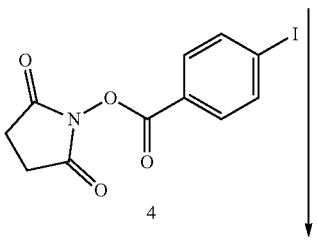

4

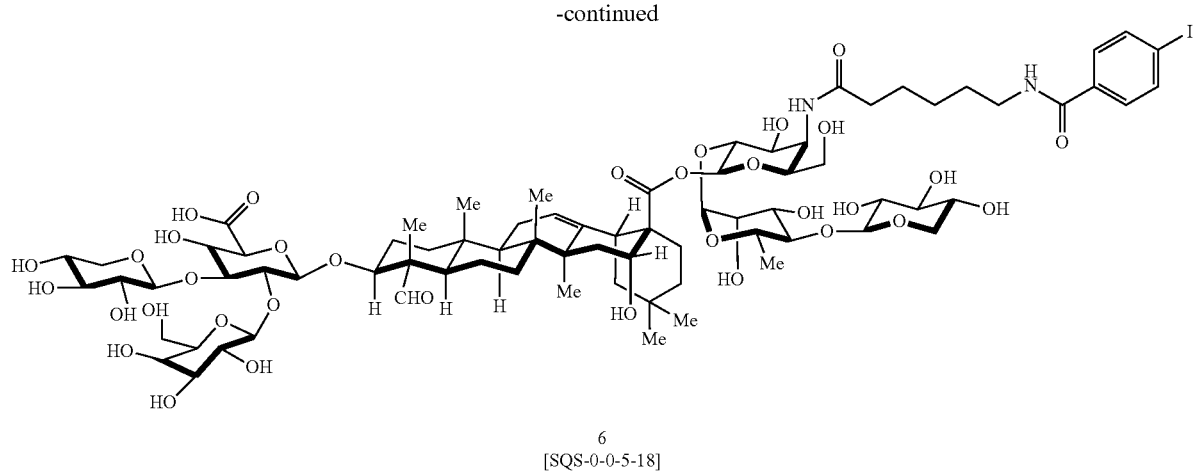

6
[SQS-0-0-5-18]

SQS-0-0-5-18 (6). (EC-V-056) To a solution of amine 2 (see Chea, E. K. et at. Synthesis and preclinical evaluation of QS-21 variants leading to simplified vaccine adjuvants and mechanistic probes. *J. Am. Chem. Soc.* 134, 13448-13457 (2012)) (9.0 mg, 6.0 μmol, 1.0 equiv) in N,N'-dimethylformamide (2.0 mL), triethylamine (50 μL, 0.36 mmol, 60 equiv) was injected and the mixture stirred at 21° C. for 50 min. Aryl iodide 4 (see (a) Zhi, Y.-G. et al. Systematic studies on photoluminescence of oligo(arylene-ethynylene)s; tunability of excited states and derivatization as luminescent labeling probes for proteins. *Eur. J. Org. Chem.* 3125-3139 (2006); (b) Shell, T. A., Mohler, D. L. Selective targeting of DNA for cleavage within DNA-histone assemblies by a spermine-[CpW(CO)₃Ph]₂ conjugate. *Org. Biomol. Chem.* 3, 3091-3093 (2005)) (20 mg, 60 μmol, 10 equiv) in N,N'-dimethylformamide (0.6 mL) was then added dropwise and the reaction stirred at 21° C. for 1 h. The contents were diluted with 20% acetonitrile/water (10 mL) and directly purified by RP-HPLC on an XBridge Prep BEH300 C18 column (5 μm, 10×250 mm) using a linear gradient of 20-70% acetonitrile/water, over 30 min, at a flow rate of 5 mL/min. SQS-0-0-5-18 (6) (5.4 mg, 52% yield) was obtained as a white powder after lyophilization.

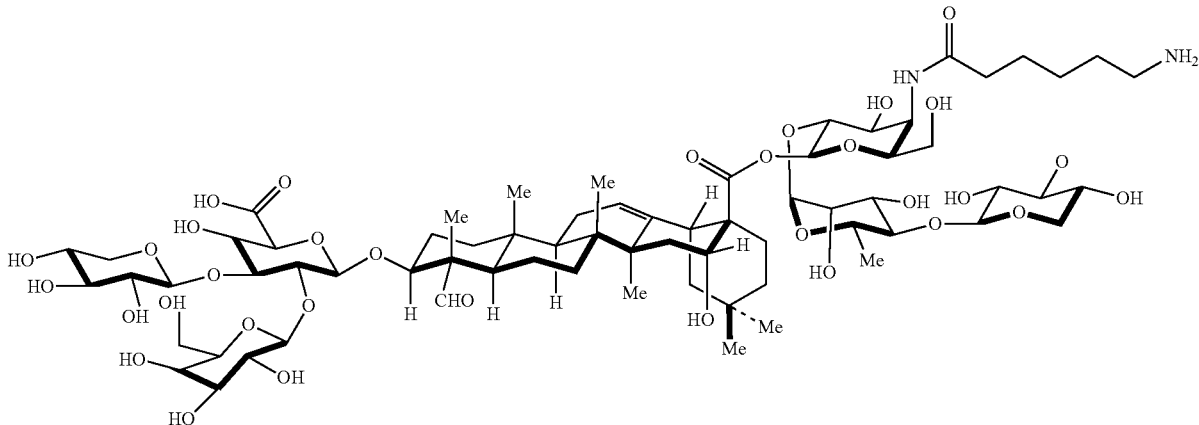

2

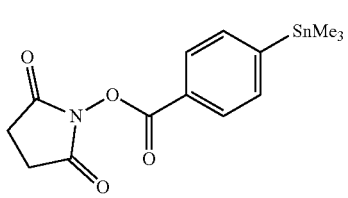

5

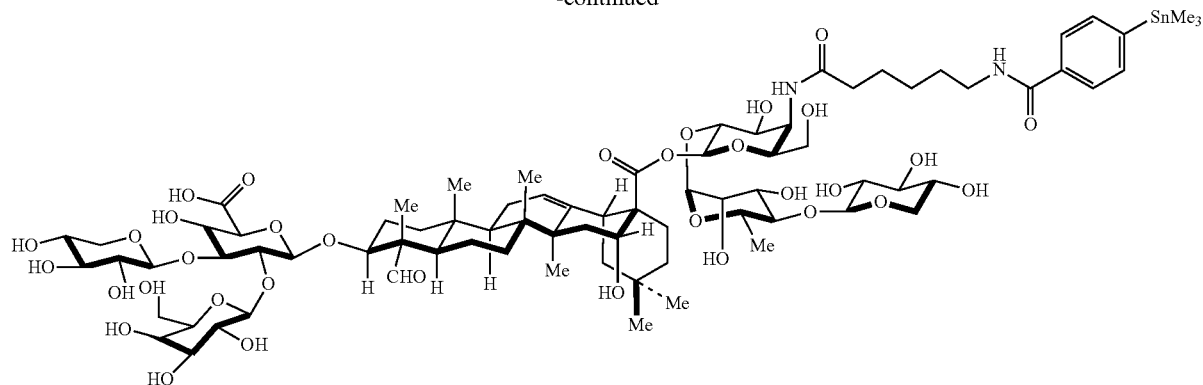

7

Aryl tin precursor to [¹³¹I]-SQS-0-0-5-18 (7). (EC-V-052) To a solution of amine 2 (2.0 mg, 1.3 μmol, 1.0 equiv) in N,N'-dimethylformamide (0.9 mL) triethylamine (10 μL, 72 mol, 55 equiv) was injected and the mixture stirred at 21° C. for 50 min. Aryl tin 5 (Koziorowski, J., Henssen, C., Weinreich, R. A new convenient route to radioiodinated Nsuccinimidyl 3- and 4-iodobenzoate, two reagents for radioiodination of proteins. *Appl. Radiat. Isot.* 49, 955-959 (1998)) (2.0 mg, 5.2 μmol, 4.0 equiv) in N,N'-dimethylformamide (0.2 mL) was then added dropwise and the reaction stirred at 21° C. for 1 h. After this time, the contents were diluted with 20% acetonitrile/water (10 mL), and directly purified by RP-HPLC on an XBridge Prep BEH300 C18 column (5 μm, 10×250 mm) using a 20-70% acetonitrile/water linear gradient, over 30 min, at a flow rate of 5 mL/min. Saponin 7 (1.8 mg, 78% yield) was obtained as a white powder after lyophilization.

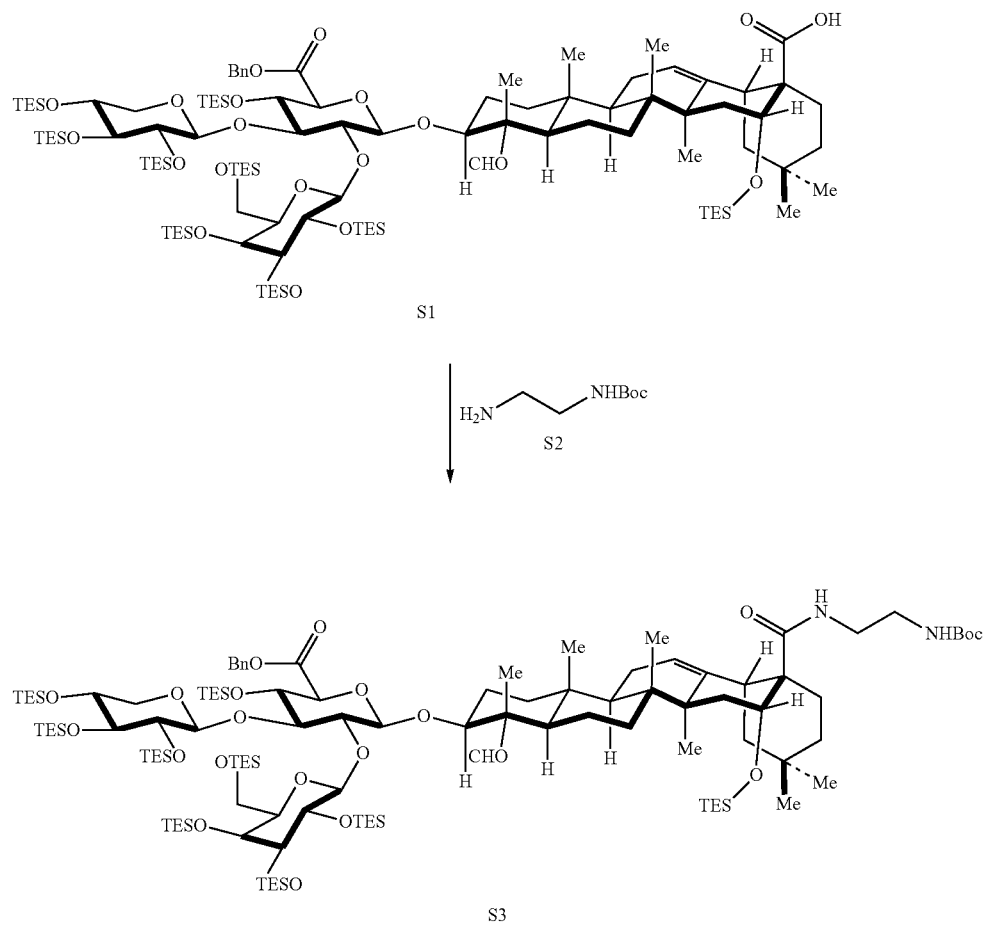

Fully protected aminoacyl prosapogenin S3. (EC-V-191) A solution of acid S1 (Deng, K.,

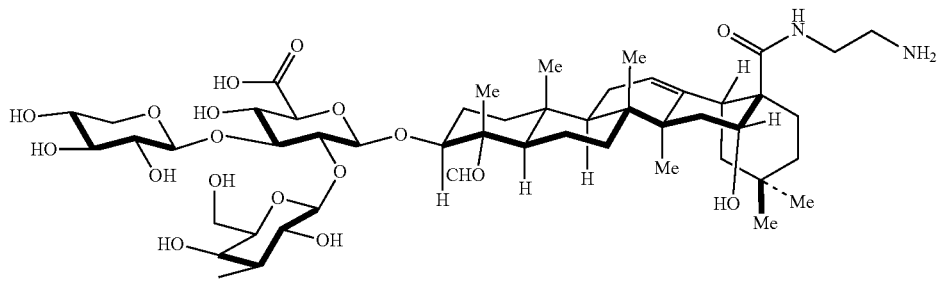

S4

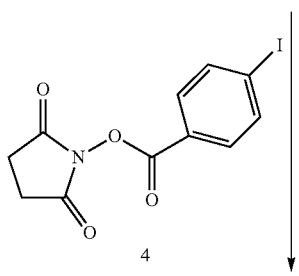

4

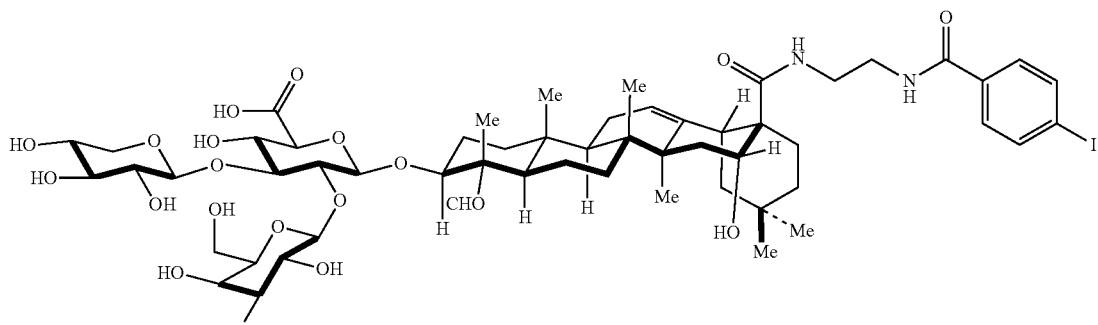

8
[SQS-0-3-7-18]

SQS-0-3-7-18 (8). (EC-IV-194) To a solution of S4 (7.1 mg, 7.1 μmol, 1.0 equiv) in N,N'-dimethylformamide (0.4 mL) was injected triethylamine (20 μL, 0.14 mmol, 20 equiv), followed by dropwise addition of 4 (14 mg, 40.6 μmol, 5.7 equiv) in N,N'-dimethylformamide (0.4 mL). After stirring for 3 h, the contents were diluted with 10 mL water (0.05% TFA) and purified by RP-HPLC on an XBridge Prep BEH300 C18 column (5 μm, 10×250 mm) using a linear gradient of 30-80% acetonitrile/water (0.05% TFA), over 30 min, at a flow rate of 5 mL/min. SQS-0-3-7-18 (8) (5.9 mg, 68% yield) eluted as a single peak and existed as a white powder after lyophilization.

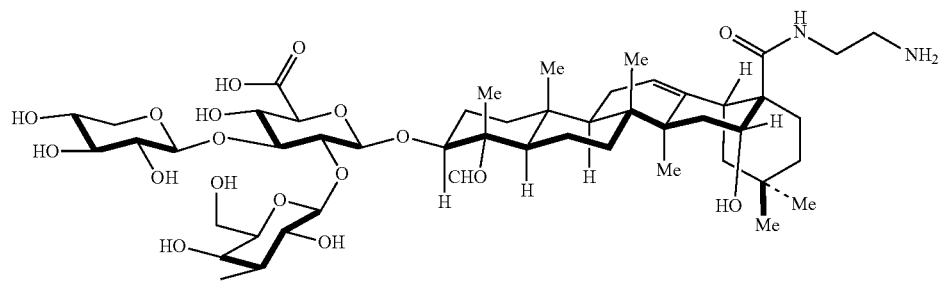

S4

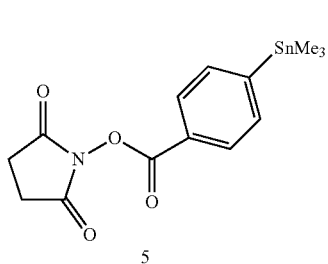

5

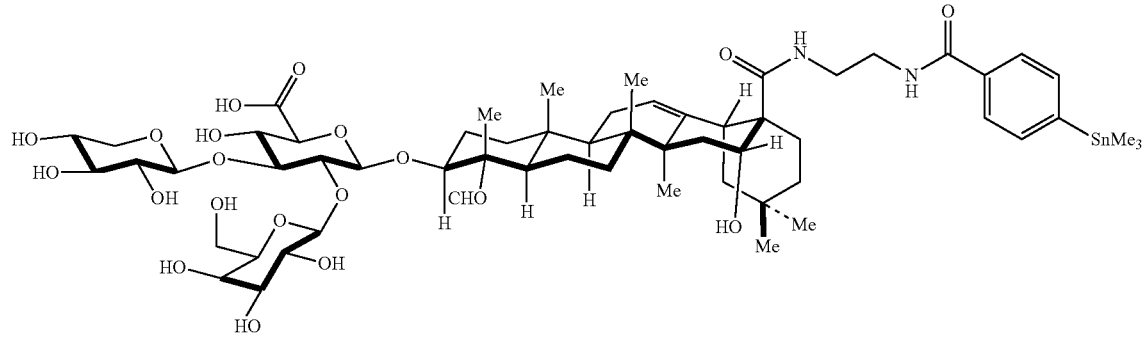

9

Aryl tin precursor to [$^{131}$I]-SQS-0-3-7-18 (9). (EC-IV-193) To S4 (3.6 mg, 3.6 µmol, 1.0 equiv) dissolved in N,N'-dimethylformamide (0.2 mL) with triethylamine (20 µL, 0.14 mmol, 40 equiv) was added dropwise a solution of 5 (5 mg, 13.1 µmol, 3.6 equiv) in N,N'-dimethylformamide (0.1 mL). After stirring for 2.5 h, the contents were diluted with water (4 mL) and purified via RP-HPLC on an XBridge Prep BEH300 C18 column (5 µm, 10×250 mm) using a 20-95% acetonitrile/water linear gradient, over 30 min, at a flow rate of 5 mL/min. Saponin 9 (2.4 mg, 53% yield) eluted as a single peak and was obtained as a white powder after lyophilization.

Synthesis of Variant Lacking the Branched Trisaccharide Domain (16)

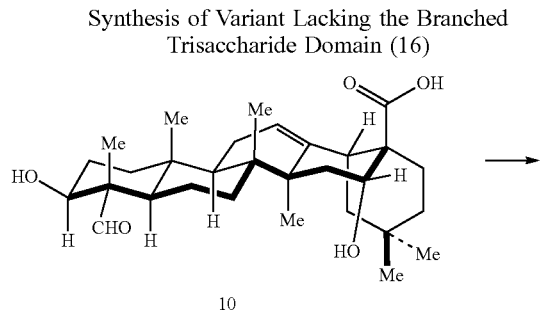

10

-continued

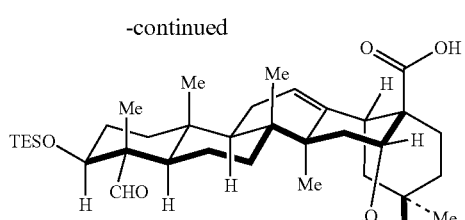

11

Bis(silyl ether) of quillaic acid (11). (AFT-II-040) A suspension of quillaic acid 10 (200 mg, 0.41 mmol, 1.0 equiv) in CH$_2$Cl$_2$ (20 mL) was cooled in an ice bath and 2,6-lutidine (0.48 mL, 4.1 mmol, 10 equiv) and triethylsilyl trifluoromethanesulfonate (0.46 mL, 2.06 mmol, 5.0 equiv) were injected. After stirring for 1 h, the contents were washed with saturated NaHCO$_3$ (10 mL), the aqueous phase was extracted with CH$_2$Cl$_2$ (2×15 mL) and the combined organics were dried over Na$_2$SO$_4$, filtered, and concentrated. The crude product was purified by silica gel chromatography (hexanes to 4:1 hexanes/EtOAc) to afford 11 (235 mg, 80% yield).

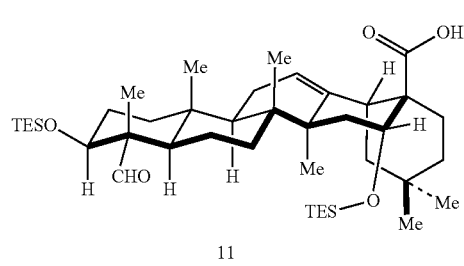
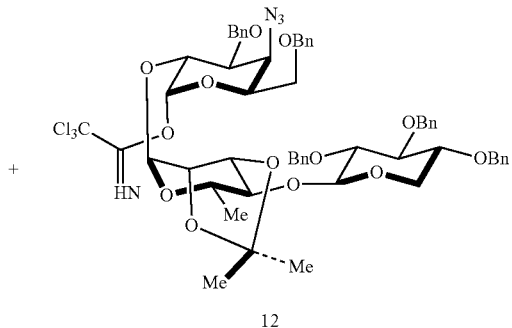

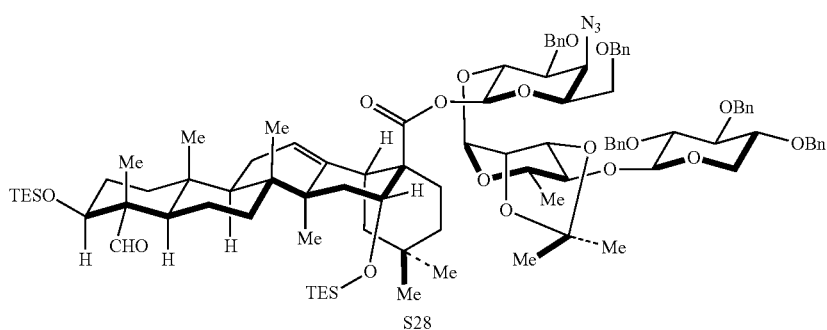

Protected quillaic acid saponin azide S28. (AFT-I-165) To a solution of 11 (38 mg, 49 μmol, 1.05 equiv) and imidate 12 (52 mg, 47 μmol, 1.0 equiv) in $CH_2Cl_2$ (7 mL) 80 mg powdered 4 Å molecular sieves was added and the mixture was stirred at 21° C. for 30 min. The reaction schlenk was then cooled to −35° C. and boron trifluoride diethyletherate (1.2 μL, 9.0 μmol, 0.2 equiv) was injected. The mixture was stirred for 0.5 h at this temperature, quenched with 0.2 mL of triethylamine and concentrated. Purification of the residue by silica gel chromatography (0.2% triethylamine in benzene to 97:3 benzene/EtOAc) gave a colorless oil that was further chromatographed to afford the desired product S28 (56 mg, 72% yield) as a white solid.

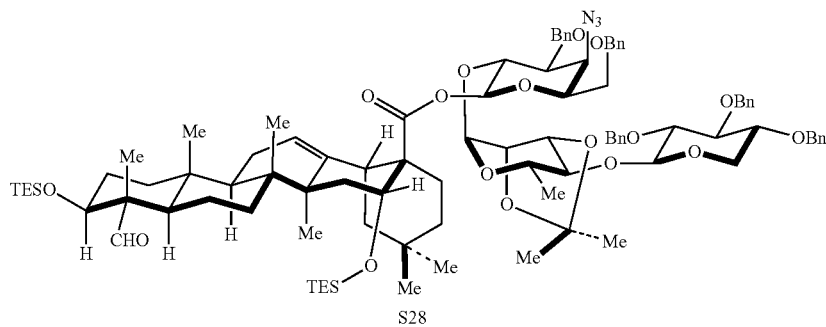

-continued

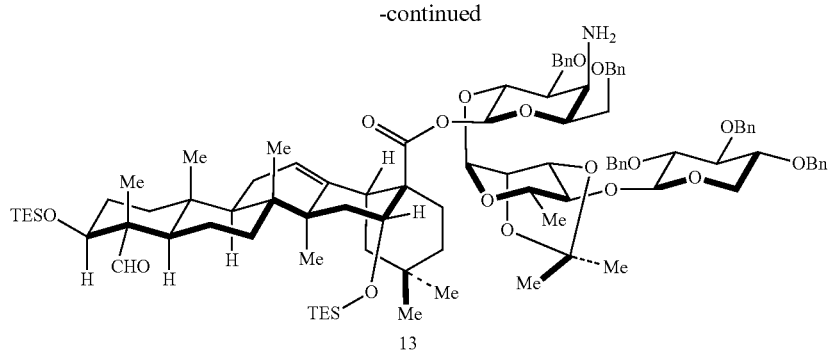

13

Protected quillaic acid saponin amine 13. (AFT-I-167) To S28 (62 mg, 37 μmol, 1.0 equiv) dissolved in triethylamine (28 mL) was added a freshly prepared solution of phenyl selenol (1.11 mmol, 30 equiv) via cannula. Upon addition of phenyl selenol a white precipitate was formed and the solution became bright yellow. The reaction was stirred for 8 h at 38° C. and the solution was then concentrated to afford a yellow-white solid. The crude mixture was purified by silica gel chromatography (90:10 to 85:15 benzene/EtOAc to afford the amine 13 (49 mg, 80% yield) as a glassy solid.

triethylamine (213 μL, 1.53 mmol, 90 equiv) followed by ethyl chloroformate (16.0 μL, 0.17 mmol, 10.0 equiv). The turbid, white solution was stirred for 2.5 h at 0° C. and then added via cannula to amine 13 (28 mg, 17.0 μmol, 1.0 equiv) at 0° C. The reaction mixture was stirred at this temperature for 1.5 h and then quenched with water (0.2 mL) to give a clear solution. The contents were diluted with saturated NaHCO$_3$ (30 mL), and the aqueous phase was extracted with CH$_2$Cl$_2$ (3×25 mL). The combined organics were dried

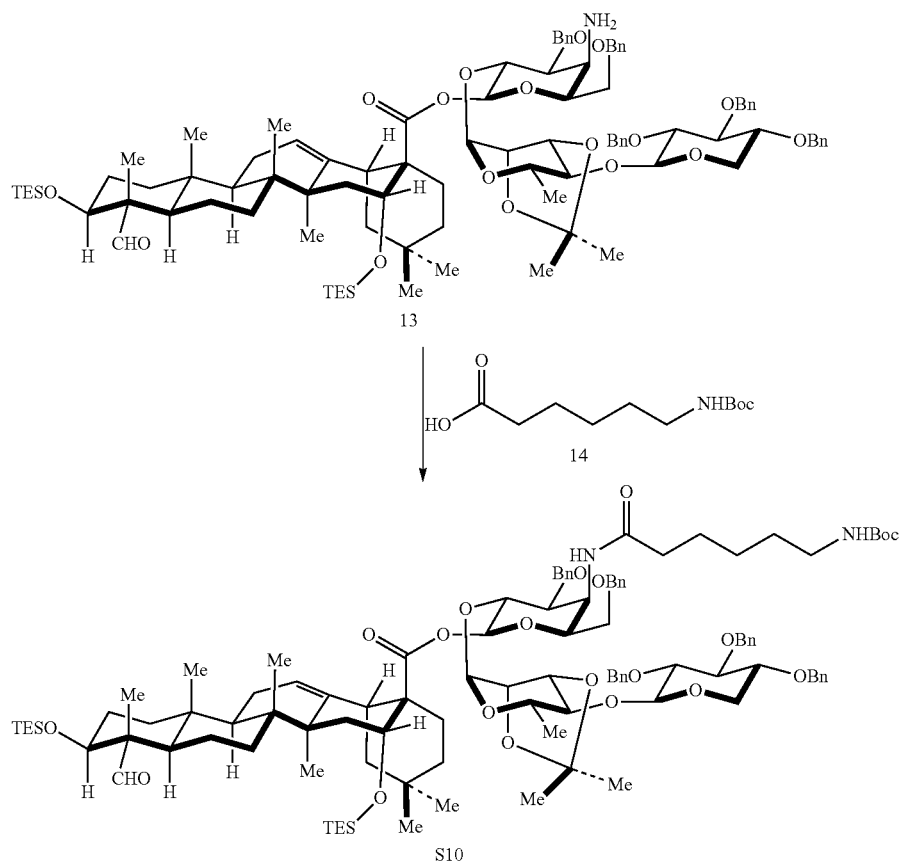

Fully protected aminoacyl quillaic acid saponin S10. (AFT-I-169) To a clear, colorless solution of 6-((t-butoxycarbonyl)-amino)hexanoic acid (14) (45 mg, 0.20 mmol, 11.5 equiv) in tetrahydrofuran (2.5 mL) at 0° C. was added (Na$_2$SO$_4$), filtered, and evaporated to dryness. Purification by silica gel chromatography (2:1 hexanes/EtOAc with 0.2% triethylamine) afforded S10 (28 mg, 88% yield) as a white glassy solid.

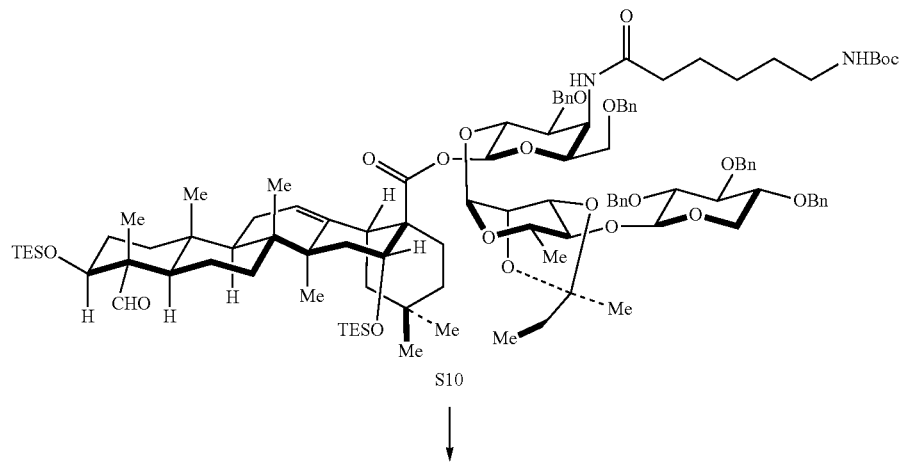

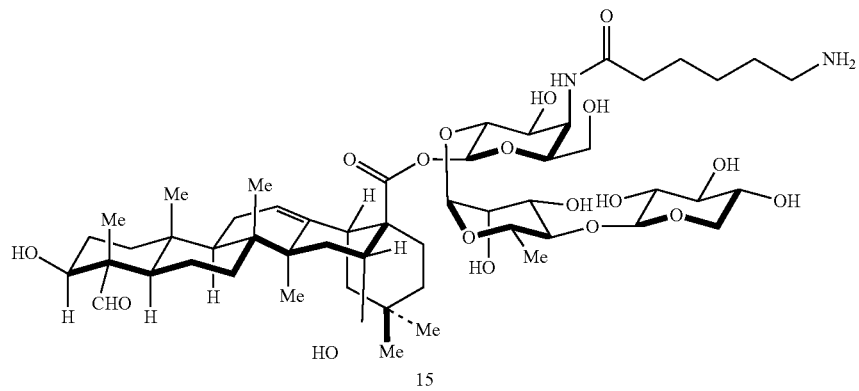

Aminoacyl quillaic acid saponin 15. (AFT-I-204) In a 50 mL round-bottom flask, S10 (68 mg, 36.6 μmol, 1.0 equiv) was dissolved in tetrahydrofuran/ethanol (20 mL, 1:1) and 10% (dry basis) palladium on carbon, wet, Degussa type E101 NE/W (390 mg, 0.18 mmol, 5.0 equiv) was added. The reaction was stirred under hydrogen pressure (50 psi) at 21° C. for 24 h, and the suspension was filtered through a 0.45 μm nylon syringe filter, washed with methanol (3×30 mL) and concentrated. Successful debenzylation is assessed by the disappearance of aromatic resonances by $^1$H NMR in CD$_3$OD. The crude mixture was then dissolved in a solution of trifluoroacetic acid (8 mL, TFA/H$_2$O 3:1) and stirred for 2 h in an ice bath. The reaction was evaporated to dryness to afford a white solid that was dissolved in 20% acetonitrile/water (20 mL) and purified via RP-HPLC on an XBridge Prep BEH300 C18 column (5 μm, 10×250 mm) using a linear gradient of 30-70% acetonitrile/water (0.05% TFA), over 15 min, at a flow rate of 5 mL/min. The aminoacyl quillaic acid saponin 15 eluted as a single peak and was obtained as a white powder (28 mg, 74% yield) after lyophilization.

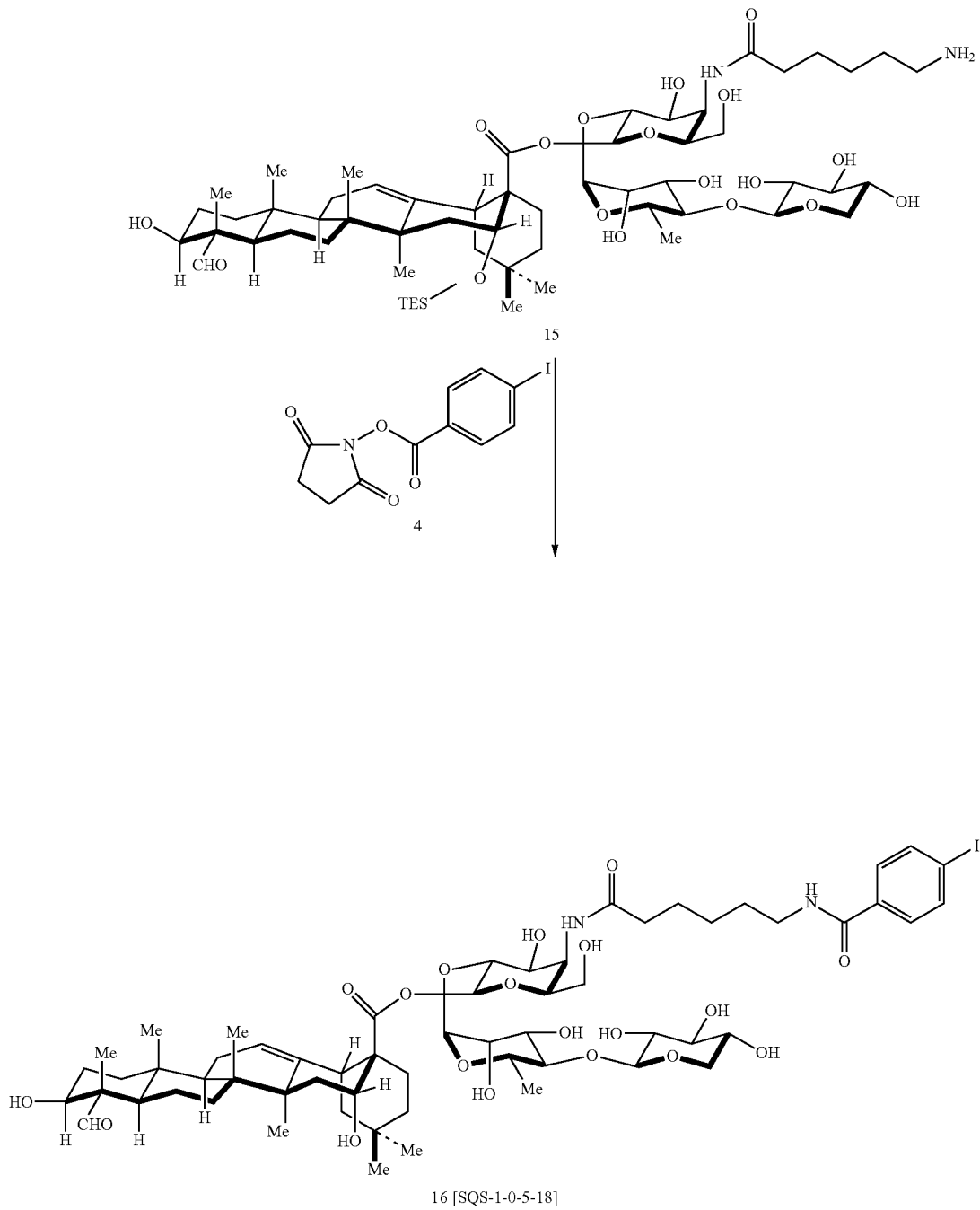

SQS-1-0-5-18 (16). (AFT-I-300) To a solution of 15 (2.1 mg, 2.0 μmol, 1.0 equiv) in N,N'-dimethylformamide (0.4 mL) was added triethylamine (11 IL, 0.08 mmol, 40 equiv) followed by dropwise addition of 4 (4.0 mg, 10 μmol, 5.8 equiv) in N,N'-dimethylformamide (0.2 mL). After stirring for 2 h, the contents were diluted with 30% acetonitrile/water (2.3 mL) and purified by RP-HPLC on an XBridge Prep BEH300 C18 column (5 μm, 10×250 mm) using a linear gradient of 30-70% acetonitrile/water (0.05% TFA), over 15 min, at a flow rate of 5 mL/min. SQS-1-0-5-18 (16) (1.7 mg, 67% yield) was obtained as a white powder after lyophilization.

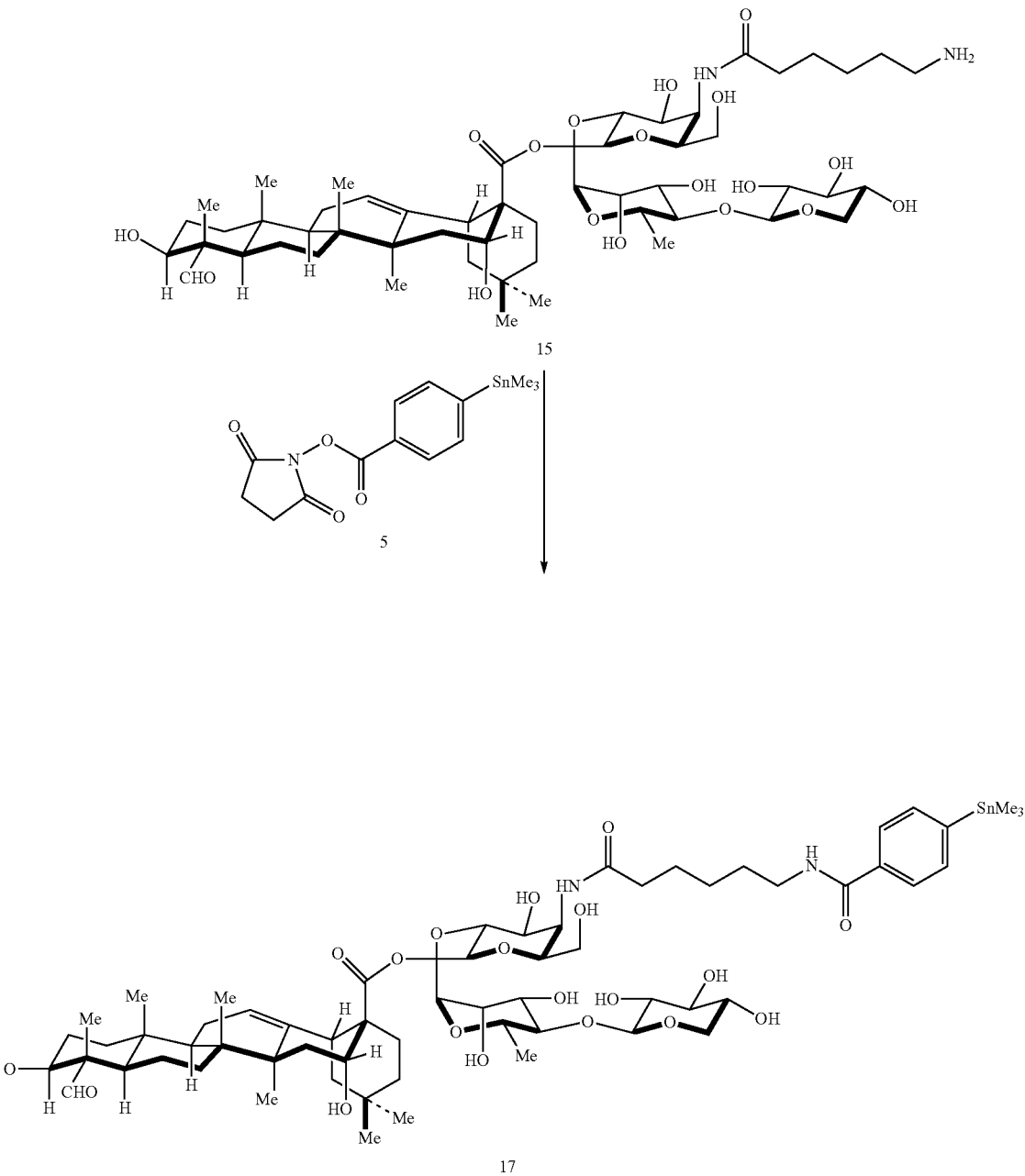

Aryl tin precursor to [1]1-SQS-1-0-5-18 (17). (EC-V-227) To 15 (0.65 mg, 0.63 μmol, 1.0 equiv) dissolved in N,N'-dimethylformamide (0.2 mL) was added triethylamine (10 μL, 72 mol, 114 equiv) and 5 (1.0 mg, 2.6 μmol, 4.1 equiv). After stirring for 1.5 h the reaction was diluted with water (4 mL) and purified via RP-HPLC on an XBridge Prep BEH300 C18 column (5 μm, 10×250 mm) with a 35-95% acetonitrile/water linear gradient, over 30 min, at a flow rate of 5 mL/min. Saponin 17 (0.6 mg, 75% yield) eluted as a single peak and was obtained as a white powder after lyophilization.

Synthesis of Variants with Modifications in the Triterpene Domain (18-22)

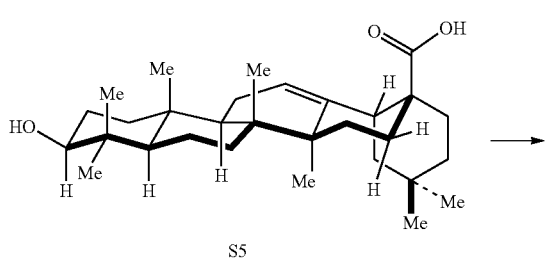

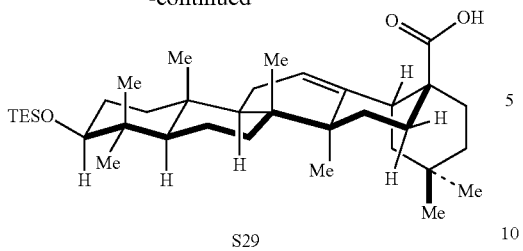

Silyl ether of oleanolic acid (S29). (AFT-I-137) To a solution of oleanolic acid S5 (250 mg, 0.55 mmol, 1.0 equiv) in $CH_2Cl_2$ (10 mL) at 0° C., 2,6-lutidine (0.38 mL, 3.28 mmol, 6.0 equiv), and triethylsilyl trifluoromethanesulfonate (0.37 mL, 1.64 mmol, 3.0 equiv) were added and the mixture was stirred for 1 h. The contents were quenched with 0.5 N HCl (10 mL), and the aqueous phase was extracted with $CH_2Cl_2$ (2×15 mL). The combined organics were dried over $Na_2SO_4$, filtered, concentrated and finally purified by silica gel chromatography (hexanes to 4:1 hexanes/EtOAc) to afford S29 (250 mg, 80% yield).

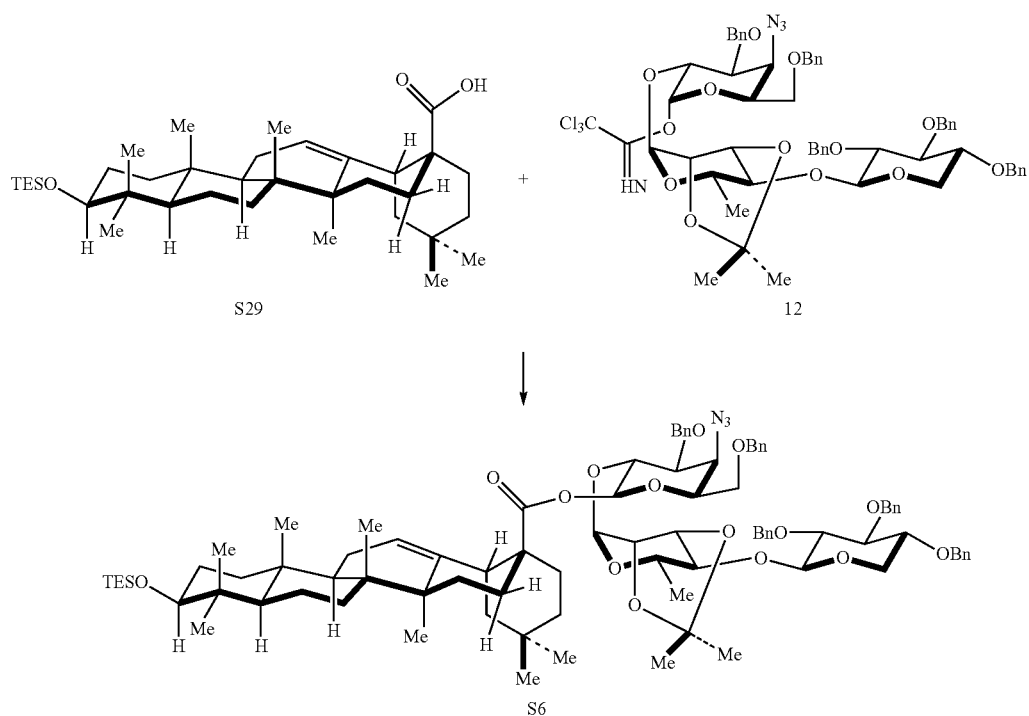

Protected oleanolic acid saponin azide S6. (EC-V-215) To a solution of S29 (50 mg, 87 μmol, 1.0 equiv) and imidate 12 (97 mg, 87 μmol, 1.0 equiv) in $CH_2Cl_2$ (8.0 mL) was added 120 mg powdered 4 Å molecular sieves and the mixture was stirred at 21° C. for 1 h. The reaction schlenk was then transferred to a −78° C. bath and boron trifluoride diethyletherate (8.8 μL, 70 μmol, 0.8 equiv) was injected. The reaction was stirred at −50° C. for 20 min, at 21° C. for 1 min, cooled back to −50° C., stirred for 20 min and finally again at 21° C. for 1 min. The mixture was then quenched with triethylamine (0.1 mL) at −50° C. and passed through a plug of silica gel. The resulting filtrate was concentrated, and purified by silica gel chromatography (hexanes to 5:1 hexanes/EtOAc) to afford S6 (89 mg, 68% yield) as a glassy solid.

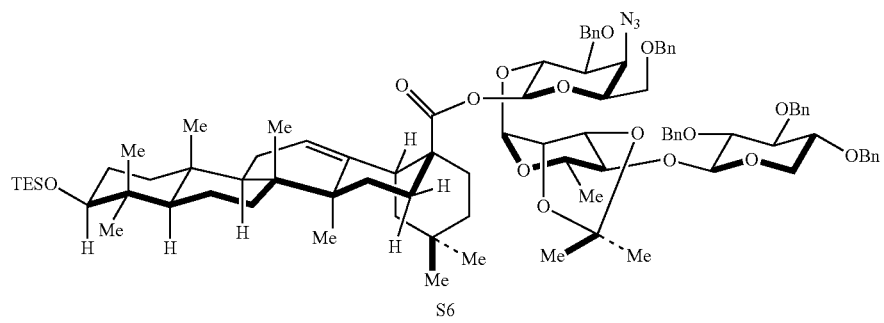

S6

↓

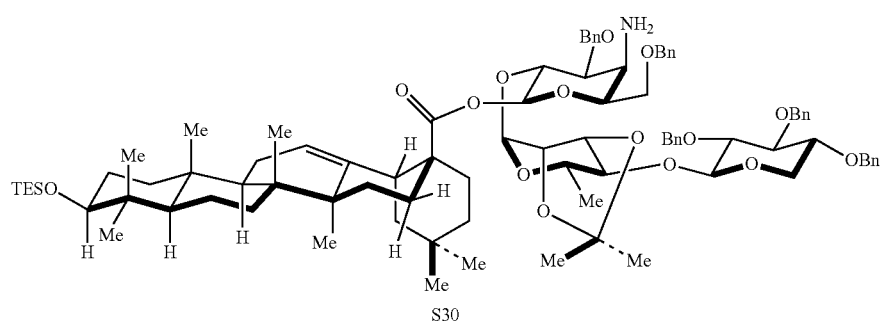

S30

Protected oleanolic acid saponin amine S30. (EC-V-216) To S6 (44 mg, 29 μmol, 1.0 equiv) dissolved in triethylamine (12 mL) was added a freshly prepared solution of phenyl selenol (0.44 mmol, 15 equiv) via cannula transfer. Upon addition of phenyl selenol a white precipitate was formed and the mixture became bright yellow. After stirring at 38° C. for 8 h, the solution was concentrated to give a yellow-white solid, which was purified by silica gel chromatography (5:1 hexanes/EtOAc to 2% triethylamine in EtOAc) to afford S30 (41 mg, 95% yield) as a white solid.

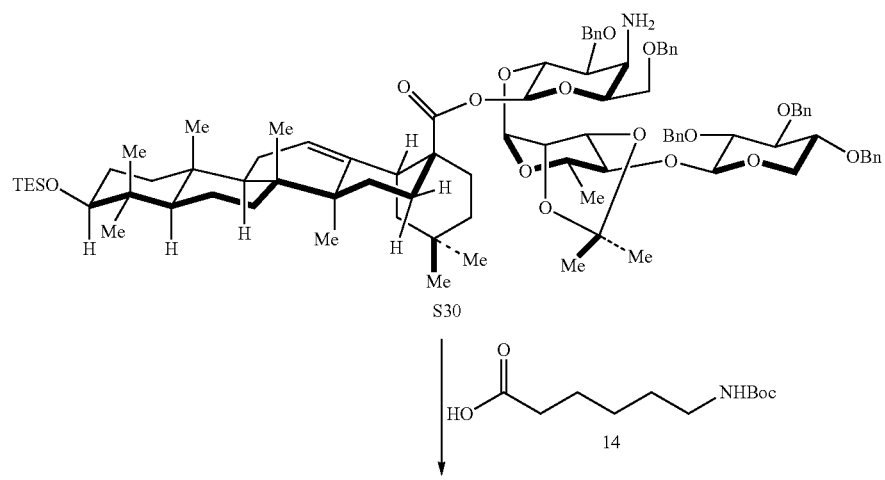

S30

↓

-continued

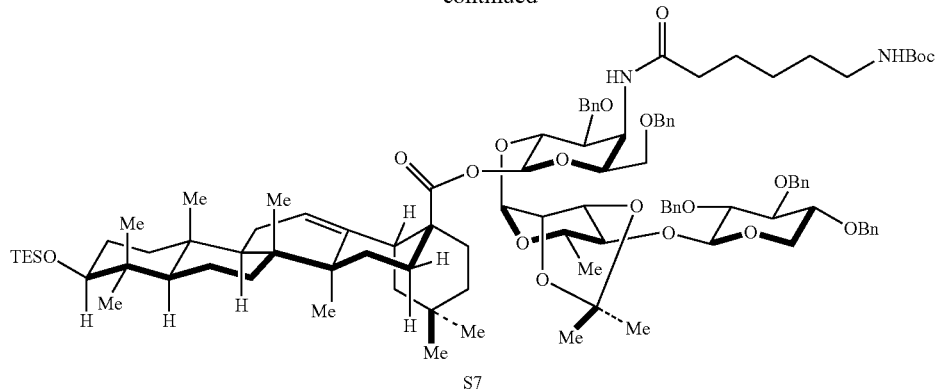

Fully protected aminoacyl oleanolic acid saponin S7. (EC-V-217) To a solution of 14 (63 mg, 0.27 mmol, 10 equiv) in tetrahydrofuran (2.6 mL) was added triethylamine (365 µL, 2.6 mmol, 96 equiv) at 0° C. To the clear, colorless solution was injected ethyl chloroformate (23 µL, 0.25 mmol, 9.0 equiv), which turned the solution turbid white. The acid activation was allowed to proceed at 0° C. for 2.5 h before the entire solution was cannula transferred into a schlenck containing amine S30 (41 mg, 27 µmol, 1.0 equiv). The reaction mixture was stirred at 0° C. for 1.5 h and then quenched with water (90 µL), at which point the solution turned from turbid, white to clear. The contents were then evaporated to dryness and purified by silica gel chromatography (5:1 hexanes/EtOAc) to afford S7 (40 mg, 81% yield) as a white glassy solid.

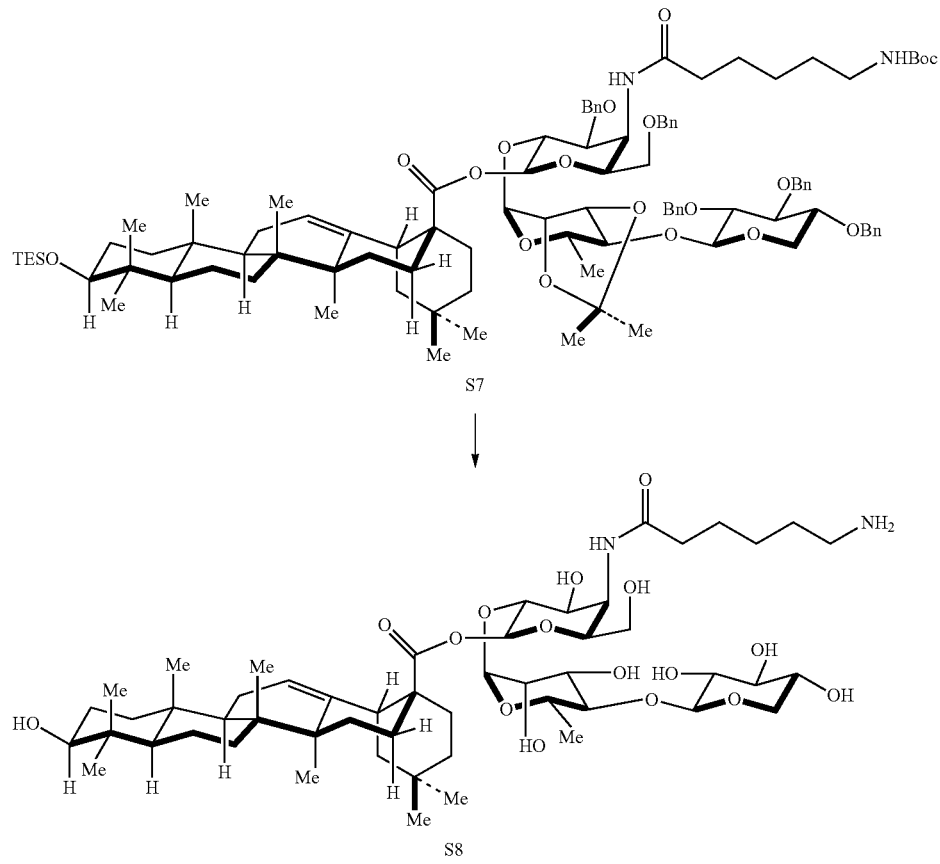

Aminoacyl oleanolic acid saponin S8. (EC-V-218) In a 25 mL round-bottom flask containing S7 (10 mg, 5.8 µmol, 1.0 equiv) was added tetrahydrofuran/ethanol (2 mL, 1:1) followed by 10% (dry basis) palladium on carbon, wet, Degussa type E101 NE/W (14.0 mg, 6.5 µmol, 1.1 equiv). The reaction was stirred under hydrogen pressure (50 psi) at 21° C. for 24 h and then filtered through a 0.45 mm nylon syringe filter, washed with methanol (20 mL), CH2Cl2 (10 mL), and methanol again (5 mL) to thoroughly wash the palladium. The clear filtrate was evaporated to dryness.

Successful debenzylation was assessed by the disappearance of aromatic resonances by 1H NMR in CD3OD. The mixture was then dissolved in a solution of trifluoroacetic acid/water (2 mL, 4:1) and stirred for 2 h in an ice bath. After this time, the reaction was evaporated to dryness to give a white solid that was purified by RP-HPLC using a 30-80% acetonitrile/water (0.1% TFA) linear gradient, over 20 min, at a flow rate of 5 mL/min. The desired product S8 (2.6 mg, 44% yield) was obtained as a white powder after lyophilization.

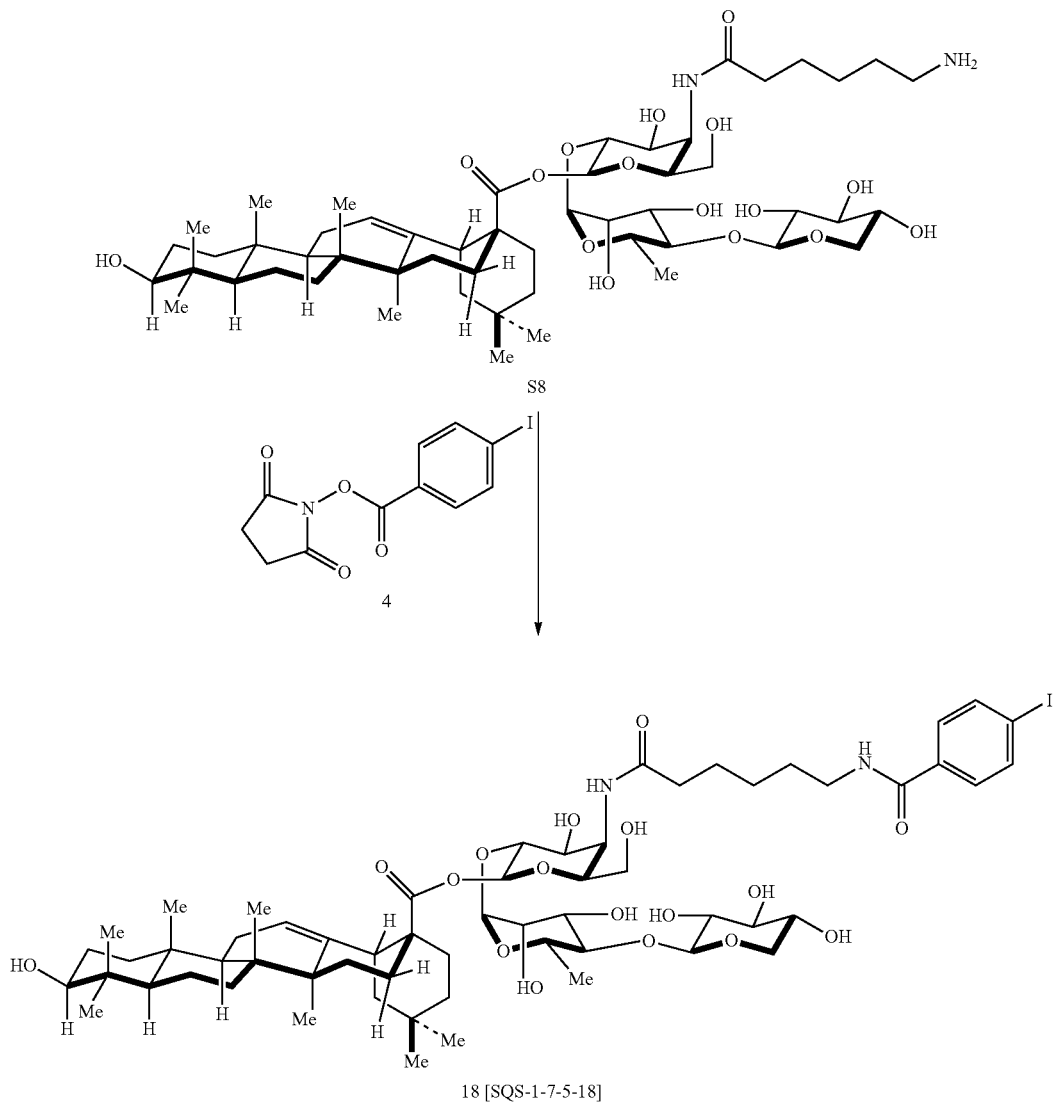

SQS-1-7-5-18 (18). (EC-V-221) Amine S8 (1.3 mg, 1.3 μmol, 1.0 equiv) was dissolved in N,N'-dimethylformamide (0.2 mL) and triethylamine (3.6 μL, 25.6 μmol, 20 equiv) was injected. To this solution, 4 (2.5 mg, 7.3 μmol, 5.7 equiv) was added and the reaction mixture was stirred at 21° C. for 2 h. After this time, the contents were diluted with 3 mL water (0.05% TFA) and directly purified by HPLC using a 30-80% acetonitrile/water (0.05% TFA) linear gradient, over 20 min, at a flow rate of 5 mL/min to afford SQS-1-7-5-18 (18) (1.0 mg, 63% yield) as a white powder after lyophilization.

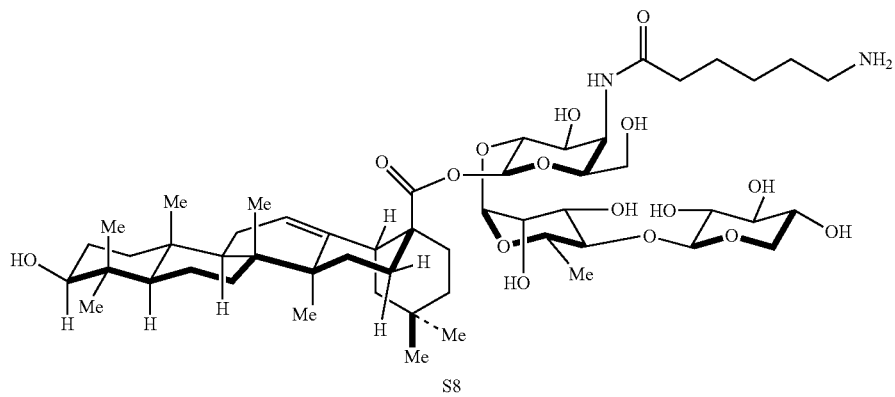

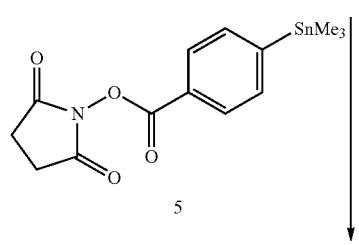

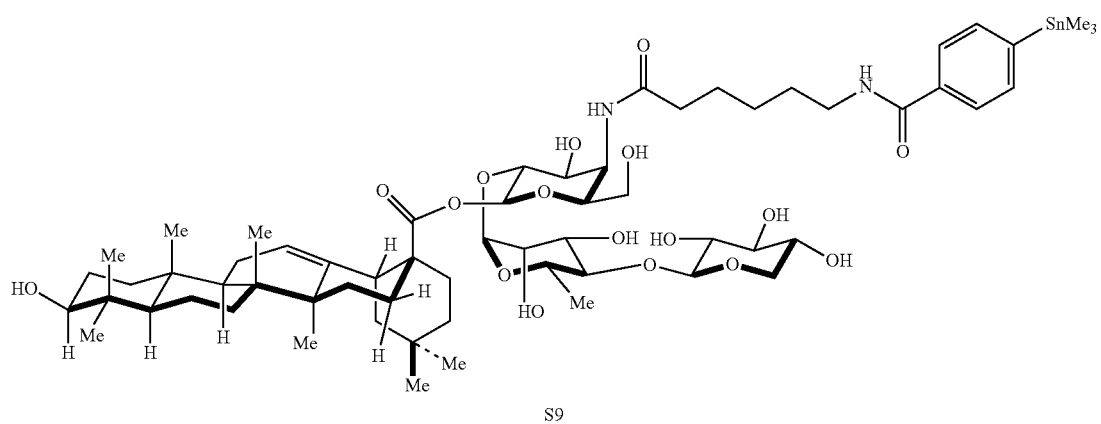

Aryl tin precursor to SQS-1-7-5-18 (S9). (EC-V-222) To a solution of amine S8 (1.3 mg, 1.3 μmol, 1.0 equiv) in N,N'-dimethylformamide (0.2 mL) triethylamine (3.6 μL, 25.6 μmol, 20 equiv) was added followed by 5 (2.6 mg, 6.8 μmol, 5.2 equiv). After stirring at 21° C. for 1.5 h, the reaction was diluted with 3 mL water and directly purified by RP-HPLC using a linear gradient of 30-90% acetonitrile/water, over 30 min, at a flow rate of 5 mL/min to afford S9 (1.0 mg, 62% yield) as a white powder after lyophilization.

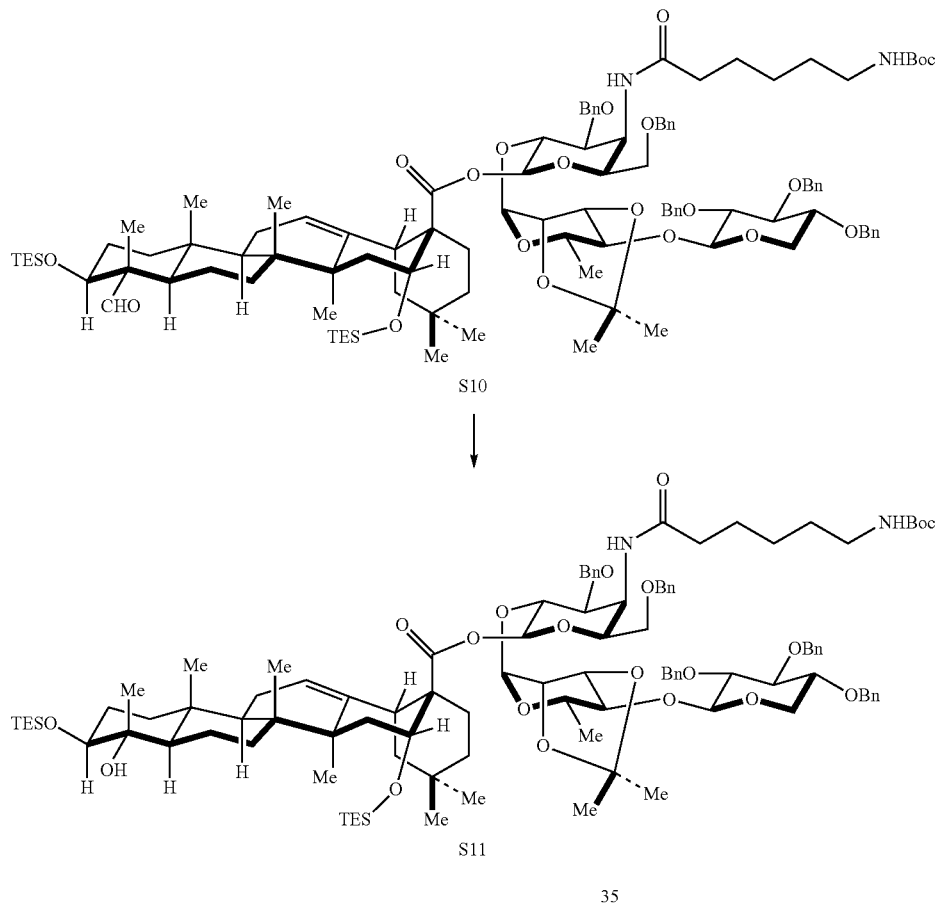
S10
S11
Fully protected aminoacyl caullophylogenin saponin S11. (AFT-I-243). To a solution of S10 (10 mg, 5.4 μmol) in methanol (1.0 mL) $NaBH_4$ was added, and the reaction was stirred at 21° C. for 3 h. The mixture was then diluted with acetone (2 mL), concentrated, and purified by silica gel chromatography (85:15 benzene/EtOAc) to afford S11 (10 mg, >99% yield).
S11

-continued
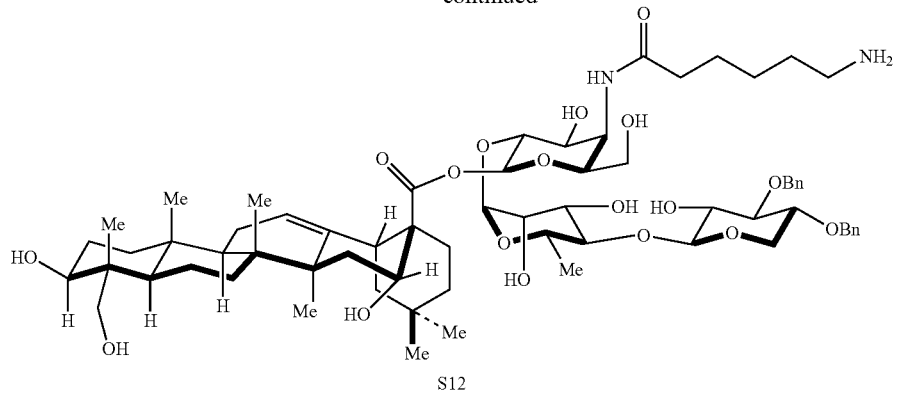
S12

Aminoacyl caullophylogenin saponin S12. (AFT-I-244) In a 25 mL round-bottom flask, S11 (15 mg, 8.1 μmol, 1.0 equiv) was dissolved m 4.0 mL tetrahydrofuran/ethanol (1:1) and 10% (dry basis) palladium on carbon, wet, Degussa type E101 NE/W (85 mg, 0.04 mmol, 5.0 equiv) was added. The reaction was stirred under hydrogen atmosphere (balloon) at 21° C. for 12 h, and the suspension was filtered through a 0.45 μm nylon syringe filter, thoroughly washed with methanol (4×20 mL) and concentrated. Successful debenzylation is assessed by the disappearance of aromatic resonances by $^{1}H$ NMR in $CD_3OD$. The crude mixture was then dissolved in a pre-cooled (0° C.) solution of trifluoroacetic acid (3.2 mL, TFA/$H_2O$ 3:1) and stirred at 0° C. for 1.25 h. The reaction was evaporated to dryness, and the crude product was dissolved in 20% acetonitrile/water (8 mL) and purified via RP-HPLC on an XBridge Prep BEH300 C18 column (5 μm, 10×250 mm) using a linear gradient of 20-70% acetonitrile/water (0.05% TFA), over 20 min, at a flow rate of 5 mL/min. The desired product S12 was obtained as a white powder (5.8 mg, 70% yield) after lyophilization.

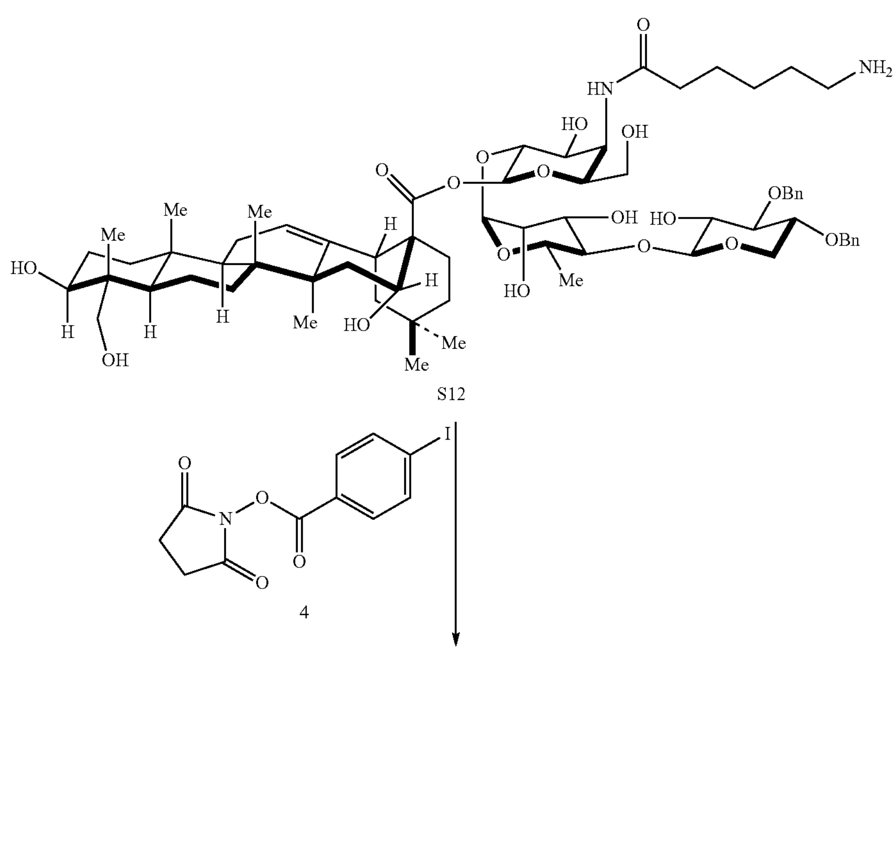

S12

4

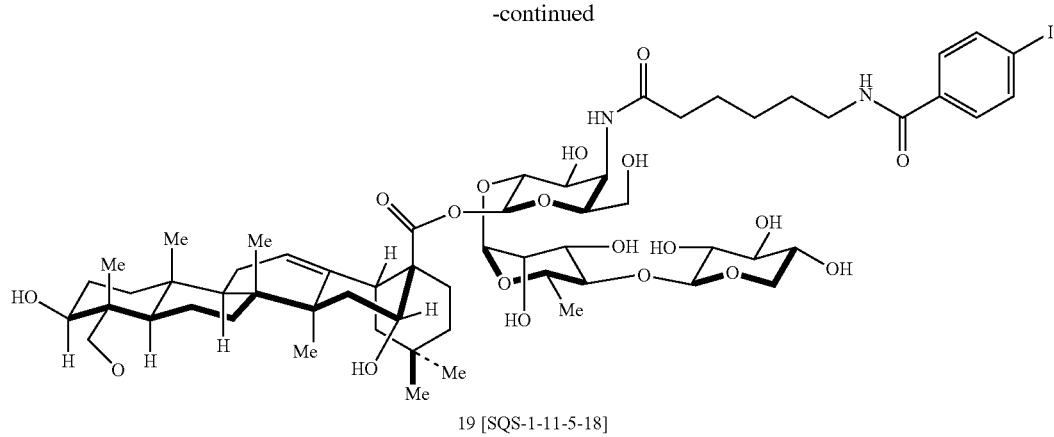

19 [SQS-1-11-5-18]

SQS-1-11-5-18 (19). (AFT-I-245) To a solution of S12 (7.0 mg, 6.7 μmol, 1.0 equiv) in N,N'-dimethylformamide (1.3 mL) was injected triethylamine (20 μL, 0.13 mmol, 20 equiv) followed by dropwise addition of 4 (11.6 mg, 33.6 μmol, 5.0 equiv) in N,N'-dimethylformamide (0.7 mL). After stirring for 3 h, the contents were diluted with 25% acetonitrile/water (10 mL) and purified by RP-HPLC on an XBridge Prep BEH300 C18 column (5 μm, 10×250 mm) using a linear gradient of 30-70% acetonitrile/water (0.05% TFA), over 15 min, at a flow rate of 5 mL/min. SQS-1-11-5-18 (19) (5.5 mg, 65% yield) was obtained as a white powder after lyophilization.

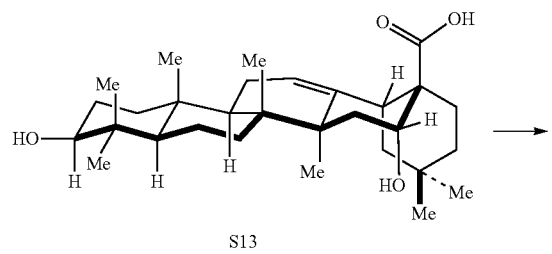

S13

Bis(silyl ether) of echinocystic acid (S14). (AFT-I-206) Echinocystic acid S13 (18 mg, 38 μmol, 1.0 equiv) was suspended in $CH_2Cl_2$ (10 mL) and cooled in an ice bath. 2,6-lutidine (71 μL, 0.61 mmol, 16 equiv) was then added followed by triethylsilyl trifluoromethanesulfonate (69 μL, 0.31 mmol, 8.0 equiv) and the reaction mixture was stirred at 0° C. for 1 h. After this time, the contents were washed with saturated $NaHCO_3$ (5 mL) and the aqueous phase was extracted with $CH_2Cl_2$ (2×10 mL). The combined organics were dried over $Na_2SO_4$, filtered, and concentrated. The crude product was purified by silica gel chromatography (hexanes to 9:1 hexanes/EtOAc) to afford S14 (25 mg, 94% yield).

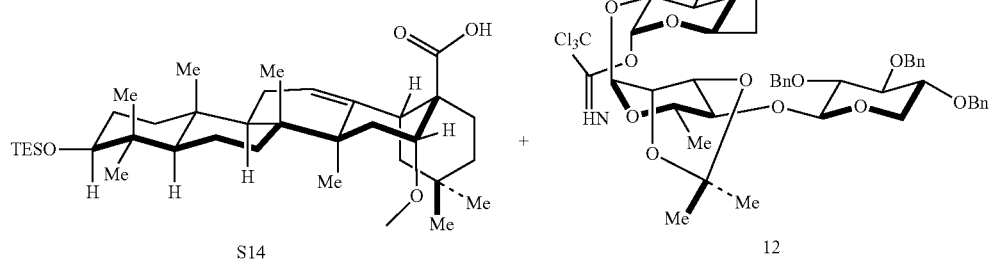

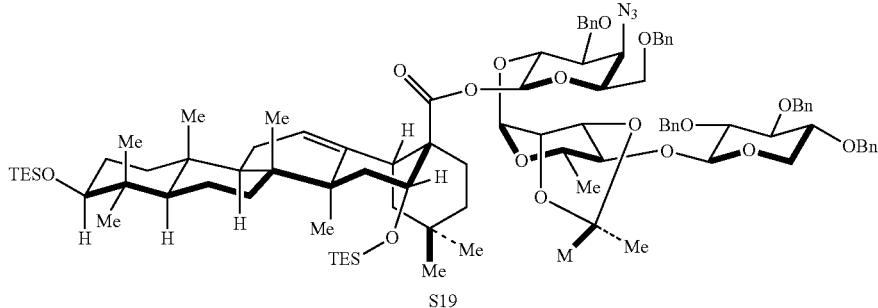
S19

Protected echinocystic acid saponin azide S19. (AFT-I-212) A solution of S14 (25 mg, 36 μmol, 1.0 equiv) and imidate 12 (50 mg, 45 μmol, 1.25 equiv) in $CH_2Cl_2$ (5 mL) with 40 mg powdered 4 Å molecular sieves was cooled to −45° C. and boron trifluoride diethyletherate (0.9 μL, 7 μmol, 0.2 equiv) was added. The mixture was stirred at this temperature for 0.5 h min, quenched with 0.2 mL of triethylamine and concentrated. Purification of the residue by silica gel chromatography (0.2% triethylamine in benzene to 97:3 benzene/EtOAc) gave S19 (48 mg, 80% yield) as a white solid.

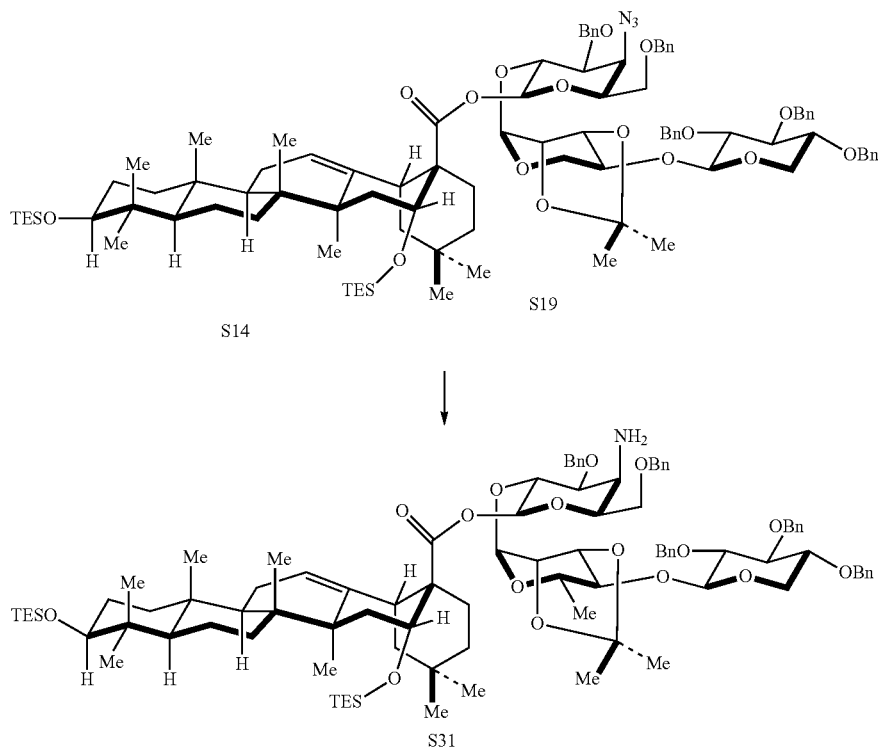

Protected echinocystic acid saponin amine S31. (AFT-I-214) To S19 (52 mg, 31 μmol, 1.0 equiv) dissolved in triethylamine (25 mL) was added a freshly prepared solution of phenyl selenol (0.94 mmol, 30 equiv) via cannula. The reaction was stirred at 38° C. for 8 h, and the solution was then concentrated to afford a yellow-white solid. The crude mixture was purified by silica gel chromatography (9:1 to 4:1 toluene/EtOAc) to afford the amine S31 (42 mg, 83% yield) as a glassy solid.

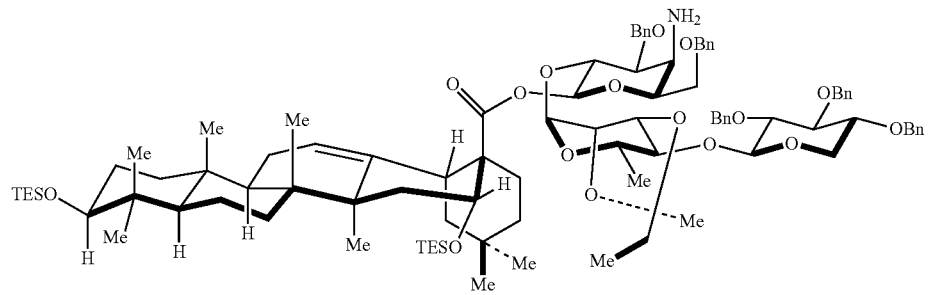

S31

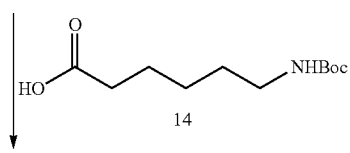

14

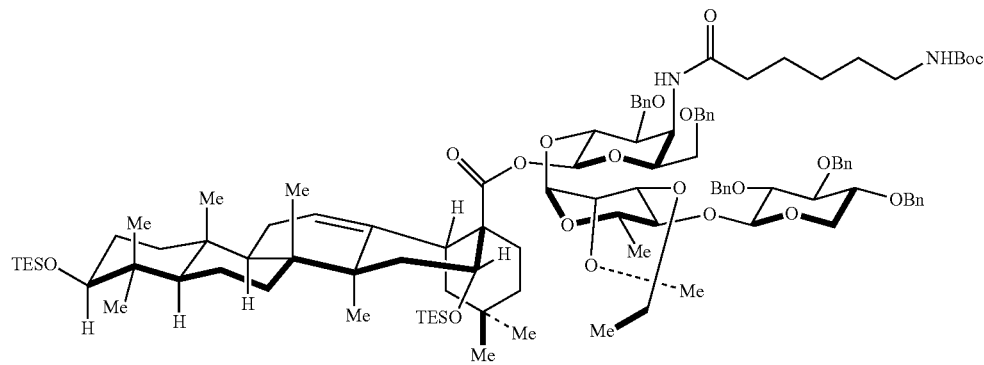

S22

Fully protected aminoacyl echinocystic acid saponin S22. (AFT-I-215) To a clear, colorless solution of 6-((t-butoxycarbonyl)-amino)hexanoic acid (14) (44 mg, 0.19 mmol, 11.5 equiv) in tetrahydrofuran (2 mL) at 0° C. was added triethylamine (208 µL, 1.49 mmol, 90 equiv) followed by ethyl chloroformate (16.0 µL, 0.17 mmol, 10.0 equiv). The turbid, white solution was stirred at 0° C. for 2.5 h and then added via cannula to amine S31 (27 mg, 16.6 µmol, 1.0 equiv) at 0° C. The reaction mixture was stirred at this temperature for 1.5 h and then quenched with water (0.2 mL) and concentrated. Purification by silica gel chromatography (9:1 to 5:1 benzene/EtOAc with 0.2% triethylamine) afforded S22 (27 mg, 88% yield) as a white glassy solid.

Aminoacyl echinocystic acid saponin S25. (AFT-I-216) In a 25 mL round-bottom flask containing S22 (24 mg, 13 µmol, 1.0 equiv) was added tetrahydrofuran/ethanol (6 mL, 1:1) and 10% (dry basis) palladium on carbon, wet, Degussa type E101 NE/W (138 mg, 65 µmol, 5.0 equiv). The reaction was stirred under hydrogen atmosphere (balloon) at 21° C. for 12 h, and then filtered through a 0.45 µm nylon syringe filter, washed with methanol (3×10 mL), and concentrated. Successful debenzylation is assessed by the disappearance of aromatic resonances by $^1$H NMR in $CD_3OD$. The crude mixture was then dissolved in a pre-cooled (0° C.) solution of trifluoroacetic acid (4 mL, $TFA/H_2O$ 3:1) and stirred for 1.25 h in an ice bath. The reaction was evaporated to dryness to afford a white solid that was dissolved in 25% acetonitrile/water (12 mL) and purified via RP-HPLC on an XBridge Prep BEH300 C18 column (5 µm, 10×250 mm) using a linear gradient of 30-70% acetonitrile/water (0.05% TFA), over 15 min, at a flow rate of 5 mL/min. The aminoacyl echinocystic acid saponin S25 eluted as a single peak and was obtained as a white powder (7.0 mg, 53% yield) after lyophilization.

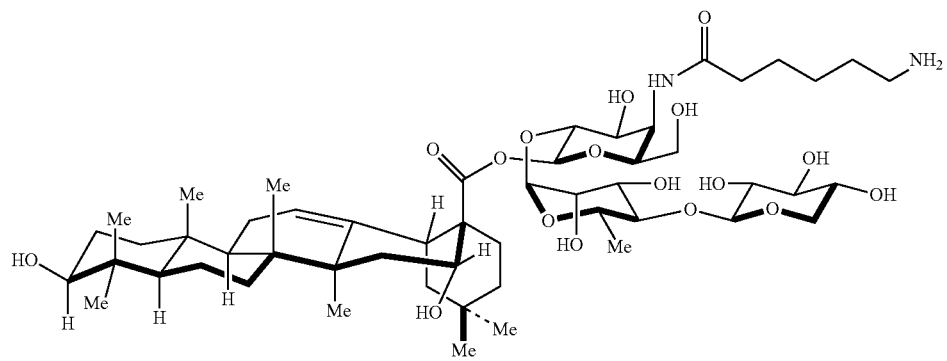

S25

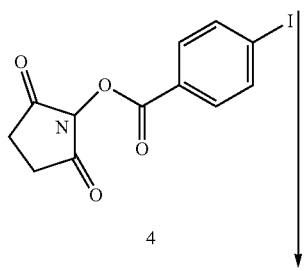

4

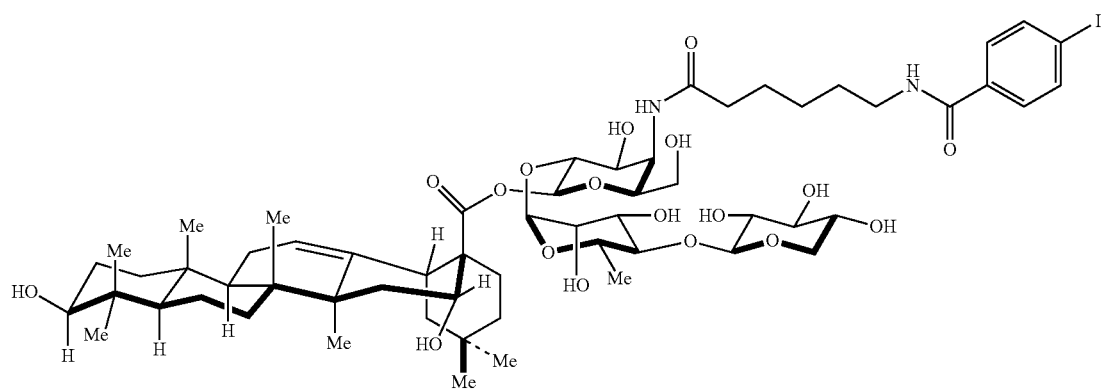

20 [SQS-1-8-5-18]

SQS-1-8-5-18 (20). (AF-I-223) S25 (7.0 mg, 6.8 μmol, 1.0 equiv) was dissolved in N,N'-dimethylformamide (2 mL) in a 25 ml, round-bottom flask and triethylamiine (20 μL, 0.14 mmol, 20 equiv) was injected. A solution of 4 (11.8 mg, 34 μmol, 5.0 equiv) in N,N'-dimethylformamide (1.5 mL) was added dropwise via syringe and the reaction was stirred at 21° C. in the dark. After 3 h, the contents were diluted with 25% acetonitrile/water (9 mL) and purified via RP-HPLC on an XBridge Prep BEH300 C18 column (5 μm, 10×250 mm) using a linear gradient of 30-70% acetonitrile/water (0.05% TFA), over 15 min, at a flow rate of 5 mL/min. SQS-1-8-5-18 (20) (6.8 mg, 80% yield) eluted as a single peak and was obtained as a white powder after lyophilization.

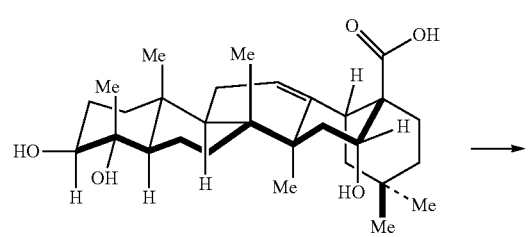

S15

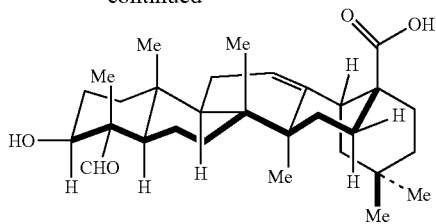

S16

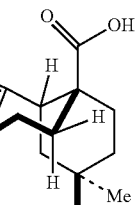

S16

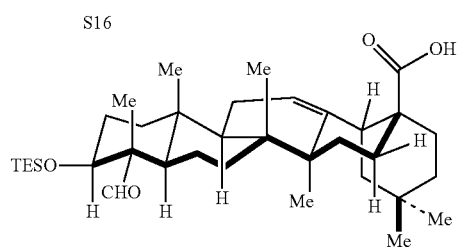

S17

Gypsogenin (S16). (AFT-I-218) In a 25 mL round bottom flask, hederagenin S15 (45 mg, 95 μmol, 1.0 equiv) was suspended in CH₂Cl2 (3.5 mL), and an aqueous solution (3.5 mL) of 0.5 M NaHCO₃ (147 mg), 0.05 M K₂CO₃ (24.2 mg), and tetrabutylammonium chloride hydrate (28 mg, 95 μmol, 1.0 equiv) was then added. To the vigorously stirred mixture, TEMPO (14.8 mg, 95 μmol, 1.0 equiv) was added followed by N-chlorosuccinimide (38.0 mg, 0.29 mmol, 3.0 equiv) and the reaction was stirred for 2 h in the dark. The contents were partitioned in a separation funnel and extracted with CH₂Cl₂ (3×10 mL). The combined organic extracts were dried over Na₂SO₄, filtered, and concentrated to give a crude product that was purified by silica gel chromatography (hexanes/EtOAc, 7:3) to afford the desired gypsogenin triterpene S16 (32 mg, 72% yield).

Silyl ether of gypsogenin (S17). (AFT-I-219) A suspension of gypsogenin S16 (32 mg, 68 μmol, 1.0 equiv) in CH₂C2 (10 mL) was cooled in an ice bath and 2,6-lutidine (63 μL, 0.54 mmol, 8.0 equiv) and triethylsilyl trifluoromethanesulfonate (62 μL, 0.27 mmol, 4.0 equiv) were injected. After stirring for 1 h, the contents were washed with saturated NaHCO₃ (7 mL) and the aqueous phase was extracted with CH₂Cl₂ (3×10 mL). The combined organics were dried (Na₂SO₄), filtered, and concentrated. The crude product was purified several times by silica gel chromatography (hexanes to 4:1 hexanes/EtOAc) to afford S17 (26 mg, 65% yield).

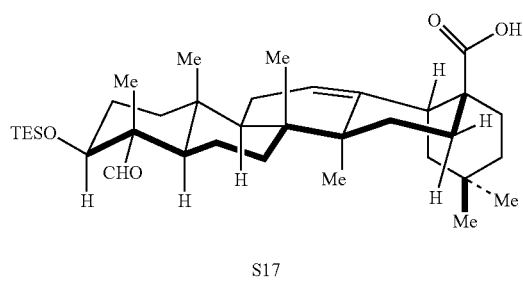

S17

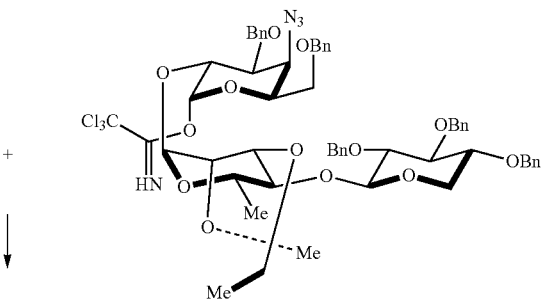

12

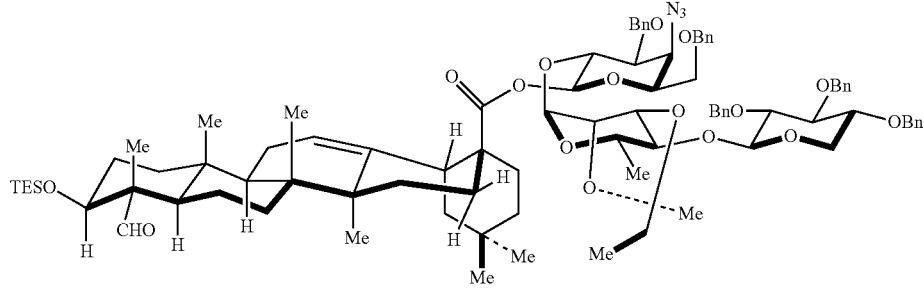

S20

Protected gypsogenin saponin azide S20. (AF-I-224) A solution of S17 (26 mg, 44 µmol, 1.0 equiv) and imidate 12 (55 mg, 49 µmol, 1.1 equiv) in CH$_2$Cl$_2$ (6 mL) with 40 mg powdered 4 Å molecular sieves was stirred at 21° C. for 30 min and then cooled to −45° C. before injecting boron trifluoride diethyletherate (1.1 µL, 9 µmol, 0.2 equiv). The reaction was stirred at this temperature for 0.5 h, quenched with triethylamine (0.2 mL) and concentrated. Purification by silica gel chromatography (benzene to 97:3 benzene/EtOAc) gave desired product plus some impure mixture that was further chromatographed to afford S20 (48 mg, 70% yield) as a glassy solid.

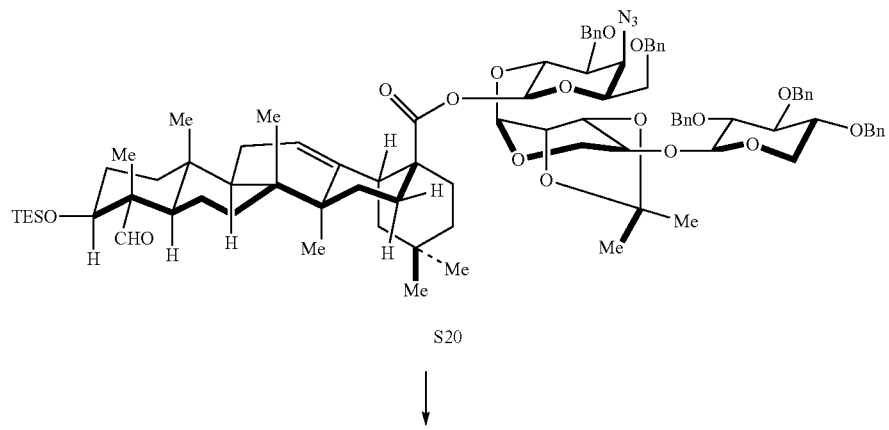

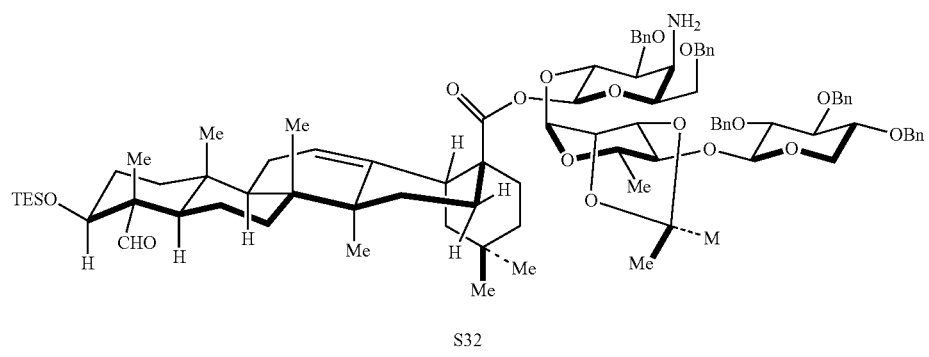

Protected gypsogenin saponin amine S32. (AF-I-225) To a solution of S20 (50 mg, 32 µmol, 1.0 equiv) in triethylamine (27 mL) was added a freshly prepared solution of phenyl selenol (1.07 mmol, 32 equiv) via cannula. After stirring at 38° C. for 8 h, the solution was concentrated to give a yellow-white solid, which was purified by silica gel chromatography (9:1 to 8:2 toluene/EtOAc) to afford S32 (35 mg, 72% yield) as a white solid.

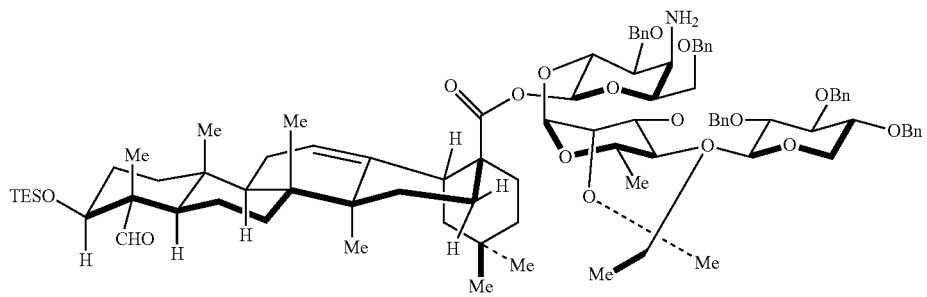

S32

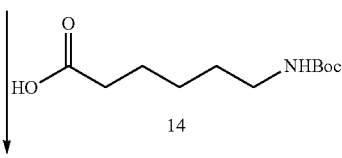

14

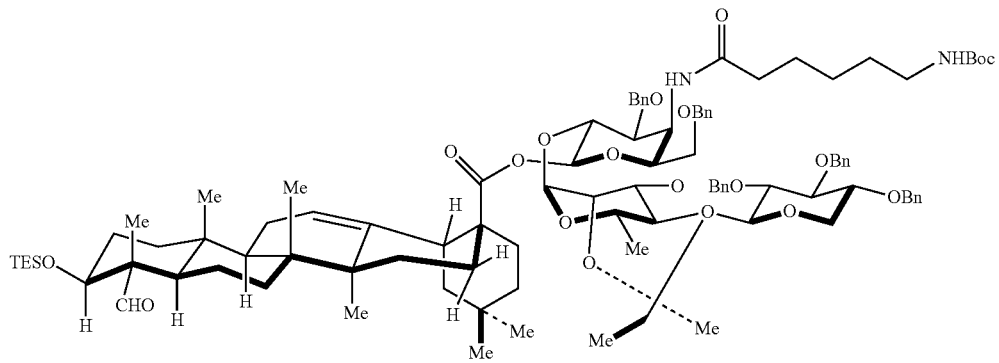

S23

Fully protected aminoacyl gypsogenin saponin S23. (AFT-I-226) To a solution of 14 (61 mg, 0.27 mmol, 11.5 equiv) in tetrahydrofuran (3 mL) at 0° C. was added triethylamine (290 μL, 2.1 mmol, 90 equiv) followed by ethyl chloroformate (22 μL, 0.23 mmol, 10 equiv), which turned the clear solution turbid white. The acid activation was allowed to proceed for 2.5 h at 0° C. and the entire solution was cannula transferred into a schlenck containing amine S32 (35 mg, 23 μmol. 1.0 equiv). The reaction mixture was stirred at 0° C. for 1.5 h and then quenched with water (90 μL), at which point the solution turned from turbid, white to clear. The contents were then evaporated to dryness and purified by silica gel chromatography (9:1 to 5:1 benzene/ EtOAc with 0.2% triethylamine) to afford S23 (34 mg, 86% yield) as a white glassy solid.

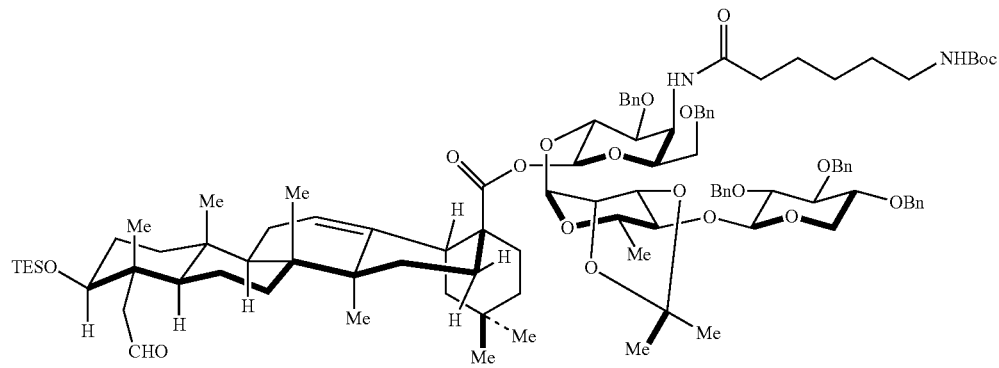

S23

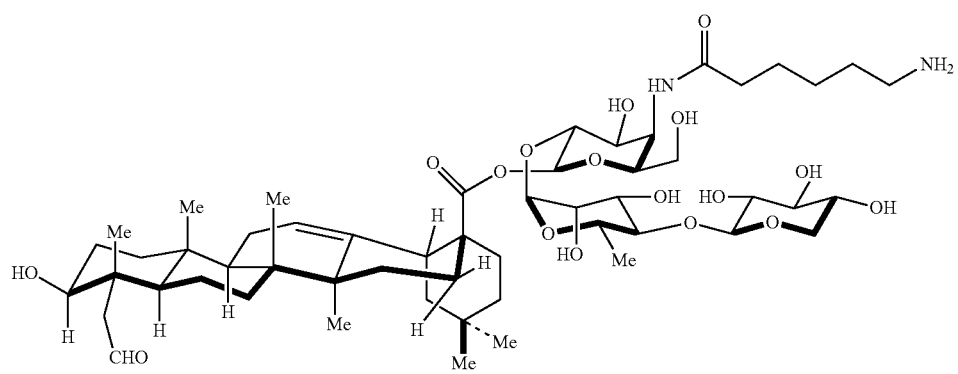

S26

Aminoacyl gypsogenin saponin S26. (AF-1-227) In a 25 mL round-bottom flask, S23 (27 mg, 15.5 μmol, 1.0 equiv) was dissolved in 6 mL tetrahydrofuran/ethanol (1:1) and 10% (dry basis) palladium on carbon, wet, Degussa type E101 NE/W (166 mg, 78 μmol, 5 equiv) was added. The reaction was stirred under hydrogen atmosphere (balloon) at 21° C. for 12 h. After this time, the mixture was filtered through a 0.45 mm nylon syringe filter, washed with methanol (20 mL) and concentrated. Successful debenzylation was assessed by the disappearance of aromatic resonances by $^1$H NMR in $CD_3OD$. The residue was then dissolved in a pre-cooled (0° C.) solution of trifluoroacetic acid/water (4 mL, 3:1) and stirred for 1.25 h in an ice bath. After this time, the reaction was evaporated to dryness to give a white solid that was purified by RP-HPLC using a 30-70% acetonitrile/water (0.05% TFA) linear gradient, over 15 mini, at a flow rate of 5 mL/min. The desired product S26 (13 mg, 82% yield) was obtained as a white powder after lyophilization.

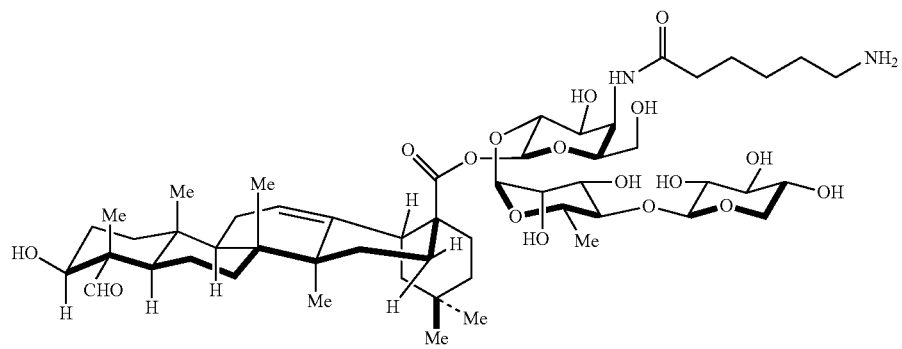

S26

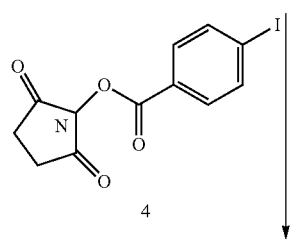

4

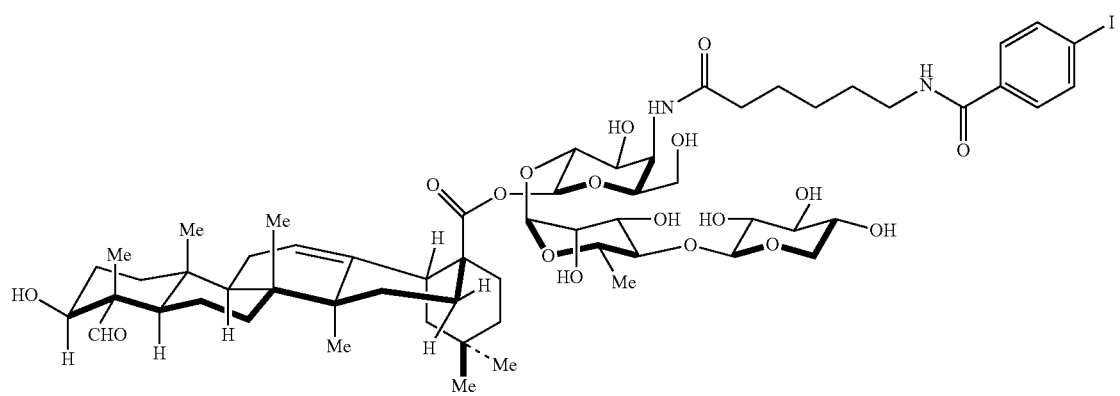

21 [SQS-1-9-5-18]

SQS-1-9-5-18 (21). (AF-I-230) In a 25 ml, round-bottom flask, amine S26 (6.6 mg, 6.5 μmol, 1.0 equiv) was dissolved in N,N'-dimethylformamide (2.0 mL) and triethylamine (18 μL, 0.13 mmol, 20 equiv) was injected. To this solution, 4 (11.1 mg, 32 μmol, 5.0 equiv) dissolved in N,N'-dimethylformamide (1.5 mL) was added dropwise and the reaction mixture was stirred at 21° C. for 3 h in the dark. After this time, the contents were diluted with 9 mL 25% acetonitrile/water (0.05% TFA) and directly purified by RP-HPLC using a 30-70% acetonitrile/water (0.05% TFA) linear gradient, over 15 min, at a flow rate of 5 mL/min. SQS-1-9-5-18 (21) (4.5 mg, 56% yield) was obtained as a white powder after lyophilization.

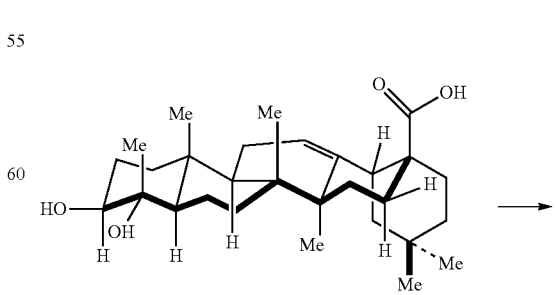

S15

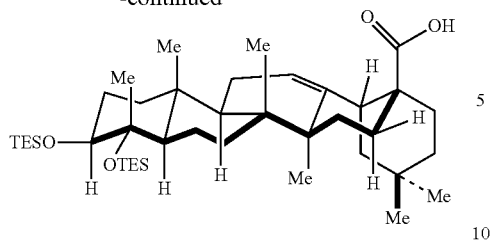

S16

Bis(silyl ether) of hederagenin (S18). (AFT-I-228) Hederagenin S15 (35 mg, 74 µmol, 1.0 equiv) was suspended in CH$_2$Cl$_2$ (15 mL) and cooled in an ice bath. 2,6-lutidine (138 µL, 1.18 mmol, 16 equiv) was then added followed by triethylsilyl trifluoromethanesulfonate (134 µL, 0.59 mmol, 8.0 equiv) and the reaction mixture was stirred at 0° C. for 1 h. After this time, the contents were washed with saturated NaHCO$_3$ (10 mL) and the aqueous phase was extracted with CH$_2$Cl$_2$ (2×15 mL). The combined organics were dried (Na$_2$SO$_4$), filtered, and concentrated. The crude product was purified several times by silica gel chromatography (hexanes to 4:1 hexanes/EtOAc) to afford S18 (45 mg, 81% yield).

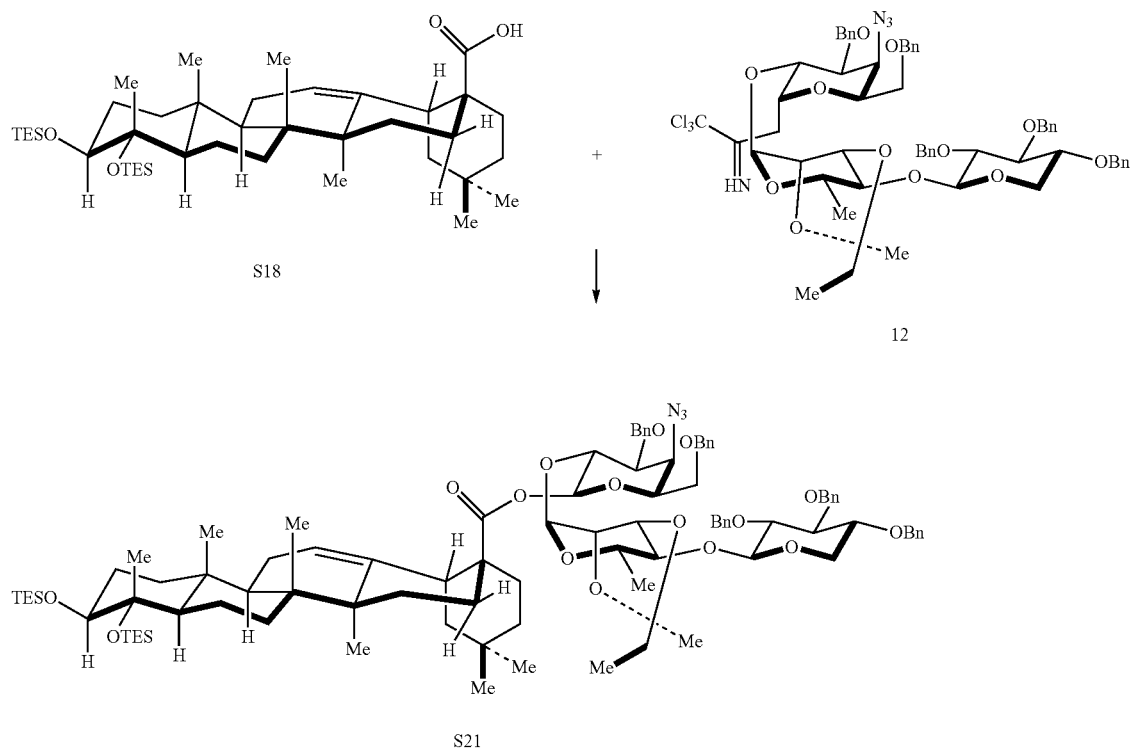

Protected hederagenin saponin azide S21. (AFT-I-232) A solution of S18 (28 mg, 40 µmol, 1.1 equiv) and imidate 12 (41 mg, 36.7 µmol, 1.0 equiv) in CH$_2$Cl$_2$ (5 mL) with 35 mg powdered 4 Å molecular sieves was cooled to −45° C. and boron trifluoride diethyletherate (0.9 µL, 7 µmol, 0.2 equiv) was added. The mixture was stirred at this temperature for 0.5 h, quenched with 0.2 mL of triethylamine and concentrated. Purification of the residue by silica gel chromatography (0.2% triethylamine in benzene to 98:2 benzene/EtOAc) afforded S21 (43 mg, 71% yield) as a glassy solid.

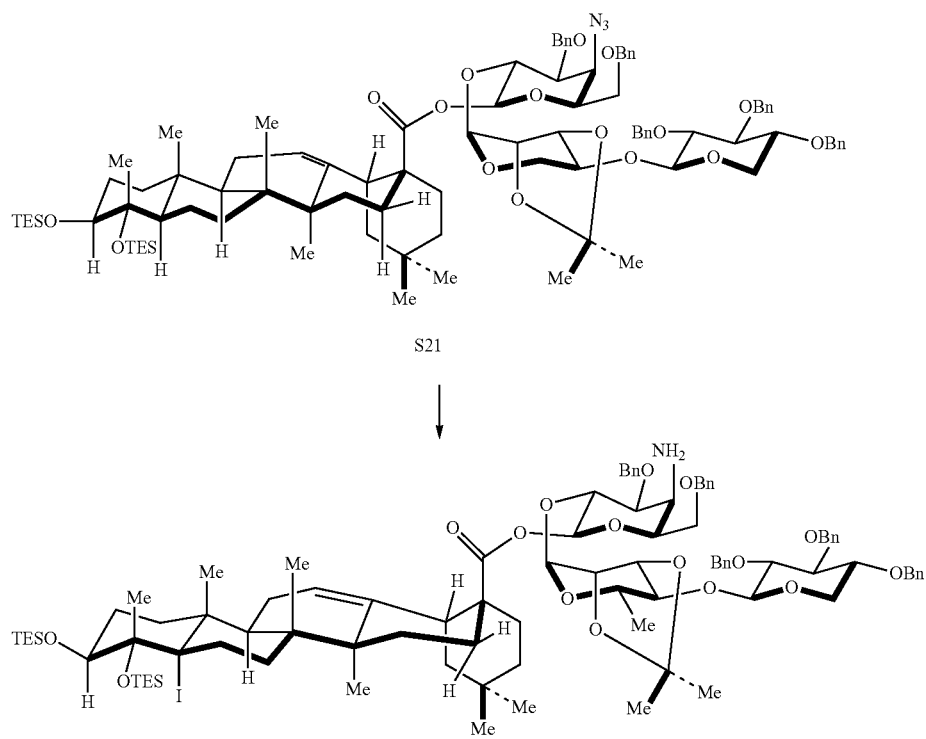

S21

↓

S33

Protected hederagenin saponin amine S33. (AFT-I-233) To S21 (44 mg, 26.5 μmol, 1.0 equiv) dissolved in triethylamine (24 mL) was added a freshly prepared solution of phenyl selenol (0.80 mmol, 30 equiv) via cannula. The reaction was stirred at 38° C. for 8 h and the solution was then concentrated to afford a yellow-white solid. The crude mixture was purified by silica gel chromatography (9:1 to 4:1 toluene/EtOAc) to afford the amine S33 (34.5 mg, 80% yield) as a glassy solid.

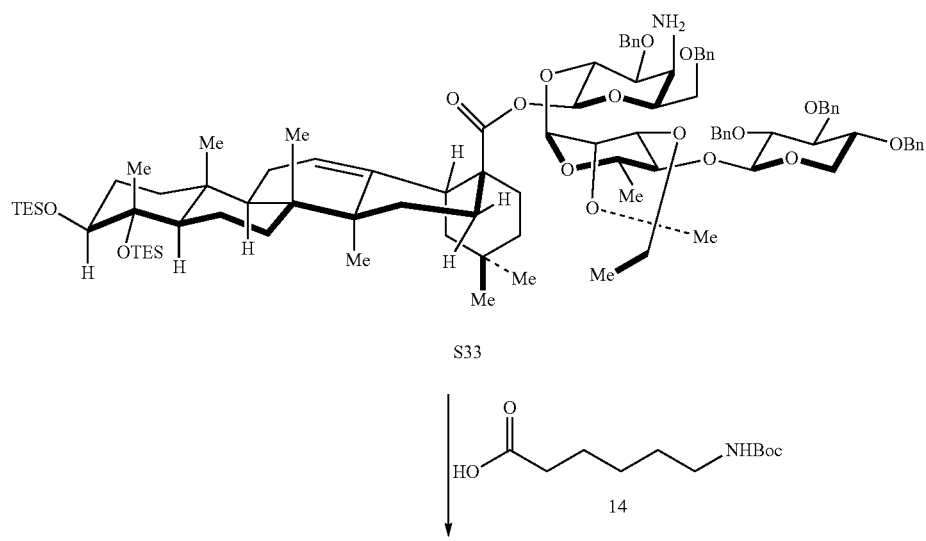

S33

↓

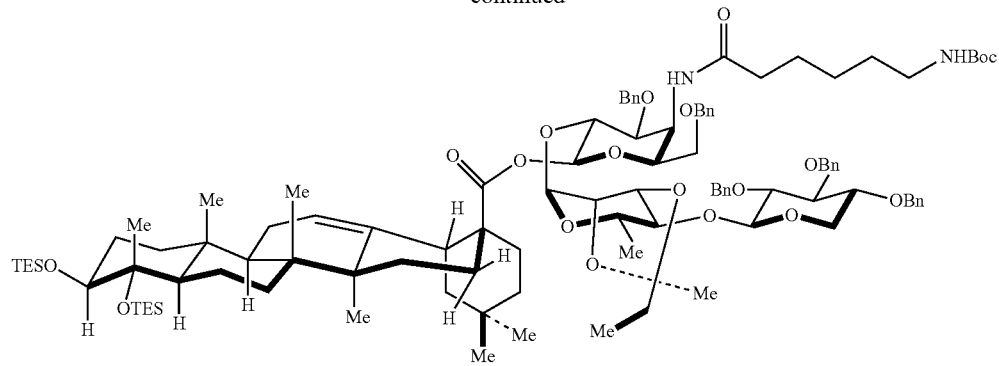

S24

Fully protected aminoacyl hederagenin saponin S24. (AFT-I-234) To a solution of 6-((i-butoxycarbonyl)-amino) hexanoic acid (14) (56 mg, 0.24 mmol, 11.5 equiv) in tetrahydrofuran (2.5 mL) at 0° C. was added triethylamine (263 µL, 1.89 mmol, 90 equiv) followed by ethyl chloroformate (20.0 µL, 0.21 mmol, 10.0 equiv). The turbid, white solution was stirred at 0° C. for 2.5 h and then added via cannula to amine S33 (34.5 mg, 21.0 µmol, 1.0 equiv) at 0° C. The reaction mixture was stirred at this temperature for 1.5 h and then quenched with water (0.2 mL) and concentrated. Purification by silica gel chromatography (9:1 to 5:1 benzene/EtOAc with 0.2% triethylamine) afforded S24 (36.5 mg, 92% yield) as a white solid.

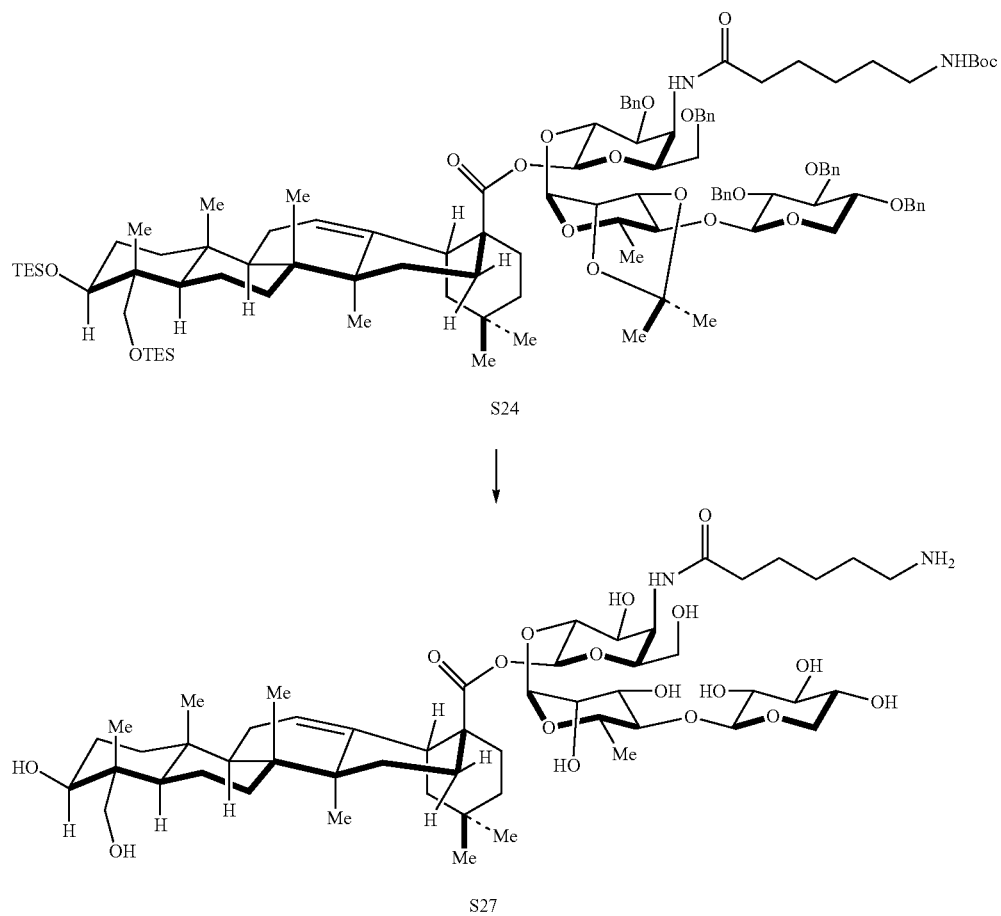

Aminoacyl hederagenin saponin S27. (AFT-I-235) In a 25 mL round-bottom flask, S24 (30 mg, 16.3 µmol, 1.0 equiv) was dissolved in tetrahydrofuran/ethanol (7 mL, 1:1) and 10% (dry basis) palladium on carbon, wet, Degussa type E101 NE/W (173 mg, 81 µmol, 5.0 equiv) was added. The reaction was stirred under hydrogen atmosphere (balloon) at 21° C. for 12 h, and then filtered through a 0.45 µm nylon syringe filter, washed with methanol (3×10 mL) and concentrated. Successful debenzylation is assessed by the disappearance of aromatic resonances by $^1$H NMR in CD$_3$OD. The crude mixture was then dissolved in a pre-cooled (0° C.) solution of trifluoroacetic acid (4 mL, TFA/H$_2$O 3:1) and stirred for 1.25 h in an ice bath. The reaction was evaporated to dryness and the white solid was dissolved in 30% acetonitrile/water (0.05% TFA) (14 mL) and purified via RP-HPLC on an XBridge Prep BEH300 C18 column (5 μm, 10×250 mm) using a linear gradient of 30-70% acetonitrile/water (0.05% TFA), over 15 min, at a flow rate of 5 mL/min. The desired product S27 was obtained as a white powder (11.0 mg, 66% yield) after lyophilization.

RP-HPLC on an XBridge Prep BEH300 C18 column (5 μm, 10×250 mm) using a linear gradient of 30-70% acetonitrile/water (0.05% TFA), over 15 min, at a flow rate of 5 mL/min. SQS-1-10-5-18 (22) (4.2 mg, 57% yield) was obtained as a white powder after lyophilization.

In summary, extensive structure-function studies of novel iodinated saponins based on QS-21 have identified echinocystic acid derivative 20 (SQS-1-8-5-18) as a minimal saponin immunoadjuvant with potent activity and dramatically reduced toxicity compared to the natural product (FIG. 5), as well as improved synthetic accessibility relative to previously reported variants. Subtyping of the IgG antibodies elicited by echinocystic acid derivative 20, as well as the

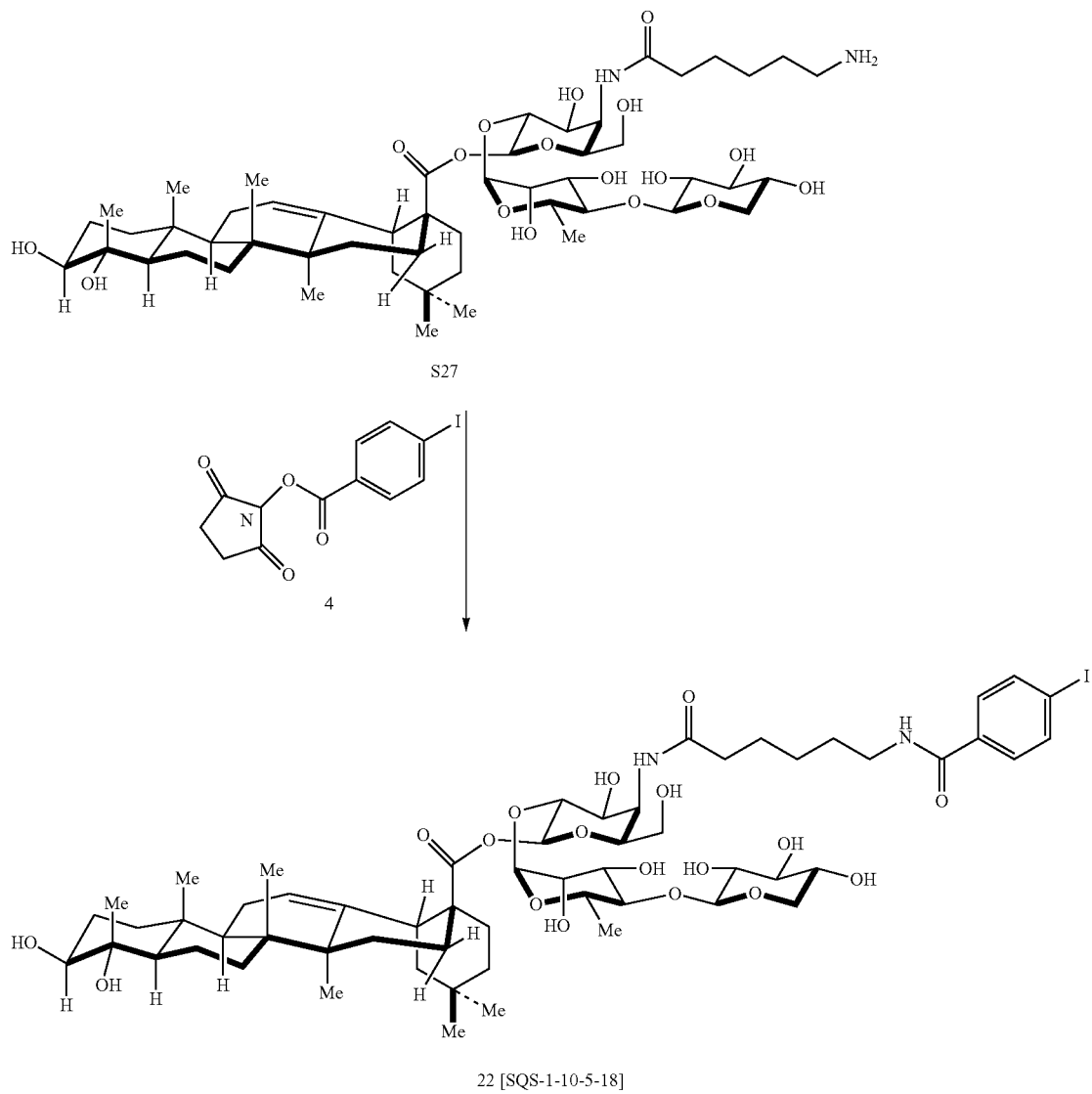

SQS-1-10-5-18 (22). (AF-I-236) S27 (6.0 mg, 5.8 μmol, 1.0 equiv) was dissolved in N,N'-dimethylformamide (2.5 mL) in a 25 mL round-bottom flask and triethylamine (16.3 μL, 0.12 mmol, 20 equiv) was injected. A solution of 4 (10.1 mg, 29 μmol, 5.0 equiv) in N,N'-dimethylformamide (1.5 mL) was added dropwise via syringe and the reaction was stirred at 21° C. for 3 h. After this time, the contents were diluted with 25% acetonitrile/water (9 mL) and purified via closely-related quillaic acid derivative 16 (SQS-1-0-5-18) and caulophyllogenin derivative 19 (SQS-1-11-5-18), indicates that IgG1 and IgG2b subclasses predominate. The mouse IgG1 subclass is associated with Th2 cell responses (humoral immunity), whereas the IgG2b, together with the IgG2a, are related to Th1 responses (cellular immunity) and are known to induce potent immunotherapeutic effector functions, including complement-dependent cytotoxicity and antibody-dependent cellular toxicity. Similar results were obtained with SQS-21. Thus, despite the considerable structural differences between these truncated saponins and QS-21, they elicit both Th1 and Th2 immunity, a hallmark of QS-21 itself.

To date, investigation of structural requirements within the triterpene domain of QS-21 has been hampered by the challenges associated with chemoselective modification of the natural product and by material throughput limitations for synthetic analogues that incorporate alternative triterpenes. Thus, the discovery that the entire branched trisaccharide domain can be omitted while retaining potent adjuvant activity and attenuating toxicity has opened the door to investigation of such triterpene modifications by semisynthesis from alternative, readily available triterpene precursors.

These studies revealed that the C4-aldehyde substituent is dispensable for potent adjuvant activity while the C16-hydroxyl group enhances activity in these truncated saponins. In contrast, the C4-aldehyde substituent of QS-21 has been suggested previously to react with amino groups on T-cell surface receptors through Schiff base formation, providing co-stimulation necessary for T-cell activation and Th1 cellular immunity. This hypothesis was based on the finding that reductive amination of the C4-aldehyde substituent of QS-21 provides amine derivatives with significantly attenuated adjuvant activity. However, this modification not only removes the C4-aldehyde substituent but also introduces a positively charged amino group at this position, which may alternatively compromise non-covalent interactions with a putative receptor or otherwise interfere with proper biodistribution or subcellular localization of the adjuvant. Along similar lines, QS-21 variant 2 (SQS-0-0-5-11), which retains the C4-aldehyde substituent but carries a positively-charged amino functionality in the acyl chain domain, was shown to be likewise inactive. While it remains possible that QS-21 and these modified, synthetic variants may have distinct molecular targets, they appear to induce similar cellular effects in vivo.

Conversely, the finding disclosed herein that the C16-hydroxyl group enhances adjuvant activity in these truncated saponins suggests a previously unappreciated role for this functionality, perhaps in stabilizing saponin conformation and/or interacting directly with a putative receptor. These results are consistent with reports of other adjuvant active saponins that possess the C16-hydroxyl group but lack the triterpene C4-aldehyde substituent.

What is claimed is:

1. A pharmaceutical composition comprising a compound of the following formula:

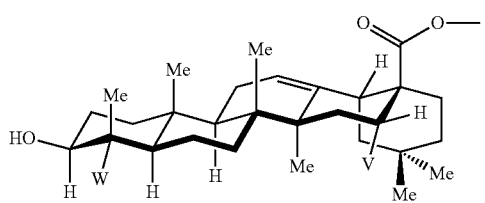

-continued

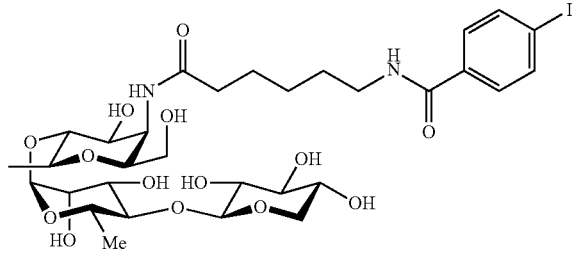

wherein
W is C(O)R, CH$_2$OR or CH$_2$R, wherein R is H, or an optionally substituted group selected from acyl, arylalkyl, aryl, heteroaryl, aliphatic, heteroaliphatic, cycloaliphatic and heterocyclyl groups, and
V is H or OH,
or a pharmaceutically acceptable salt thereof;
and
an immunologically effective amount of an antigen.

2. The pharmaceutical composition according to claim 1, wherein the antigen is associated with a bacteria or virus.

3. The pharmaceutical composition according to claim 2, wherein the antigen is associated with a virus and the virus is selected from the group consisting of influenza viruses, parainfluenza viruses, mumps virus, adenoviruses, respiratory syncytial virus, Epstein-Barr virus, rhinoviruses, polioviruses, coxsackieviruses, echo viruses, rubeola virus, rubella virus, varicella-zoster virus, herpes viruses, herpes simplex virus, parvoviruses, cytomegalovirus, hepatitis viruses, human papillomavirus, alphaviruses, flaviviruses, bunyaviruses, rabies virus, arenaviruses, filoviruses, HIV1, HIV 2, HTLV-1, HTLV-II, FeLV, bovine LV, FeIV, canine distemper virus, canine contagious hepatitis virus, feline calicivirus, feline rhinotracheitis virus, TGE virus, foot and mouth disease virus, and combinations thereof.

4. The pharmaceutical composition according to claim 2, wherein the antigen is associated with a bacteria and the bacteria is selected from the group consisting of *Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospria* spp., *Hemophilus ducreyi, Corynebacterium diphtheria, Bordetella pertussis, Bordetella parapertussis, Bordetella bronchiseptica,* hemophilus influenza, *Escherichia coli, Shigella* spp., *Erlichia* spp., *Rickettsia* spp., and combinations thereof.

5. The pharmaceutical composition according to claim 1, wherein the antigen is a tumor-associated antigen.

6. The pharmaceutical composition according to claim 5, wherein the tumor-associated antigen is selected from the group consisting of
killed tumor cells and lysates thereof,
MAGE-1, MAGE-3 and peptide fragments thereof,
human chorionic gonadotropin and peptide fragments thereof,
carcinoembryonic antigen and peptide fragments thereof,
alpha fetoprotein and peptide fragments thereof, pancreatic oncofetal antigen and peptide fragments thereof,
MUC-1 and peptide fragments thereof,
CA 125, CA 15-3, CA 19-9, CA 549, CA 195, and peptide fragments thereof,
prostate-specific antigens and peptide fragments thereof,
prostate-specific membrane antigen and peptide fragments thereof,
squamous cell carcinoma antigen and peptide fragments thereof,
ovarian cancer antigen and peptide fragments thereof,
pancreas cancer associated antigen and peptide fragments thereof,
Her1/neu and peptide fragments thereof,
gp-100 and peptide fragments thereof,
mutant K-ras proteins and peptide fragments thereof,
mutant p53 and peptide fragments thereof,
truncated epidermal growth factor receptor,
chimeric protein p210$^{BCR-ABL}$, KH-1, N3, GM1, GM2, GD2, GD3, Gb3, Globo-H, STn, Tn, Lewis$^x$, Lewis$^y$, TF,
and mixtures thereof.

7. A method of conferring resistance to an infection, comprising administering a pharmaceutical composition comprising an antigen and a compound of the following formula:

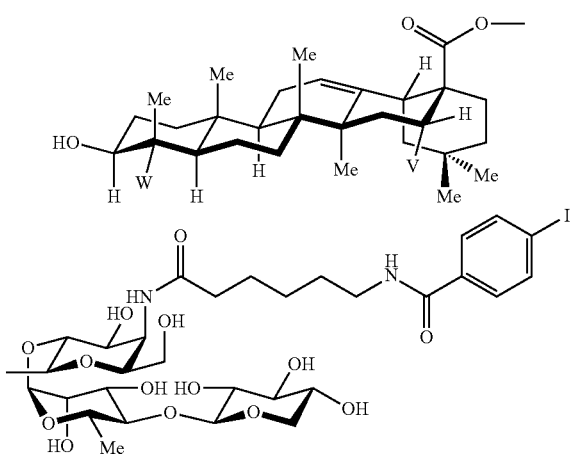

wherein
W is C(O)R, CH$_2$OR or CH$_2$R, wherein R is H, or an optionally substituted group selected from acyl, arylalkyl, aryl, heteroaryl, aliphatic, heteroaliphatic, cycloaliphatic and heterocyclyl groups, and
V is H or OH,
or a pharmaceutically acceptable salt thereof.

8. The method of claim 7, wherein the antigen is associated with a bacteria or virus.

9. The method according to claim 8, wherein the antigen is associated with a virus and the virus is selected from the group consisting of influenza viruses, parainfluenza viruses, mumps virus, adenoviruses, respiratory syncytial virus, Epstein-Barr virus, rhinoviruses, polioviruses, coxsackieviruses, echo viruses, rubeola virus, rubella virus, varicella-zoster virus, herpes viruses, herpes simplex virus, parvoviruses, cytomegalovirus, hepatitis viruses, human papillomavirus, alphaviruses, flaviviruses, bunyaviruses, rabies virus, arenaviruses, filoviruses, HIV1, HIV 2, HTLV-1, HTLV-II, FeLV, bovine LV, FeIV, canine distemper virus, canine contagious hepatitis virus, feline calicivirus, feline rhinotracheitis virus, TGE virus, foot and mouth disease virus, and combinations thereof.

10. The method according to claim 8, wherein the antigen is associated with a bacteria and the bacteria is selected from the group consisting of *Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospria* spp., *Hemophilus ducreyi, Corynebacterium diphtheria, Bordetella pertussis, Bordetella parapertussis, Bordetella bronchiseptica,* hemophilus influenza, *Escherichia coli, Shigella* spp., *Erlichia* spp., *Rickettsia* spp., and combinations thereof.

11. The method according to claim 7, wherein the antigen is a tumor-associated antigen.

12. The method according to claim 11, wherein the tumor-associated antigen is selected from the group consisting of
killed tumor cells and lysates thereof,
MAGE-1, MAGE-3 and peptide fragments thereof,
human chorionic gonadotropin and peptide fragments thereof,
carcinoembryonic antigen and peptide fragments thereof,
alpha fetoprotein and peptide fragments thereof,
pancreatic oncofetal antigen and peptide fragments thereof,
MUC-1 and peptide fragments thereof,
CA 125, CA 15-3, CA 19-9, CA 549, CA 195, and peptide fragments thereof,
prostate-specific antigens and peptide fragments thereof,
prostate-specific membrane antigen and peptide fragments thereof,
squamous cell carcinoma antigen and peptide fragments thereof,
ovarian cancer antigen and peptide fragments thereof,
pancreas cancer associated antigen and peptide fragments thereof,
Her1/neu and peptide fragments thereof,
gp-100 and peptide fragments thereof,
mutant K-ras proteins and peptide fragments thereof,
mutant p53 and peptide fragments thereof,
truncated epidermal growth factor receptor,
chimeric protein p210$^{BCR-ABL}$, KH-1, N3, GM1, GM2, GD2, GD3, Gb3, Globo-H, STn, Tn, Lewis$^x$, Lewis$^y$, TF,
and mixtures thereof.

13. A method of obtaining a compound according to claim 1, comprising
providing the compound according to claim 1 and a second substance, and
subsequently purifying the compound of claim 1 by removing at least a portion of the second substance.

* * * * *